United States Patent
Larsen et al.

(10) Patent No.: US 10,842,163 B2
(45) Date of Patent: Nov. 24, 2020

(54) RECOMBINANT HOST CELL EXPRESSING BETA-GALACTOSIDASE AND/OR TRANSGALACTOSYLATING ACTIVITY DEFICIENT IN MANNANASE, CELLULASE AND PECTINASE

(71) Applicant: DuPont Nutrition Biosciences APS, Copenhagen (DK)

(72) Inventors: Morten Krog Larsen, Sabro (DK); Jacob Flyvholm Cramer, Højbjerg (DK); Jeremy Labarge, Copenhagen (DK); Thomas Eisele, Hørning (DK); Karina Hansen Kjær, Skødstrup (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 91 days.

(21) Appl. No.: 15/524,807

(22) PCT Filed: Nov. 6, 2015

(86) PCT No.: PCT/EP2015/075950
§ 371 (c)(1),
(2) Date: May 5, 2017

(87) PCT Pub. No.: WO2016/071504
PCT Pub. Date: May 12, 2016

(65) Prior Publication Data
US 2019/0021352 A1   Jan. 24, 2019

(30) Foreign Application Priority Data

Nov. 7, 2014 (GB) .................................. 1419894.9
Nov. 7, 2014 (GB) .................................. 1419897.2
Nov. 7, 2014 (GB) .................................. 1419900.4
Sep. 3, 2015 (GB) .................................. 1515645.8

(51) Int. Cl.
*A23C 9/12* (2006.01)
*A23L 33/21* (2016.01)
*A23G 9/38* (2006.01)
*A23L 33/135* (2016.01)
*C12N 9/38* (2006.01)
*C12N 9/34* (2006.01)

(52) U.S. Cl.
CPC .......... *A23C 9/1206* (2013.01); *A23C 9/1216* (2013.01); *A23G 9/38* (2013.01); *A23L 33/135* (2016.08); *A23L 33/21* (2016.08); *C12N 9/2428* (2013.01); *C12N 9/2471* (2013.01); *C12Y 302/01023* (2013.01); *A23C 2220/202* (2013.01)

(58) Field of Classification Search
None
See application file for complete search history.

(56) References Cited

U.S. PATENT DOCUMENTS

| 6,022,725 A | 2/2000 | Fowler et al. |
| 6,268,328 B1 | 7/2001 | Mitchinson et al. |
| 9,107,440 B2 | 8/2015 | Larsen et al. |
| 2006/0223140 A1 | 10/2006 | Oura et al. |
| 2012/0040051 A1 | 2/2012 | Chen et al. |
| 2015/0223481 A1* | 8/2015 | Larsen ................ C12N 9/2468 426/42 |

FOREIGN PATENT DOCUMENTS

| CN | 101396048 A | 4/2009 |
| CN | 101845424 A | 9/2010 |
| EP | 0323201 A2 | 7/1989 |
| EP | 0458358 A1 | 11/1991 |
| EP | 0244234 B2 | 11/2001 |
| EP | 0215594 B2 | 10/2003 |
| EP | 2439270 A1 | 4/2012 |
| WO | 0190317 A2 | 11/2001 |
| WO | 2008037839 A1 | 4/2008 |
| WO | 2008088751 A2 | 7/2008 |
| WO | 2009071539 A1 | 6/2009 |
| WO | 2011120993 A1 | 10/2011 |
| WO | 2012010597 A1 | 1/2012 |
| WO | 2013182686 A1 | 12/2013 |
| WO | 2015061135 A1 | 4/2015 |
| WO | 2015086746 A1 | 6/2015 |
| WO | 2016071500 A1 | 5/2016 |

OTHER PUBLICATIONS

Slovakova et al. Fermentation of pectin and glucose, and activity of pectin-degrading enzymes in the rabbit caecal bacterium Bifidobacterium pseudolongum. Letters in Appl Microbiol (2002), 35: 126-130.*

Goulas et al. Molecular cloning and comparative analysis of four β-galactosidase genes from Bifidobacterium bifidum NCIMB41171. Appl Microbiol Biotechnol (2007), 76(6):1365-72. Epub Aug. 8, 2007.*

Waldeck et al. Targeted deletion of genes encoding extracellular enzymes in Bacillus licheniformis and the impact on the secretion capability. Journal of Biotechnology 130 (2007) 124-132.*

Okano et al. Biotechnological production of enantiomeric pure lactic acid from renewable resources: recent achievements, perspectives, and limits. Appl Microbiol Biotechnol (2010) 85:413-423.*

Otieno, 'Synthesis of β-Galactooligosaccharides from Lactose Using Microbial β-Galactosidases,' Comprehensive Reviews in Food Science and Food Safety, 2010, vol. 9, pp. 471-482.

Alloue et al., 'Storage of Yarrowia lipolytica lipase after spray-drying in the presence of additives,' Process Biochemistry, 2007, pp. 1357-1361, vol. 42.

(Continued)

*Primary Examiner* — Iqbal H Chowdhury

(57) ABSTRACT

A host cell capable of expressing a polypeptide having β-galactosidase and/or transgalactosylating activity and which host cell is modified to be cellulase, mannanase and pectinase deficient.

7 Claims, 3 Drawing Sheets

Specification includes a Sequence Listing.

(56) References Cited

OTHER PUBLICATIONS

Belghith et al., Stabilization of Penicillium occitanis cellulases by spray drying in presence of Maltodextrin, Enzyme and Microbial Technology, 2001, pp. 253-258, vol. 28.

Bolotin et al., 'The complete genome sequence of the lactic acid bacterium *lactococcus lactis* ssp. *Lactis* IL1403,' Genome Research, May 31, 2001, pp. 731-753, vol. 11, No. 5.

Endress et al., 'Pectin'; '27.2.3'; In: Susan S. Cho and Nelson Almeida: 'Dietary Fiber and Health', Apr. 13, 2012, p. 392.

Ghorab et al., 'Water-solid interactions between amorphous maltodextrins and crystalline sodium chloride,' Food Chemistry, 2014, pp. 26-35, vol. 144.

Gosling et al. 'Recent advances refining galactooligosaccharide production from lactose,' Feed Chemistry, Jul. 15, 2010, pp. 307-318, vol. 121, No. 2.

Hernandez-Hernandez et al., 'Characterization of galactooligosaccharides derived from lactulose,' Journal of Chromatography A, 2011, pp. 7691-7696, vol. 1218.

Hung et al., 'Purification and characterization of a recombinant β-galactosidase with transgalactosylation activity from Bifidobacterium infantis HL96,' Appl Microbiol. Biotechnol., 2002, pp. 439-445, vol. 58.

Irazoqui et al., 'Substrate-like inhibition of the transgalactosylation reaction catalyzed by β-galactosidase from Aspergillus oryzae,' Biocatalysis and Biotransformation, 2013, pp. 57-65, vol. 31(1).

Jorgensen et al., 'High-efficiency synthesis of oligosaccharides with a truncated β-galactosidase from Bifidobacterium bifidum,' Appl Microbiol Biotechnol., 2001, pp. 647-652, vol. 57.

Oliveira et al., 'Recombinant microbial systems for improved β-galactosidase production and biotechnological applications,' Biotechnology Advances, Apr. 13, 2011, pp. 600-609, vol. 29.

Perdana et al., 'Mimicking spray drying by drying of single droplets deposited on a flat service,' Food Bioprocess Technol., 2013, pp. 964-977, vol. 6.

Pokusaeva et al., 'Carbohydrate metabolism in Bifidobacteria,' Genes Nutr, 2011, pp. 285-306, vol. 6.

Rodriguez-Colinas et al., 'Galacto-oligosaccharide dynthesis from lactose solution or skin milk using the β-Galactosidase from Bacillus circulans,' The Journal of Agricultural and Food Chemistry, 2012, pp. 6391-6398, vol. 60.

Schutyser et al., 'Single droplet drying for optimal spray drying of enzymes and probiotics,' Trends in Food Science & Technology, 2012, pp. 73-82, vol. 27.

Sreekumar et al., 'Isolation and characterization of probiotic Bacillus subtilis SK09 from dairy effluent,' Indian Journal of Science and Technology, 2010, pp. 863-866, vol. 3, No. 8.

Vijayalaxmi et al., 'Production of Bioethanol from fermented sugars of sugarcane bagasse produced by ignocellulolytic enzymes of Exiguobacterium sp. VSG-1', Appl Biochem Biotechnol., 2013, pp. 246-260, vol. 171.

International Search Report issued for PCT/EP2015/075950 dated Apr. 15, 2016.

Written Opinion issued for PCT/EP2015/075950 dated Apr. 15, 2016.

\* cited by examiner

RECOMBINANT HOST CELL EXPRESSING BETA-GALACTOSIDASE AND/OR TRANSGALACTOSYLATING ACTIVITY DEFICIENT IN MANNANASE, CELLULASE AND PECTINASE

CROSS-REFERENCE TO RELATED APPLICATIONS

This application claims priority under 35 USC § 371 as a national phase of International Patent Application No. PCT/EP2015/075950 (filed Nov. 6, 2015; and published on May 12, 2016 as Publication No. WO2016071504), which claims priority to and the benefit of United Kingdom Patent Application Nos. GB 1515645.8, filed Sep. 3, 2015, GB 1419894.9, filed Nov. 7, 2014, GB 1419897.2, filed Nov. 7, 2014 and GB 1419900.4, filed Nov. 7, 2014, all of which are hereby incorporated by reference in their entirety.

FIELD OF THE INVENTION

The invention relates to a host cell wherein undesirable enzymes are inactivated, and the use of this host cell in the preparation of an enzyme composition for use in the manufacture of a food product with reduced unwanted properties.

BACKGROUND TO THE INVENTION

The use of enzymes to improve the chemical nature of food products is wide spread. Also in the processing of cow's milk and other animal derived substrates, the use of enzyme adds significant value to the end product.

Galactooligosaccharides (GOS) are carbohydrates which are nondigestable in humans and animals comprising two or more galactose molecules, typically up to nine, linked by glycosidic bonds. GOS's may also include one or more glucose molecules. One of the beneficial effects of GOS's is their ability of acting as prebiotic compounds by selectively stimulating the proliferation of beneficial colonic microorganisms such as bacteria to give physiological benefits to the consumer. The established health effects have resulted in a growing interest in GOSs as food ingredients for various types of food.

The enzyme β-galactosidase (EC 3.2.1.23) usually hydrolyses lactose to the monosaccharides D-glucose and D-galactose. In the normal enzyme reaction of β-galactosidases, the enzyme hydrolyses lactose and transiently binds the galactose monosaccharide in a galactose-enzyme complex that transfers galactose to the hydroxyl group of water, resulting in the liberation of D-galactose and D-glucose. However, at high lactose concentrations some β-galactosidases are able to transfer galactose to the hydroxyl groups of D-galactose or D-glucose in a process called transgalactosylation whereby galacto-oligosaccharides are produced. Also at high lactose concentrations some β-galactosidases are able to transfer galactose to the hydroxyl groups of lactose or higher order oligosaccharides.

The genus Bifidobacterium is one of the most commonly used types of bacteria cultures in the dairy industry for fermenting a variety of diary products. Ingestion of Bifidobacterium-containing products furthermore has a health-promoting effect. This effect is not only achieved by a lowered pH of the intestinal contents but also by the ability of Bifidobacterium to repopulate the intestinal flora in individuals who have had their intestinal flora disturbed by for example intake of antibiotics. Bifidobacterium furthermore has the potential of outcompeting potential harmful intestinal micro-organisms.

Galacto-oligosaccharides are known to enhance the growth of Bifidobacterium. This effect is likely achieved through the unique ability of Bifidobacterium to exploit galacto-oligosaccharides as a carbon source. Dietary supplement of galacto-oligosaccharides is furthermore thought to have a number of long-term disease protecting effects. For example, galacto-oligosaccharide intake has been shown to be highly protective against development of colorectal cancer in rats. There is therefore a great interest in developing cheap and efficient methods for producing galacto-oligosaccharides for use in the industry for improving dietary supplements and dairy products.

An extracellular lactase from Bifidobacterium bifidum DSM20215 truncated with approximately 580 amino acids (BIF3-d3) has been described as a transgalactosylating enzyme in a solution containing lactose solubilised in water (Jørgensen et al. (2001), Appl. Microbiol. Biotechnol., 57: 647-652). WO 01/90317 also describes a truncation variant (OLGA347) as being a transgalactosylating enzyme and in WO 2012/010597 OLGA347 was shown to transfer a galactose moiety to D-fucose, N-acetyl-galactosamine and xylose.

In WO 2009/071539 a differently truncated fragment compared to BIF3-d3 is described as resulting in efficient hydrolysis and very low production of GOS when tested in milk.

WO 2013/182686 describes a polypeptide which has a useful ratio of transgalactosylation to hydrolysis activity and thus is an efficient producer of GOS when incubated with lactose even at low lactose levels such as in a milk-based product.

There remains however the need to provide improved processes for producing dietary fibers in the form of GOS in situ from lactose in diary products. The present invention addresses this need.

SUMMARY OF THE INVENTION

Enzyme side activity typically describes unwanted enzymes whose activity negatively affects a process or product. They are mainly found in enzyme products as a byproduct of, for example, a production host, and may hinder the commercial application of such enzymes. Dairy applications are especially sensitive to small amounts of cellulase, pectinase, amylase and mannanase enzymes as many dairy products are formulated/stabilized with hydrocolloids e.g. CMC, GUAR, starch and pectin (see Table 1).

TABLE 1

| Enzyme | Degradable hydrocolloid/stabilizer |
| --- | --- |
| Cellulase | CMC |
| Mannanase | GUAR, LBG |
| Pectinase (pectate lyase) | Pectin |
| Amylase | Starch |

We have now been able to develop a product containing β-galactosidase activity, optionally having transgalactosylating activity, or GOS produced therefrom wherein the levels of cellulose, mannanase, pectinase and amylase are reduced. As thickening, gelling and stabilising agents, hydrocolloids make an important contribution to numerous food and beverage products. The present invention allows the provision of such food and beverage products in which not only are the desired properties from the use of hydrocolloids retained, but in which additionally the food and beverage products are able to retain dietary fibers in the form of GOS.

Hydrocolloids or gums are a diverse group of long chain polymers characterized by their property of forming viscous dispersions and/or gels when dispersed in water. These materials were first found in exudates from trees or bushes, extracts from plants or seaweeds, flours from seeds or grains, gummy slimes from fermentation processes, and many other natural products. Occurrence of a large number of hydroxyl groups noticeably increases their affinity for binding water molecules rendering them hydrophilic compounds. Further, they produce a dispersion, which is intermediate between a true solution and a suspension, and exhibits the properties of a colloid. Considering these two properties, they are appropriately termed as 'hydrophilic colloids' or 'hydrocolloids'.

Hydrocolloids have a wide array of functional properties in foods including; thickening, gelling, emulsifying, stabilization, coating and etc. Hydrocolloids have a profound impact on food properties when used at levels ranging from a few parts per million for carrageenan in heat-treated dairy products to high levels of acacia gum, starch or gelatin in jelly confectionery. The primary reason behind the ample use of hydrocolloids in foods is their ability to modify the rheology of food systems. This includes two basic properties of food systems that is, flow behaviour (viscosity) and mechanical solid property (texture). The modification of texture and/or viscosity of food systems helps modify its sensory properties, therefore hydrocolloids are used as significant food additives to perform specific purposes. It is evident that several hydrocolloids belong to the category of permitted food additive in many countries throughout the world. Various food formulations such as soups, gravies, salad dressings, sauces and toppings use hydrocolloids as additives to achieve the preferred viscosity and mouth feel. They are also used in many food products like ice-creams, jams, jellies, gelled desserts, cakes and candies, to create the desired texture.

In addition to the functional attributes, future acceptance and, possibly, positive endorsement may derive from the recognition that fibers contribute many physiological benefits to the natural function and well-being of the body.

Due to their water-binding properties, hydrocolloids have a significant influence on the texture and mouthfeel of food products—often creating opportunities for textural innovation. Several of the products also interact with protein, a useful property for protein stabilisation and protection. The present invention provide solutions based on the use of hydrocolloids in which not only are the afore-mentioned desired properties from the use of hydrocolloids retained, but in which additionally the food and beverage products are able to contain dietary fibers in the form of GOS.

In cultured products hydrocolloids provide smooth texture and shiny appearance. Hydrocolloids can optimise cost in reduced milk solid formulations as well as maintain texture throughout shelf life. Hydrocolloids also improve body, especially at a higher consumption temperature for cultured products. The present invention provide solutions based on the use of hydrocolloids in which not only are the afore-mentioned desired properties from the use of hydrocolloids retained, but in which additionally the food and beverage products are able to contain dietary fibers in the form of GOS.

In dairy products & low pH protein drinks hydrocolloids can stabilise milk and soya protein, prevent sedimentation and whey off and enable a wide range of textures. Further more hydrocolloids can replace texture in formulations with reduced milk solids, sugar and/or fat and thereby give the food manufacture a better low fat product. The present invention provide solutions based on the use of hydrocolloids in which not only are the afore-mentioned desired properties from the use of hydrocolloids retained, but in which additionally the food and beverage products are able to contain dietary fibers in the form of GOS.

The present invention addresses the issues by providing a enzyme composition comprising a polypeptide which has transgalactosylating activity, but which enzyme composition has no or substantially no activity attributable to the following enzymes: cellulose, mannanase, pectinase, and optionally amylase.

According to a $1^{st}$ aspect of the invention there is provided a host cell capable of expressing a polypeptide having β-galactosidase activity and which host cell is modified to be cellulase, mannanase and pectinase deficient.

In a preferred embodiment the polypeptide having β-galactosidase activity as used in the invention has transgalactosylating activity.

According to $2^{nd}$ aspect of the invention there is provided a host cell capable of expressing a polypeptide having transgalactosylating activity and which host cell is modified to be cellulase, mannanase and pectinase deficient.

Preferably the host cell is modified to also be amylase deficient.

In one embodiment the host cell is modified by conventional mutagenesis techniques.

In another embodiment the host cell is modified by conventional genetic manipulation techniques.

According to a $3^{rd}$ aspect of the invention there is to be provided a host cell capable of expressing a polypeptide having β-galactosidase activity and wherein polypeptides having cellulase, mannanase and pectinase activity are essentially inactive.

According to a $4^{th}$ aspect of the invention there is provided a host cell capable of expressing a polypeptide having transgalactosylating activity and wherein polypeptides having cellulase, mannanase and pectinase activity are essentially inactive.

Preferably in the host cell additionally a polypeptide having amylase activity is essentially inactive.

In one embodiment in the $3^{rd}$ and $4^{th}$ aspects the essentially inactive cellulase, mannanase and pectinase polypeptides, and optionally the amylase polypeptide, are functionally inactive with respect to enzymatic activity.

In one embodiment in the polypeptides having cellulase, mannanase and pectinase activity, and optionally the polypeptide having amylase activity, are rendered essentially inactive by conventional mutagenesis techniques.

In another embodiment in the polypeptides having cellulase, mannanase and pectinase activity, and optionally the polypeptide having amylase activity, are rendered essentially inactive by conventional genetic manipulation techniques.

Conventional mutagenesis techniques which may be employed are chemical or physical mutagenesis.

Conventional genetic manipulation techniques which may be employed are one-step gene disruption, marker insertion, site directed mutagenesis, deletion, RNA interference or anti-sense RNA.

Preferably the host cell is a bacterium.

The host cell may be a lactic acid bacterium.

Preferably the host cell is *B. subtilis*.

Preferably the polypeptide having transgalactosylating activity employed in the invention is selected from the group consisting of:
a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues,
d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i),
e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
f. a polypeptide comprising a deletion, insertion and/or conservative substitution of one or more amino acid residues of SEQ ID NO: 1, 2, 3, 4 or 5.

In one embodiment the host cell comprises an expression vector comprising a nucleic acid encoding the polypeptide having β-galactosidase activity.

In one embodiment the host cell is transformed with a nucleic acid encoding the polypeptide having β-galactosidase activity.

In one embodiment the host cell comprises an expression vector comprising a nucleic acid encoding the polypeptide having transgalactosylating activity.

In one embodiment the host cell is transformed with a nucleic acid encoding the polypeptide having transgalactosylating activity.

According to a $5^{th}$ aspect of the invention there is provided a method for providing a polypeptide composition comprising a polypeptide having β-galactosidase activity and having a reduced content of undesired cellulose, mannanase and pectinase enzymatic side activities, the method comprising: providing a host cell capable of expressing the polypeptide having β-galactosidase activity, a polypeptide having cellulase activity, a polypeptide having mannanase activity and a polypeptide having pectinase activity; and inactivating said cellulose, mannanase and pectinase activity.

According to a $6^{th}$ aspect of the invention there is provided a method for providing a polypeptide composition comprising a polypeptide having transgalactosylating activity and having a reduced content of undesired cellulose, mannanase and pectinase enzymatic side activities, the method comprising: providing a host cell capable of expressing the polypeptide having transgalactosylating activity, a polypeptide having cellulase activity, a polypeptide having mannanase activity and a polypeptide having pectinase activity; and inactivating said cellulose, mannanase and pectinase activity.

Preferably the method further comprises inactivating a polypeptide having amylase activity.

In one embodiment of the method the polypeptides having cellulase, mannanase and pectinase activity, and optionally the polypeptide having amylase activity, are rendered essentially inactive by conventional mutagenesis techniques.

In another embodiment of the method the polypeptides having cellulase, mannanase and pectinase activity, and optionally the polypeptide having amylase activity, are rendered essentially inactive by genetic manipulation.

Preferably in the method the host cell is a bacterium.

In one embodiment in the method the host cell is a lactic acid bacterium.

Preferably in the method the host cell is *B. subtilis*.

Preferably in the method the polypeptide having transgalactosylating activity is selected from the group consisting of:
a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues,
d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i),
e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
f. a polypeptide comprising a deletion, insertion and/or conservative substitution of one or more amino acid residues of SEQ ID NO: 1, 2, 3, 4 or 5.

In one embodiment of the method the host cell comprises an expression vector comprising a nucleic acid encoding a polypeptide having β-galactosidase activity.

In another embodiment of the method the host cell is transformed with a nucleic acid encoding a polypeptide having β-galactosidase activity.

In one embodiment of the method the host cell comprises an expression vector comprising a nucleic acid encoding a polypeptide having transgalactosylating activity.

In another embodiment of the method the host cell is transformed with a nucleic acid encoding a polypeptide having transgalactosylating activity.

According to a $7^{th}$ aspect of the invention there is provided a method to produce a polypeptide having β-galactosidase activity comprising cultivating the host cell of the invention in a culture medium under suitable conditions to express the polypeptide having β-galactosidase activity, and optionally recovering the polypeptide having β-galactosidase activity from the culture medium or the host cell.

According to an $8^{th}$ aspect of the invention there is provided a method to produce a polypeptide having transgalactosylating activity comprising cultivating the host cell of the invention in a culture medium under suitable conditions to express the polypeptide having transgalactosylating activity, and optionally recovering the polypeptide having transgalactosylating activity from the culture medium or the host cell.

According to a 9$^{th}$ aspect of the invention there is provided a polypeptide having β-galactosidase activity which is produced using the host cell of the invention or the process of invention.

The polypeptide having β-galactosidase activity according to the invention is preferably free from or substantially free from cellulose, mannanase and pectinase activity, and optionally amylase activity.

In one embodiment the polypeptide having β-galactosidase activity according to the invention is free from or substantially free from cellulose, mannanase and pectinase activity such that the reduction in viscosity presented as a relative reduction in viscosity is at least 0.85 or at least 0.9, or less calculated from the viscosity of a hydrocolloid-containing solution to which the polypeptide having β-galactosidase activity is added compared to a hydrocolloid solution to which no enzyme or water is added.

According to a 10$^{th}$ aspect of the invention there is provided a polypeptide composition comprising a polypeptide having β-galactosidase activity produced using the host cell of the invention or the process of the invention.

According to an 11$^{th}$ aspect of the invention there is provided a polypeptide having transgalactosylating activity which is produced using the host cell of the invention or the process of invention.

The polypeptide having transgalactosylating activity according to the invention is preferably free from or substantially free from cellulose, mannanase and pectinase activity, and optionally amylase activity.

In one embodiment the polypeptide having transgalactosylating activity according to the invention is free from or substantially free from cellulose, mannanase and pectinase activity such that the reduction in viscosity presented as a relative reduction in viscosity is at least 0.85 or at least 0.9, or less calculated from the viscosity of a hydrocolloid-containing solution to which the polypeptide having transgalactosylating activity is added compared to a hydrocolloid solution to which no enzyme or water is added.

According to a 12$^{th}$ aspect of the invention there is provided a polypeptide composition comprising a polypeptide having transgalactosylating activity produced using the host cell of the invention or the process of the invention.

Preferably the polypeptide composition of the invention is free from or substantially free from cellulose, mannanase and pectinase activity, and optionally amylase activity.

In one embodiment the polypeptide composition is free from or substantially free from cellulose, mannanase and pectinase activity such that the reduction in viscosity presented as a relative reduction in viscosity is at least 0.85 or at least 0.9, or less calculated from the viscosity of a hydrocolloid-containing solution to which the polypeptide composition of the invention is added compared to a hydrocolloid solution to which no enzyme or water is added.

According to a 13$^{th}$ aspect of the invention there is provided a dairy product comprising the polypeptide having β-galactosidase activity of the invention or the polypeptide composition of the invention.

According to an 14$^{th}$ aspect of the invention there is provided a process to produce a dairy product which comprises adding a polypeptide having β-galactosidase activity of the invention or a polypeptide composition of the invention to a dairy product which comprises lactose.

According to a 15$^{th}$ aspect of the invention there is provided a process to produce a dairy product which comprises GOS which process comprises adding a polypeptide having β-galactosidase activity of the invention or a polypeptide composition of the invention to a dairy product which comprises lactose.

According to a 16$^{th}$ aspect of the invention there is provided use of polypeptide having transgalactosylating activity according to the invention or a polypeptide composition according to the invention to prepare a dairy product.

According to a 17$^{th}$ aspect of the invention there is provided use of polypeptide having transgalactosylating activity according to the invention or a polypeptide composition according to the invention to prepare a dairy product comprising GOS.

According to an 18$^{th}$ aspect of the invention there is provided a dairy product comprising the polypeptide having transgalactosylating activity of the invention or the polypeptide composition of the invention.

According to a 19$^{th}$ aspect of the invention there is provided a process to produce a dairy product which comprises adding a polypeptide having transgalactosylating activity of the invention or a polypeptide composition of the invention to a dairy product which comprises lactose.

According to a 20$^{th}$ aspect of the invention there is provided a process to produce a dairy product which comprises GOS which process comprises adding a polypeptide having transgalactosylating activity of the invention or a polypeptide composition of the invention to a dairy product which comprises lactose.

According to a 21$^{st}$ aspect of the invention there is provided use of polypeptide having transgalactosylating activity according to the invention or a polypeptide composition according to the invention to prepare a dairy product.

According to an 22$^{nd}$ aspect of the invention there is provided use of polypeptide having transgalactosylating activity according to the invention or a polypeptide composition according to the invention to prepare a dairy product comprising GOS.

In one embodiment the use of the invention is to prevent a reduction in the viscosity and/or texture of the dairy product compared to the use of polypeptide having transgalactosylating activity which is prepared from a host cell which expresses cellulase, mannanase and pectinase.

The invention is particularly useful for the in situ production of GOS dietary fibers in a composition, such as a dairy product, comprising lactose.

SEQUENCE LISTING

SEQ ID NO: 1 (also named (BIF_917) herein) is a 887 amino acid truncated fragment of SEQ ID NO: 22.

SEQ ID NO: 2 (also named (BIF_995) herein) is a 965 amino acid truncated fragment of SEQ ID NO: 22.

SEQ ID NO: 3 (also named (BIF_1068) herein) is a 1038 amino acid truncated fragment of SEQ ID NO: 22.

SEQ ID NO: 4 (also named (BIF_1172) herein) is a 1142 amino acid truncated fragment of SEQ ID NO: 22.

SEQ ID NO: 5 (also named (BIF_1241) herein) is a 1211 amino acid truncated fragment of SEQ ID NO: 22.

SEQ ID NO: 6 (also named (BIF_1326) herein) is a 1296 amino acid truncated fragment of SEQ ID NO: 22.

SEQ ID NO: 7 is *Bifidobacterium bifidum* glycoside hydrolase catalytic core

SEQ ID NO: 8 is a nucleotide sequence encoding an extracellular lactase from *Bifidobacterium bifidum* DSM20215

SEQ ID NO: 9 is nucleotide sequence encoding BIF_917

SEQ ID NO: 10 is nucleotide sequence encoding BIF_995

SEQ ID NO: 11 is nucleotide sequence encoding BIF_1068

SEQ ID NO: 12 is nucleotide sequence encoding BIF_1172

SEQ ID NO: 13 is nucleotide sequence encoding BIF_1241

SEQ ID NO: 14 is nucleotide sequence encoding BIF_1326

SEQ ID NO: 15 is forward primer for generation of above BIF variants

SEQ ID NO: 16 is reverse primer for BIF917
SEQ ID NO: 17 is reverse primer for BIF995
SEQ ID NO: 18 is reverse primer for BIF1068
SEQ ID NO: 19 is reverse primer for BIF1241
SEQ ID NO: 20 is reverse primer for BIF1326
SEQ ID NO: 21 is reverse primer for BIF1478
SEQ ID NO: 22 is extracellular lactase from *Bifidobacterium bifidum* DSM20215.

SEQ ID NO: 23 is signal sequence of extracellular lactase from *Bifidobacterium bifidum* DSM20215.

DETAILED DISCLOSURE OF THE INVENTION

Definitions

Figure 1:
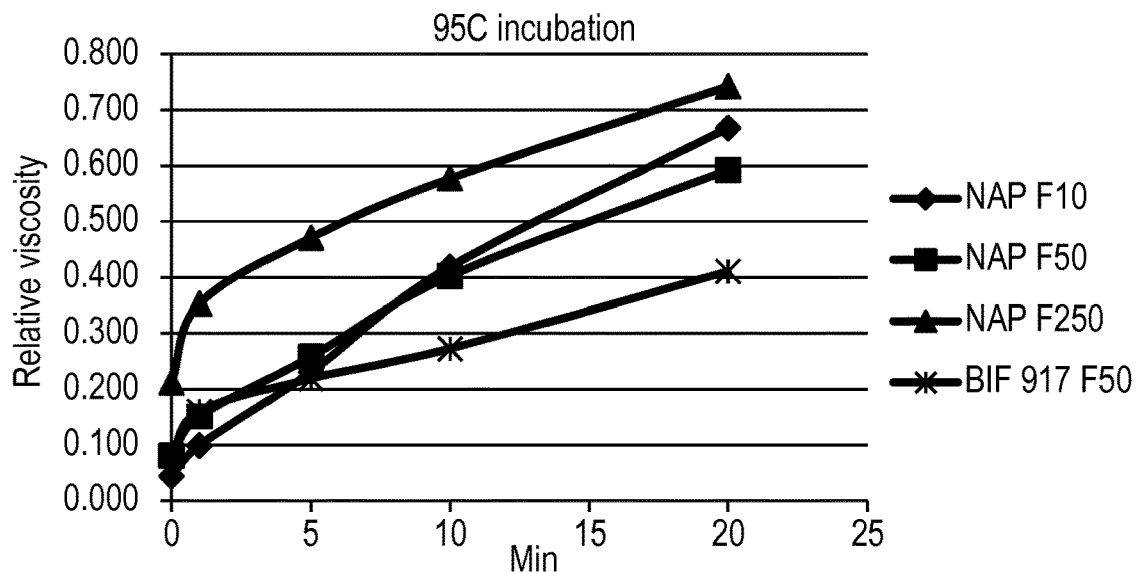
FIG. 1 shows relative viscosity plotted against time for the indicated samples.

In accordance with this detailed description, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

"Transgalactosylase" means an enzyme that, among other things, is able to transfer galactose to the hydroxyl groups of D-galactose or D-glucose whereby galacto-oligosaccharides are produced. In one aspect, a transgalactosylase is identified by reaction of the enzyme on lactose in which the amount of galactose generated is less than the amount of glucose generated at any given time.

In the present context, the term "transgalactosylating activity" means the transfer of a galactose moiety to a molecule other than water. The activity can be measured as [glucose]–[galactose] generated at any given time during reaction or by direct quantification of the GOS generated at any given time during the reaction. This measurement may be performed in several ways such as by a HPLC method as shown in the examples. When comparing measurements of transgalactosylating activity, they have been performed at a given initial lactose concentration, such as e.g. 3, 4, 5, 6, 7, 8, 9 or 10% (w/w).

In the present context, the term "β-galactosidase activity" means the ability of an enzyme to hydrolyse β-galactosides such as for example lactose into monosaccharides, glucose and galactose.

In the context of calculating transgalactosylating activity: β-galactosidase activity, the β-galactosidase activity is measured as [galactose] generated at any given time during reaction. This measurement may be performed in several ways such as by a HPLC method as shown in the examples.

In the present context, the term "ratio of transgalactosylation activity" using ortho-nitrophenol-β-D-galactopyranoside (ONPG) was calculated as follows: Ratio is calculated as ratio between Abs420 with acceptor present divided by Abs420 without acceptor present times 100. Variant at or below index 100 are purely hydrolytic variants, whereas the level above depicts relative transgalactosylating activity.

Ratio of transgalactosylation activity=(Abs420$^{+Cellobiose}$/Abs420$^{-Cellobiose}$)*100%, where Abs420$^{+Cellobiose}$ is the absorbance read at 420 nm using the described method 3 below including cellobiose in the reaction and Abs420$^{-Cellobiose}$ is the absorbance read at 420 nm using the described method 3 below but without cellobiose in the reaction. The equation above is only valid for dilutions where the absorbance is between 0.5 and 1.0.

In one aspect, the activity of any of the enzymes to which the present invention relates is measured after 15 min. reaction, 30 min. reaction, 60 min. reaction, 90 min. reaction, 120 min. reaction or 180 min. reaction. Thus in one aspect, as an example the relative transgalactosylation activity is measured 15 minutes after addition of enzyme, such as 30 minutes after addition of enzyme, such as 60 minutes after addition of enzyme, such as 90 minutes after addition of enzyme, such as 120 minutes after addition of enzyme or such as 180 minutes after addition of enzyme.

In the present context, the term "ratio of transgalactosylating activity:β-galactosidase activity" means ([Glucose]–[Galactose]/[Galactose]).

In the present context, the term [Glucose] means the glucose concentration in % by weight as measured by HPLC.

In the present context, the term [Galactose] means the galactose concentration in % by weight as measured by HPLC.

In the present context, the term "lactose has been transgalactosylated" means that a galactose molecule has been covalently linked to the lactose molecule such as for example covalently linked to any of the free hydroxyl groups in the lactose molecule or as generated by internal transgalatosylation for example forming allolactose.

In the present context, the evaluation of performance of polypeptides disclosed herein in galactooligosaccharide (GOS) production were tested in a "milk-based assay" (yogurt application mimic). Batch experiments with a volume of 100 μl were performed in 96 well MTP plates using a yogurt mix, consisting of 98.60% (w/v) fresh pasteurized low-fat milk (Arla Mini-mælk) and 1.4% (w/v) Nutrilac YQ-5075 whey ingredient (Arla). To completely hydrate Nutrilac YQ-5075 the mixture was left with agitation for 20 h and afterwards added 20 mM NaPhosphate pH 6.5 to ensure a pH of 6.5. This yogurt-base was either used plain or with various supplements such as additional lactose, fucose, maltose, xylose or salts. 90 µl of the yogurt was mixed with 10 µl purified enzyme or crude ferment, sealed with tape and incubated at 43° C. for 3 hours. The reaction was stopped by 100 µl 10% Na2CO3. Samples were stored at −20° C. Quantification of galactooligosaccharides (GOS), lactose, glucose and galactose were performed by HPLC. Analysis of samples was carried out on a Dionex ICS 3000. IC parameters were as follows: Mobile phase: 150 mM NaOH, Flow: Isochratic, 0.25 ml/min, Column: Carbopac PA1, Column temperature: RT, Injection volume: 10 µL, Detector: PAD, Integration: Manual, Sample preparation: 100 times dilution in Milli-Q water (0.1 ml sample+9.9 ml water) and filtration through 0.45 im syringe filters, Quantification: Peak areas in percent of peak area of the standard. A GOS syrup (Vivanal GOS, Friesland Campina) was used as standard for GOS quantification.

The trans-galactosylating activity can be measured by means of HPLC quantification or enzymatic assays as described in WO 2013/182686.

In the present context, the term "which polypeptide is spray-dried" means that the polypeptide has been obtained by spray-drying a polypeptide which is in solution or suspension at an appropriate temperature and for an appropriate period removing the water.

In the present context, the term "which polypeptide is in solution" relates to a polypeptide which is soluble in a solvent without precipitating out of solution. A solvent for this purpose includes any millieu in which the polypeptide may occur, such as an aqueous buffer or salt solution, a fermentation broth, or the cytoplasm of an expression host.

In the present context, the term "stabilizer" means any stabilizer for stabilizing the polypeptide e.g., a polyol such as, e.g., glycerol or propylene glycol, a sugar or a sugar alcohol, lactic acid, boric acid, or a boric acid derivative (e.g., an aromatic borate ester). In one aspect, the stabilizer is not a polyol, or the polyol is present at a level of 0.1 wt % or less.

The term "isolated" means that the polypeptide is at least substantially free from at least one other component with which the sequence is naturally associated in nature and as found in nature and/or is substantially free from cellulose, mannanose, pectinase or amylase. In one aspect, "isolated polypeptide" as used herein refers to a polypeptide which is at least 30% pure, at least 40% pure, at least 60% pure, at least 80% pure, at least 90% pure, and at least 95% pure, as determined by SDS-PAGE.

Thus the term "substantially free from cellulase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of cellulase. Herein, the term "substantially free from" can therefore be seen as being synonymous with the terms "isolated polypeptide" and "polypeptide in isolated form."

Thus the term "substantially free from mannanase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of mannanase. Herein, the term "substantially free from" can therefore be seen as being synonymous with the terms "isolated polypeptide" and "polypeptide in isolated form."

Thus the term "substantially free from pectinase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of pectinase. Herein, the term "substantially free from" can therefore be seen as being synonymous with the terms "isolated polypeptide" and "polypeptide in isolated form."

Thus the term "substantially free from amylase" means herein a preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of amylase. Herein, the term "substantially free from" can therefore be seen as being synonymous with the terms "isolated polypeptide" and "polypeptide in isolated form."

The term "substantially pure polypeptide" means herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides disclosed herein are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods. Herein, the term "substantially pure polypeptide" is synonymous with the terms "isolated polypeptide" and "polypeptide in isolated form."

The term "purified" or "pure" means that a given component is present at a high level state—e.g. at least about 51% pure, such as at least 51% pure, or at least about 75% pure such as at least 75% pure, or at least about 80% pure such as at least 80% pure, or at least about 90% pure such as at least 90% pure, or at least about 95% pure such as at least 95% pure, or at least about 98% pure such as at least 98% pure. The component is desirably the predominant active component present in a composition.

The term "microorganism" in relation to the present invention includes any "microorganism" that could comprise a nucleotide sequence according to the present invention or a nucleotide sequence encoding for a polypeptide having the specific properties as defined herein and/or products obtained therefrom. In the present context, "microorganism" may include any bacterium or fungus being able to ferment a milk substrate.

The term "host cell"—in relation to the present invention includes any cell that comprises either a nucleotide sequence encoding a polypeptide having the specific properties as defined herein or an expression vector as described above and which is used in the production of a polypeptide having the specific properties as defined herein. In one aspect, the production is recombinant production.

The term "milk", in the context of the present invention, is to be understood as the lacteal secretion obtained from any mammal, such as cows, sheep, goats, buffaloes or camels.

In the present context, the term "milk-based substrate" means any raw and/or processed milk material or a material derived from milk constituents. Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream. Preferably, the milk-based substrate is milk or an aqueous solution of skim milk powder. The milk-based substrate may be more concentrated than raw milk. In one embodiment, the milk-based substrate has a ratio of protein to lactose of at least 0.2, preferably at least 0.3, at least 0.4, at least 0.5, at least 0.6 or, most preferably, at least 0.7. The milk-based substrate may be homogenized and/or pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices.

"Pasteurizing" as used herein means reducing or eliminating the presence of live organisms, such as microorganisms, in the milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow. A "food product" or "food composition" in the context of the present invention may be any comestible food or feed product suitable for consumption by an animal or human.

A "dairy product" in the context of the present invention may be any food product wherein one of the major constituents is milk-based. Preferable, the major constituent is milk-based. More preferably, the major constituent is a milk-based substrate which has been treated with an enzyme having transgalactosylating activity.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A "fermented dairy product" in present context is to be understood as any dairy product wherein any type of fermentation forms part of the production process. Examples of fermented dairy products are products like yoghurt, buttermilk, creme fraiche, quark and fromage frais. Another example of a fermented dairy product is cheese. A fermented dairy product may be produced by any method known in the art.

The term "fermentation" means the conversion of carbohydrates into alcohols or acids through the action of a microorganism such as a starter culture. In one aspect, fermentation comprises conversion of lactose to lactic acid.

In the present context, "microorganism" may include any bacterium or fungus being able to ferment a milk substrate.

In the present context the term "Pfam domains" means regions within a protein sequence that are identified as either Pfam-A or Pfam-B based on multiple sequence alignments and the presence of Hidden Markov Motifs ("*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222.). As examples of Pfam domains mention may be made of Glyco_hydro2N (PF02837), Glyco_hydro (PF00703), Glyco_hydro 2C (PF02836) and Bacterial Ig-like domain (group 4) (PF07532).

As used herein, the term "expression" refers to the process by which a polypeptide is produced based on the nucleic acid sequence of a gene. The process includes both transcription and translation.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation. Expression may involve the use of a host organism to produce the polypeptide. A host organism, also referred to simply as a host, can include prokaryotes and eukaryotes, and may in some embodiments include bacterial and fungal species.

As used herein, "expression vector" refers to a DNA construct containing a DNA coding sequence (e.g., gene sequence) that is operably linked to one or more suitable control sequence(s) capable of affecting expression of the coding sequence in a host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the description is intended to include such other forms of expression vectors that serve equivalent functions and which are, or become, known in the art.

A "promoter" refers to a regulatory sequence that is involved in binding RNA polymerase to initiate transcription of a gene. The promoter may be an inducible promoter or a constitutive promoter. A non-limiting example of an inducible promoter which may be used is *Trichoderma reesei* cbh1, which is an inducible promoter.

The term "operably linked" refers to juxtaposition wherein the elements are in an arrangement allowing them to be functionally related. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

"Under translational control" is a term well understood in the art that indicates a regulatory process which occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "signal sequence" (also termed "presequence," "signal peptide," "leader sequence," or "leader peptide") refers to a sequence of amino acids bound to the N-terminal portion of a protein which facilitates the secretion of the mature form of the protein from the cell (e.g. SEQ ID NO: 5). The signal sequence targets the polypeptide to the secretory pathway and is cleaved from the nascent polypeptide once it is translocated in the endoplasmic reticulum membrane. The mature form of the extracellular protein (e.g. SEQ ID NO: 1) lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "culturing" refers to growing a population of microbial cells under suitable conditions for growth, in a liquid or solid culture medium. The term "culture medium" refers to the medium used in this process The term "introduced" in the context of inserting a nucleic acid sequence into a cell includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

As used herein, the terms "modification" and "alteration" are used interchangeably and mean to change or vary. In the context of modifying or altering a polypeptide, these terms may mean to change the amino acid sequence, either directly or by changing the encoding nucleic acid, or to change the structure of the polypeptide such as by glycosylating the enzyme.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989 Molecular Cloning: A Laboratory Manual); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

Unless otherwise indicated, nucleic acids are written left to right in 5' to 3' orientation; amino acid sequences are written left to right in amino to carboxy orientation, respectively.

Numeric ranges provided herein are inclusive of the numbers defining the range.

In enzyme products, small amounts of unwanted enzyme activity mainly originate from the production host and are referred to as enzyme side activity. The present invention is directed to reducing unwanted enzyme side activity. Enzyme activity in dairy applications should preferably be measured at the appropriate Ph, and temperature, for the application. In Milk pH varies from 6.4 to 6.8, Yoghurt: pH ~4, infant formula pH 5.9-7.3, mozzarella pH 5.2-5.5 and mayonnaise pH 4. Optimally, the level of undesirable activity can be determined by application tests in each intended application.

Cellulase

In one aspect the present invention relates to compositions which are free from or substantially free from cellulase activity. In another aspect the present invention provides a novel bacterium in which the gene encoding for cellulase is inactivated. Such compositions comprise a polypeptide which has transgalactosylating activity. The host cells according to the present invention are capable of expressing the polypeptide which has transgalactosylating activity. Such transgalactocylating activity should be present at such a level that GOS is capable of being produced from lactose in a product, i.e. preferably polypeptide is present in the composition or the host cell is capable of expressing it at such a level that dietary fibers in the form of GOS can be produced from lactose present in diary products to which the composition or host cell is added.

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). According to one embodiment the cellulase gene which is inactivated is bgLC endoglucanase.

Mannanase

Mannanase is an enzyme, that breaks down compounds known as mannanes. These polysaccharides are constructed from the simple sugar mannose and are found widely in nature. In many plants (and, for example, in their seeds), mannanes serve as carbohydrate reserves. In one aspect, the enzyme is selected from the group of mannanases, in particular endo-beta-mannanases, esterases, exo-mannanases, galactanases. According to one embodiment the mannase gene which is inactivated is gmuG mannanase.

Pectinase

Pectinase is an enzyme that breaks down pectin, a polysaccharide found in plant cell walls. Commonly referred to as pectic enzymes, they include pectolyase, pectozyme and polygalacturonase. One of the most studied and widely used commercial pectinases is polygalacturonase. According to one embodiment the pectinase gene which is inactivated is pel pectate lyase.

Amylase

Amylase is an enzyme that catalyses the hydrolysis of starch into sugars. Amylase is present in the saliva of humans and some other mammals, where it begins the chemical process of digestion. The pancreas and salivary gland make amylase (alpha amylase) to hydrolyse dietary starch into disaccharides and trisaccharides which are converted by other enzymes to glucose to supply the body with energy. Plants and some bacteria also produce amylase. Specific amylase proteins are designated by different Greek letters. All amylases are glycoside hydrolases and act on α-1,4-glycosidic bonds. The present invention preferably additional involves the inactivation of (EC 3.2.1.1) (CAS #9014-71-5) (alternate names: 1,4-α-D-glucan glucanohydrolase; glycogenase). According to one embodiment the amylase gene which is inactivated is amyE alpha-amylase.

In one aspect, the term "amylase" as used herein refers to amylases such as [alpha]-amylases (EC 3.2.1.1), [beta]-amylases (EC 3.2.1.2) and [gamma]-amylases (EC 3.2.1.3.).

Degree of Identity

The relatedness between two amino acid sequences or between two nucleotide sequences is described by the parameter "identity".

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the reference sequence.

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the longest of the two sequences.

In another embodiment, the degree of sequence identity between the query sequence and the reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the "alignment length", where the alignment length is the length of the entire alignment including gaps and overhanging parts of the sequences.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score),
ii) assignment of a penalty score each time an existing gap is extended with an extra position (extension penalty score),
iii) assignment of high scores upon alignment of identical amino acids, and
iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at www.ncbi.nlm.nih.gov and which was firstly described in Altschul et al. (1990) J. Mol. Biol. 215; 403-410.

In a preferred embodiment of the present invention, the alignment program is performing a global alignment program, which optimizes the alignment over the full-length of the sequences. In a further preferred embodiment, the global alignment program is based on the Needleman-Wunsch algorithm (Needleman, Saul B.; and Wunsch, Christian D. (1970), "A general method applicable to the search for similarities in the amino acid sequence of two proteins", Journal of Molecular Biology 48 (3): 443-53). Examples of current programs performing global alignments using the Needleman-Wunsch algorithm are EMBOSS Needle and EMBOSS Stretcher programs, which are both available at www.ebi.ac.uk/Tools/psa.

EMBOSS Needle performs an optimal global sequence alignment using the Needleman-Wunsch alignment algorithm to find the optimum alignment (including gaps) of two sequences along their entire length.

EMBOSS Stretcher uses a modification of the Needleman-Wunsch algorithm that allows larger sequences to be globally aligned.

In one embodiment, the sequences are aligned by a global alignment program and the sequence identity is calculated by identifying the number of exact matches identified by the program divided by the "alignment length", where the alignment length is the length of the entire alignment including gaps and overhanging parts of the sequences.

In a further embodiment, the global alignment program uses the Needleman-Wunsch algorithm and the sequence identity is calculated by identifying the number of exact matches identified by the program divided by the "alignment length", where the alignment length is the length of the entire alignment including gaps and overhanging parts of the sequences.

In yet a further embodiment, the global alignment program is selected from the group consisting of EMBOSS Needle and EMBOSS stretcher and the sequence identity is calculated by identifying the number of exact matches identified by the program divided by the "alignment length", where the alignment length is the length of the entire alignment including gaps and overhanging parts of the sequences.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:

Gap opening penalty: 10
Gap extension penalty: 0.05
Gap separation penalty range: 8

In a another embodiment, the alignment of one amino acid sequence with, or to, another amino acid sequence is determined by the use of the score matrix: blosum62mt2 and the VectorNTI Pair wise alignment settings

| | | |
|---|---|---|
| Settings | K-tuple | 1 |
| | Number of best diagonals | 5 |
| | Window size | 5 |
| | Gap Penalty | 3 |
| | Gap opening Penalty | 10 |
| | Gap extension Penalty | 0.1 |

In one embodiment, the percentage of identity of one amino acid sequence with, or to, another amino acid sequence is determined by the use of Blast with a word size of 3 and with BLOSUM 62 as the substitution matrix having transgalactosylating activity.

Polypeptide

In one aspect, the invention disclosed herein employs a polypeptide having a ratio of transgalactosylating activity: β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In one aspect, the invention disclosed herein employs a polypeptide, wherein the glycoside hydrolase catalytic core has an amino acid sequence of SEQ ID NO:7.

In one aspect, the invention disclosed herein employs a polypeptide containing a Glyco_hydro2N (PF02837), a Glyco_hydro (PF00703) and/or a Glyco_hydro 2C (PF02836) domains.

In one aspect, disclosed herein is a polypeptide containing the Bacterial Ig-like domain (group 4) (PF07532).

In one aspect, disclosed herein is a polypeptide having transgalactosylating activity selected from the group consisting of:

g. a polypeptide comprising an amino acid sequence having at least 90% sequence identity with SEQ ID NO: 1, wherein said polypeptide consists of at most 980 amino acid residues, h. a polypeptide comprising an amino acid sequence having at least 97% sequence identity with SEQ ID NO: 2, wherein said polypeptide consists of at most 975 amino acid residues, i. a polypeptide comprising an amino acid sequence having at least 96.5% sequence identity with SEQ ID NO: 3, wherein said polypeptide consists of at most 1300 amino acid residues, j. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i), k. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and l. a polypeptide comprising a deletion, insertion and/or conservative substitution of one or more amino acid residues of SEQ ID NO: 1, 2, 3, 4 or 5.

In another aspect, the invention disclosed herein employs a polypeptide having transgalactosylating activity selected from the group consisting of:
a. a polypeptide comprising an amino acid sequence having at least 96.5% sequence identity with SEQ ID NO: 3, wherein said polypeptide consists of at most 1300 amino acid residues,
b. a polypeptide comprising an amino acid sequence having at least 90% sequence identity with SEQ ID NO: 1, wherein said polypeptide consists of at most 980 amino acid residues,
c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
e. a polypeptide comprising a deletion, insertion and/or conservative substitution of one or more amino acid residues of SEQ ID NO: 1, 2, 3, 4 or 5.

In one aspect, of the invention disclosed herein employs a polypeptide, wherein the amino acid sequence has at least 68%, 70%, 72%, 74%, 76%, 78%, 80%%, 85%, 90%, 91%, 92%, 93%, 94%, 95%, 96%, 97%, 98%, or 99%, sequence identity to the mature amino acid sequence of SEQ ID NO: 1, 2, 3, 4 or 5.

In one aspect, of the invention disclosed herein employs a polypeptide having 90% sequence identity to the mature amino acid sequence of SEQ ID NO:1.

In one aspect, of the invention disclosed herein employs a polypeptide having 90% sequence identity to the mature amino acid sequence of SEQ ID NO:2.

In one aspect, of the invention disclosed herein employs a polypeptide having 96.5% sequence identity to the mature amino acid sequence of SEQ ID NO:3.

In one aspect, of the invention disclosed herein employs a polypeptide having 96.5% sequence identity to the mature amino acid sequence of SEQ ID NO:4.

In one aspect, of the invention disclosed herein employs a polypeptide having 96.5% sequence identity to the mature amino acid sequence of SEQ ID NO:5.

In one aspect, of the invention disclosed herein employs a polypeptide comprising or consisting of the amino acid sequence of SEQ ID NO:1, 2, 3, 4 or 5.

In one aspect, of the invention disclosed herein employs a polypeptide, which is derived from *Bifidobacterium bifidum*.

In one aspect, of the invention disclosed herein employs a polypeptide having a pH optimum of 6.5-7.5.

In one aspect, of the invention disclosed herein employs a polypeptide having a temperature optimum of 30-60 such as 42-60 degree celcius.

Polypeptides having activity on carbohydrates can be classified using either the IUBMB system of classification based on their substrate specificity or on the CaZy assignment into one of the current 125 glycoside hydrolase family. In the CaZy database the assignment is based on both sequence and structural information combined with knowledge of stereochemistry of the substrates and products.

Disclosed herein is the use of polypeptides which when being an expression product in a suitable host strain (e.g. *Bacillus subtilis*) comprising of a nucleic acid sequence, which encodes said polypeptide, is the only polypeptide expression product of said nucleic acid sequence that exhibits transgalactosylating activity. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometic scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity) *100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

The polypeptide disclosed herein comprises at least two separate functional domains contained within the enzyme. Firstly, the polypeptide should contain a glycoside hydrolase catalytic core as described in the following. The catalytic core should belong to the GH-A clan of related glycoside hydrolase families. The GH-A clan is characterized by cleaving glycosidic bonds via a retaining mechanism and possesses a catalytic domain which is based on a TIM barrel fold (Wierenga, 2001, FEBS Letters, 492(3), p 193-8). The catalytic domain contains two glutamic acid residues which act as proton donor and nucleophile, eminating from strands 4 and 7 of the barrel domain (Jenkins, 1995, FEBS Letters, 362(3), p 281-5). The overall structure of the TIM barrel is a $(\beta/\alpha)$ 8 fold consisting of 8 beta strands and 8 alpha-helices. In one aspect, the glycoside hydrolase catalytic core disclosed herein belong to either of the glycoside hydrolase families GH-2, and -35 which are all TIM-barrel enzymes belonging to the GH-A clan. In a further aspect, the glycoside hydrolase catalytic core belong to family GH-2 or GH-35. In a further aspect, the glycoside hydrolase catalytic core belong to family GH-2. A common denominator is that these enzymes are so called retaining enzymes, so that the stereochemistry of the substrate is conserved in the product (Henrissat, 1997, Curr Opin Struct Biol, 7(5), 637-44).

In one aspect, the polypeptides disclosed herein have activity on carbohydrates bonds which has the $\beta(1\to 4)$ conformation. This effectively put the enzymes into the IUBMB EC 3.2.1.23 class of β-galactosidases. This activity may be, but is not confined to, determined by utilizing synthetic substrates such as para-nitrophenol-β-D-galactopyranoside (PNPG), ortho-nitrophenol-β-D-galactopyranoside (ONPG) or β-D-galactopyranoside with chromogenic aglycons (XGal). As an alternative way of determining whether an enzyme belong to the EC 3.2.1.23 class of β-galactosidases is to incubate with a substrate such as lactose and measure the release of glucose by a method such as enzymatic determination, HPLC, TLC or other methods known to persons skilled in the art.

In order to predict functional entities of polypeptides several available public repositories can be applied such as for example Pfam (Nucl. Acids Res. (2010) 38 (suppl 1): D211-D222. doi: 10.1093/nar/gkp985) and Interpro (Nucl. Acids Res. (2009) 37 (suppl 1): D211-D215. doi: 10.1093/nar/gkn785). It should be specified that when performing such analysis the analysis should be performed on the full length sequence of the polypeptide available from public repository databases.

In a further aspect, a polypeptide containing one or more Pfam domains selected from: Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Pfam domains Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Glyco_hydro2N (PF02837), Glyco_hydro (PF00703), and Glyco_hydro 2C (PF02836) domains which constitutes the catalytic domain of the polypeptide, is used.

In a further aspect, a polypeptide as disclosed herein and having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, is used. In a further aspect, the polypeptide is derived from *Bifidobacterium bifidum*.

In one aspect, the herein disclosed polypeptide(s) has a transgalactosylating activity such that more than 20%, more than 30%, more than 40%, up to 50% of the initial lactose is transgalactosylated as measured at a concentration of 100 ppm in a milk-based assay at 37° C. and 5 w/w % lactose after 15, 30 or 180 such as 180 minutes of reaction.

In a further aspect, the herein disclosed polypeptide(s) has a β-galactosidase activity such that less than 80%, less than 70%, less than 60%, less than 50%, less than 40%, less than 30%, less than 20% of the lactose has been hydrolysed as measured at a concentration of 100 ppm in a milk-based assay at 37° C. and 5 w/w % lactose after 15, 30 or 180 such as 180 minutes of reaction.

In one aspect, the β-galactosidase activity and/or the transgalactosylating activity are measured at a concentration of 100 ppm corresponding to 2.13 LAU as specified in method 4. In general terms the units of activity of the enzyme may be measured according to the assay disclosed in WO 2003/186286 as Method 4 and reproduced below in the Example section 4.

In a further aspect, the herein disclosed polypeptide(s) has one or more of the following characteristics:

a) a ratio of transgalactosylating activity:β-galactosidase activity of at least of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, and/or b) has a transgalactosylating activity such that more than 20%, more than 30%, more than 40%, and up to 50% of the initial lactose has been transgalactosylated as measured at a concentration of 100 ppm in a milk-based assay at 37° C. and 5 w/w % lactose after 15, 30 or 180 such as 180 minutes of reaction.

In one aspect, a polypeptide comprising an amino acid sequence having at least 96.5% sequence identity with SEQ ID NO: 3, wherein said polypeptide consists of at most 1300 amino acid residues, is provided. In a further aspect, a polypeptide comprising an amino acid sequence having at least 90% sequence identity with SEQ ID NO: 1 such as wherein said sequence identity is at least 95%, such as, e.g. at least 96%, at least 97%, at least 98%, at least 99% or at least 100% sequence identity, and wherein said polypeptide consists of at most 980 amino acid residues, is provided. In a further aspect, a polypeptide comprising an amino acid sequence having at least 90% sequence identity with SEQ ID NO: 1, wherein said polypeptide consists of at most 980 amino acid residues, is provided. In yet a further aspect, a polypeptide wherein said polypeptide has at least 90% sequence identity with SEQ ID NO: 1, such as wherein said polypeptide has at least 90%, such as, e.g. at least 91%, at least 92%, at least 93%, at least 94%, at least 95%, at least 96%, at least 97%, at least 98%, or at least 99% sequence identity with SEQ ID NO: 1 is provided. In another aspect, a polypeptide having at least 96.5% sequence identity to SEQ ID NO: 2 such as wherein said polypeptide has at least 97%, such as, e.g. at least 98% or at least 99% sequence identity with SEQ ID NO: 2. In one aspect, the polypeptides disclosed herein consist of at the most 975 amino acid residues, such as, e.g. at most 970 amino acid residues, such as at most 950 amino acid residues, such as at most 940 amino acid residues, at most 930 amino acid residues, at most 920 amino acid residues, at most 910 amino acid residues, at most 900 amino acid residues, at most 895 amino acid residues or at most 890 amino acid residues, is provided. In one aspect, a particular polypeptide consists of 887 or 965 amino acid residues, is provided. In one aspect, a polypeptide comprising an amino acid sequence having at least 97% sequence identity with SEQ ID NO: 2 such as wherein said sequence identity is at least 98%, such as, e.g. at least 99% or at least 100% sequence identity, wherein said polypeptide consists of at most 975 amino acid residues, such as, e.g. at most 970 or at least 965 amino acid residues, is provided. In one aspect, a polypeptide comprising an amino acid sequence having at least 97% sequence identity with SEQ ID NO: 2, wherein said polypeptide consists of at most 975 amino acid residues, is used.

In a further preferred aspect, a polypeptide which comprises SEQ ID NO: 1, 2, 3, 4 or 5, is provided. In yet a preferred aspect, a polypeptide consisting of the amino acid sequence of SEQ ID NO: 1, 2, 3, 4, or 5, especially a polypeptide consisting of the amino acid sequence of SEQ ID NO: 1 or 2, is used.

In a further aspect, a polypeptide comprising an amino acid sequence having at least 96.5% sequence identity with SEQ ID NO: 3 such as wherein said sequence identity is at least 97%, such as, e.g. at least 98%, at least 99% or at least 100% sequence identity, wherein said polypeptide consists of at most 1300 amino acid residues, is used.

In a further aspect, a polypeptide wherein said polypeptide has at least 98.5%, such as at least 99% or at least 99.5% sequence identity with SEQ ID NO: 5, is provided. In one aspect, such a polypeptide consists of at most 1290 amino acid residues, such as, e.g. at most 1280, at most 1270, at most 1260, at most 1250, at most 1240, at most 1230, at most 1220 or at most 1215 amino acid residues, is provided. In a preferred aspect, a polypeptide which consists of 1211 amino acid residues, is used.

In a further aspect, a polypeptide wherein said polypeptide has at least 96% such as at least at least 97%, such as, e.g., at least 98% or at least 99% sequence identity with SEQ ID NO: 4, is provided. In one aspect, a polypeptide which consists of at most 1210 amino acid residues, such as, e.g. at most 1200, at most 1190, at most 1180, at most 1170, at most 1160, at most 1150 or at most 1145 amino acid residues, such as 1142 amino acid residues, is used.

In a further aspect, a polypeptide wherein said polypeptide has at least 96.5% such as at least 97%, such as, e.g., at least 98% or at least 99% sequence identity with SEQ ID NO: 3, is provided. In one aspect, a polypeptide which consists of at most 1130 amino acid residues, such as, e.g. at the most 1120, at the most 1110, at the most 1100, at the most 1090, at the most 1080, at the most 1070, at the most 1060, at the most 1050, at the most 1055 or at the most 1040 amino acid residues, is provided. In a preferred aspect, a polypeptide which consists of 1038 amino acid residues, is used.

In a further aspect, the polypeptides disclosed herein has a ratio of transgalactosylation activity above 100% such as above 150%, 175% or 200%.

Proteins are generally comprised of one or more functional regions, commonly termed domains. The presence of different domains in varying combinations in different proteins gives rise to the diverse repertoire of proteins found in nature. One way of describing the domains are by the help of the Pfam database which is a large collection of protein domain families as described in "*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222. Each family is represented by multiple sequence alignments and hidden Markov models (HMMs). The herein provided polypeptide(s) preferably contain one or more of the Pfam domains Glyco_hydro2N (PF02837), Glyco_hydro (PF00703), Glyco_hydro 2C (PF02836) and Bacterial Ig-like domain (group 4) (PF07532). In one aspect, the herein provided polypeptide(s) contains Glyco_hydro2N (PF02837), Glyco_hydro (PF00703), Glyco_hydro 2C (PF02836) and Bacterial Ig-like domain (group 4) (PF07532).

In one aspect, the polypeptides used herein have useful transgalactosylating activity over a range of pH of 4-9, such as 5-8, such as 5.5-7.5, such as 6.5-7.5.

The present invention encompasses the use of polypeptides having a certain degree of sequence identity or sequence homology with amino acid sequence(s) defined herein or with a polypeptide having the specific properties defined herein. The present invention encompasses, in particular, the use of peptides having a degree of sequence identity with any one of SEQ ID NO: 1, 2, 3, 4 or 5, defined below, or homologues thereof.

The homologous amino acid sequence and/or nucleotide sequence should provide and/or encode a polypeptide which retains the functional transgalactosylating activity and/or enhances the transgalactosylating activity compared to a polypeptide of SEQ ID NO: 1, 2, 3, 4 or 5.

In the present context, a homologous sequence is taken to include an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Thus, the present invention also encompasses the use of variants, homologues and derivatives of any amino acid sequence of a protein or polypeptide as defined herein, particularly those of SEQ ID NO: 1, 2, 3, 4 or 5 defined below.

The sequences, particularly those of variants, homologues and derivatives of SEQ ID NO: 1, 2, 3, 4 or 5 defined below, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

In one aspect, the polypeptide sequence used in the present invention is in a purified form.

In one aspect, the polypeptide or protein for use in the present invention is in an isolated form.

In one aspect, the polypeptide of the present invention is recombinantly produced.

The variant polypeptides include a polypeptide having a certain percent, e.g., at least 90%, 91%, 92%, 93%, 94%, 95%, 96%, 97%, 98%, or 99%, of sequence identity with SEQ ID NO: 1 or 2.

The variant polypeptides include a polypeptide having a certain percent, e.g., at least 96%, 97%, 98%, or 99%, of sequence identity with SEQ ID NO: 3, 4 or 5.

In one aspect, the polypeptides employed herein comprises an amino acid sequence having at least 90%, 91%, 92%, 93%, 94%, 95%, 96%, 97%, 98%, or 99% sequence identity to the amino acid sequence of the mature polypeptide encoded by the nucleotide sequence encoding the transgalatosylase contained in *Bifidobacterium bifidum* DSM20215 shown herein as SEQ ID NO: 22. All considerations and limitations relating to sequence identities and functionality discussed in terms of the SEQ ID NO: 1, 2, 3, 4 or 5 apply mutatis mutandis to sequence identities and functionality of these polypeptides and nucleotides.

In one aspect, the subject amino acid sequence is SEQ ID NO: 1, 2, 3, 4 or 5, and the subject nucleotide sequence preferably is SEQ ID NO: 9, 10, 11, 12 or 13.

In one aspect, the polypeptide is a fragment having one or more (several) amino acids deleted from the amino and/or carboxyl terminus of the polypeptide of SEQ ID NO: 1, 2, 3, 4 or 5; wherein the fragment has transgalactosylating activity.

In one aspect, a fragment contains at least 500, 550, 600, 650, 700, 750, 800, 850, 900, 950, or 1000 amino acid residues.

In a further aspect, the length of the polypeptide variant is 500 to 1300 amino acid residues. In a further aspect, the length of the polypeptide variant is 600 to 1300 amino acids. In a further aspect, the length of the polypeptide variant is 700 to 1300 amino acids. In a further aspect, the length of the polypeptide variant is 800 to 1300 amino acids. In a further aspect, the length of the polypeptide variant is 800 to 1300 amino acids.

To evaluate the expression of a variant in a host cell, assays can measure the expressed protein, corresponding mRNA, or β-galactosidase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the variant include, but are not limited to, ONPG based assays or determining glucose in reaction mixtures such for example described in the methods and examples herein.

Polypeptide Variants of SEQ ID NO: 1, 2, 3, 4 or 5

In one aspect, a variant of SEQ ID NO: 1, 2, 3, 4 or 5 having a substitution at one or more positions which effects an altered property such as improved transgalactosylation, relative to SEQ ID NO: 1, 2, 3, 4 or 5, is used. Such variant polypeptides are also referred to in this document for convenience as "variant polypeptide", "polypeptide variant" or "variant". In one aspect, the polypeptides as defined herein have an improved transgalactosylating activity as compared to the polypeptide of SEQ ID NO: 1, 2, 3, 4 or 5. In another aspect, the polypeptides as defined herein have an improved reaction velocity as compared to the polypeptide of SEQ ID NO: 1, 2, 3, 4 or 5.

The polypeptides and the variant polypeptides used herein comprise transgalactosylation activity.

In one aspect, the ratio of transgalactosylating activity:β-galactosidase activity is at least 0.5, such as at least 1, such as at least 1.5, or such as at least 2 after 30 min. reaction such as above a concentration of 3% w/w initial lactose concentration.

In one aspect, the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction such as above a concentration of 3% w/w initial lactose concentration.

In one aspect, the polypeptides and the variants as defined herein are derivable from microbial sources, in particular from a filamentous fungus or yeast, or from a bacterium. The enzyme may, e.g., be derived from a strain of *Agaricus*, e.g. *A. bisporus*; *Ascovaginospora*; *Aspergillus*, e.g. *A. niger*, *A. awamori*, *A. foetidus*, *A. japonicus*, *A. oryzae*; *Candida*; *Chaetomium*; *Chaetotomastia*; *Dictyostelium*, e.g. *D. discoideum*; *Kluveromyces*, e.g. *K. fragilis*, *K. lactis*; *Mucor*, e.g. *M. javanicus*, *M. mucedo*, *M. subtilissimus*; *Neurospora*, e.g. *N. crassa*; *Rhizomucor*, e.g. *R. pusillus*; *Rhizopus*, e.g. *R. arrhizus*, *R. japonicus*, *R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans*, *B. circulans*, *B. megaterium*, *B. novalis*, *B. subtilis*, *B. pumilus*, *B. stearothermophilus*, *B. thuringiensis*; *Bifidobacterium*, e.g. *B. longum*, *B. bifidum*, *B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes*, *E. cloacae* *Edwardsiella*, *E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus*, *Pycnoporus sanguineus*; *Ruminococcus*, e.g. *R. torques*; *Salmonella*, e.g. *S. typhimurium*; *Serratia*, e.g. *S. liquefasciens*, *S. marcescens*; *Shigella*, e.g. *S. flexneri*; *Streptomyces*, e.g. *S. antibioticus*, *S. castaneoglobisporus*, *S. violeceoruber*; *Trametes*; *Trichoderma*, e.g. *T. reesei*, *T. viride*; *Yersinia*, e.g. *Y. enterocolitica*.

An isolated and/or purified polypeptide comprising a polypeptide or a variant polypeptide as defined herein is provided. In one embodiment, the variant polypeptide is a mature form of the polypeptide (SEQ ID NO: 1, 2, 3, 4 or 5). In one aspect, the variants include a C-terminal domain.

In one aspect, a variant polypeptide as defined herein includes variants wherein between one and about 25 amino acid residues have been added or deleted with respect to SEQ ID NO: 1, 2, 3, 4 or 5. In one aspect, a variant polypeptide as defined herein includes variants wherein between one and 25 amino acid residues have been substituted, added or deleted with respect to SEQ ID NO: 1, 2, 3, 4 or 5. In one aspect, the variant has the amino acid sequence of SEQ ID NO: 1, 2, 3, 4 or 5, wherein any number between one and about 25 amino acids have been substituted. In a further aspect, the variant has the amino acid sequence of SEQ ID NO: 1, 2, 3, 4 or 5, wherein any number between three and twelve amino acids has been substituted. In a further aspect, the variant has the amino acid sequence of SEQ ID NO: 1, 2, 3, 4 or 5, wherein any number between five and nine amino acids has been substituted.

In one aspect, at least two, in another aspect at least three, and yet in another aspect at least five amino acids of SEQ ID NO: 1, 2, 3, 4 or 5 have been substituted.

In one aspect, the herein disclosed polypeptide(s) has the sequence of 1, 2, 3, 4 or 5.

In one aspect, the herein disclosed polypeptide(s) has the sequence of SEQ ID NO: 1, 2, 3, 4 or 5, wherein the 10, such as 9, such as 8, such as 7, such as 6, such 5, such as 4, such as 3, such as 2, such as 1 amino acid in the N-terminal end are substituted and/or deleted.

Enzymes and enzyme variants thereof can be characterized by their nucleic acid and primary polypeptide sequences, by three dimensional structural modeling, and/or by their specific activity. Additional characteristics of the polypeptide or polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1, 2, 3, 4 or 5, such as improved stability at high temperatures, e.g., 65-85° C.

A polypeptide variant is provided as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5.

Nucleotides

In one aspect, the present invention employs isolated polypeptides having transgalactosylating activity as stated above which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with i) the nucleic acid sequence comprised in SEQ ID NO: 9, 10, 11, 12 or 13 encoding the mature polypeptide of SEQ ID NO: 1, 2, 3, 4 or 5; ii) the cDNA sequence of i) or iii) the complementary strand of i) or ii), (J. Sambrook, E. F. Fritsch, and T. Maniatis, 1989, Molecular Cloning, A Laboratory Manual, 2d edition, Cold Spring Harbor, N.Y.). A subsequence of SEQ ID NO: 9, 10, 11, 12 or 13 contains at least 100 contiguous nucleotides or preferably at least 200 contiguous nucleotides. Moreover, the subsequence may encode a polypeptide fragment which has lactase activity.

The nucleotide sequence of SEQ ID NO: 9, 10, 11, 12 or 13 or a subsequence thereof, as well as the amino acid sequence of SEQ ID NO: 1, 2, 3, 4 or 5 or a fragment thereof, may be used to design a nucleic acid probe to identify and clone DNA encoding polypeptides having transgalactosylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, 10, 11, 12 or 13 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 9, 10, 11, 12 or 13, its complementary strand, or a subsequence thereof, under very low to very high stringency conditions. Molecules to which the nucleic acid probe hybridizes under these conditions can be detected using X-ray film.

The nucleic acid probe may be the mature polypeptide coding region of SEQ ID NO: 9, 10, 11, 12 or 13.

For long probes of at least 100 nucleotides in length, very low to very high stringency conditions are defined as prehybridization and hybridization at 42° C. in 5×SSPE, 0.3% SDS, 200 g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

Effective $T_m=81.5+16.6(\log M[Na^+])+0.41(\% G+C)-0.72(\%$ formamide)

(See www.ndsu.nodak.edu/instruct/mcclean/plsc731/dna/dna6.htm)

The G+C content of SEQ ID NO: 10 is 42% and the G+C content of SEQ ID NO: 11 is 44%. For medium stringency, the formamide is 35% and the Na$^+$ concentration for 5×SSPE is 0.75 M.

Another relevant relationship is that a 1% mismatch of two DNAs lowers the $T_m$ by 1.4° C. To determine the degree of identity required for two DNAs to hybridize under medium stringency conditions at 42° C., the following formula is used:

% Homology=100−[(Effective $T_m$−Hybridization Temperature)/1.4]

(See www.ndsu.nodak.edu/instruct/mcclean/plsc731/dna/dna6.htm)

The variant nucleic acids include a polynucleotide having a certain percent, e.g., 60%, 65%, 70%, 75%, 80%, 85%, 90%, 95%, or 99%, of sequence identity with the nucleic acid encoding SEQ ID NO: 1, 2, 3, 4 or 5. In one aspect, a nucleic acid capable of encoding a polypeptide as disclosed herein, is provided. In a further aspect, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 9, 10, 11, 12 or 13.

A plasmid comprising a nucleic acid as described herein may be used.

An expression vector comprising a nucleic acid as described herein, or capable of expressing a polypeptide as described herein may be used.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

The polypeptide variants as provided herein may be produced synthetically or through recombinant expression in a host cell, according to procedures well known in the art. In one aspect, the herein disclosed polypeptide(s) is recombinant polypeptide(s). The expressed polypeptide variant as defined herein optionally is isolated prior to use.

In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

A nucleic acid sequence is provided encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Vectors

In one aspect, the invention employs a vector comprising a polynucleotide. In one aspect, a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, 3$^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in E. coli, and pE194, for example, which permits replication in Bacillus.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when P. saccharophila is the host, the promoter is a native P. saccharophila promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. In another aspect, a representative signal peptide is SEQ ID NO: 27. A representative signal peptide is SEQ ID NO: 9 which is the native signal sequence of the Bacillus subtilis aprE precursor. In other embodiments, the DNA encoding the signal sequence is replaced with a nucleotide sequence encoding a signal sequence from other extra-cellular Bacillus subtilis pre-cursors. In one embodiment, the polynucleotide that encodes the signal sequence is immediately upstream and in-frame of the polynucleotide that encodes the polypeptide. The signal sequence may be selected from the same species as the host cell.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an A. nidulans amdS gene as a selective marker is described in Kelley et al., EMBO J. 4: 475-479 (1985) and Penttila et al., Gene 61: 155-164 (1987).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences to leave the domain to be expressed under control of its own transcriptional and translational regulatory sequences. The second type of expression vector is preassembled and contains sequences required for high-level transcription and a selectable marker. In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Expression Hosts/Host Cells

In a further aspect, a host cell comprising, preferably transformed with, a plasmid as described herein or an expression vector as described herein, is used.

In a further aspect, a cell capable of expressing a polypeptide as described herein, is used.

In one aspect, the host cell as described herein, or the cell as described herein is a bacterial, fungal or yeast cell.

In a further aspect, the host cell is selected from the group consisting of Ruminococcus, *Bifidobacterium, Lactococcus, Lactobacillus, Streptococcus, Leuconostoc, Escherichia, Bacillus, Streptomyces, Saccharomyces, Kluyveromyces, Candida, Torula, Torulopsis* and *Aspergillus*.

In a further aspect, the host cell cell is selected from the group consisting of *Ruminococcus hansenii, Bifidobacterium breve, Bifidobacterium longum, Bifidobacterium infantis, Bifidobacterium bifidum* and *Lactococcus lactis*.

In another embodiment, suitable host cells include a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans,* or *S. murinus*; or a Gram negative bacterium, wherein said Gram negative bacterium is *Escherichia coli* or a *Pseudomonas* species. In one aspect, the host cell is a *B. subtilus* or *B. licheniformis*. In one embodiment, the host cell is *B. subtilis*, and the expressed protein is engineered to comprise a *B. subtilis* signal sequence, as set forth in further detail below.

In some embodiments, a host cell is genetically engineered to express a polypeptide variant as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5. In some embodiments, the polynucleotide encoding a polypeptide variant as defined herein will have a nucleic acid sequence encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Mutagenesis

A cellulase, mannanase and pectinase, and optionally amylase, deficient host cell or a host cell in which these enzymes are essentially inactive may be obtained by genetic engineering using recombinant genetic manipulation techniques, submitting the host to mutagenesis, or both. Modification or inactivation of the genes coding for cellulase, mannanase and pectinase, and optionally amylase, of the present invention may result from subjecting the parent cell to mutagenesis and selecting for mutant cells in which the ability to express these enzymes has been reduced by comparison to the parental cell. The mutagenesis, which may be specific or random, may be performed, for example, by use of a suitable physical or chemical mutagenizing agent, by use of a suitable oligonucleotide, or by subjecting the DNA sequence to PCR-generated mutagenesis. Furthermore, the mutagenesis may be performed by use of any combination of these mutagenizing agents.

Examples of a physical or chemical mutagenizing agent suitable for the present purpose include gamma or ultraviolet (UV) radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogs. When such agents are used, the mutagenesis is typically performed by incubating the parent cell to be mutagenized in the presence of the mutagenizing agent of choice under suitable conditions, and selecting for mutant cells exhibiting reduced expression of the gene. Alternatively, such strains may be isolated using genetic techniques such as hybridization or mating, and protoplast fusion or any other classical genetic technique to induce genetic diversity. The cellulase, mannanase and pectinase, and optionally amylase, deficient strain obtained may be subsequently selected by monitoring the expression level of the enzymes. Optionally, the cellulase, mannanase and pectinase, and optionally amylase, deficient strain is subsequently selected by measuring the expression level of a given gene of interest to be expressed in the host cell. Selection of strains having reduced enzyme activity may be done by directly measuring the enzyme activity in culture broth, in culture supernatant, in permeabilized cells, or in cell lysate.

Recombinant DNA Techniques

Alternatively, host cells that have a reduced amount of cellulase, mannanase and pectinase, and optionally amylase activity or a host cell in which these enzymes are essentially inactive may be constructed using recombinant DNA technology. Several techniques for gene inactivation or gene disruption are described in the art, such as one-step gene disruption, marker insertion, site directed mutagenesis, deletion, RNA interference, anti-sense RNA, and others, and may all be used to lower, inhibit or disturb the synthesis of the cellulase, mannanase and pectinase, and optionally amylase activity in order to obtain a industrial production strain with decreased cellulase, mannanase and pectinase, and optionally amylase, activity. Also the inactivation of cellulase, mannanase and pectinase, and optionally amylase by altering the control sequence(s) directing the expression of the cellulase, mannanase and pectinase, and optionally amylase gene are part of the present invention. An example thereof is the lowering of the promoter activity by gene disruption.

Using modern genetic modification techniques, one can obtain a recombinant cellulase, mannanase and pectinase, and optionally amylase, deficient strain, preferably by disturbing a gene coding for cellulase, mannanase and pectinase, and optionally amylase activity, more preferably by inserting a marker gene into a gene coding for the enzyme activity, most preferably by removal of part or all of the enzyme coding region from the genome. Methods to perform such gene inactivations have been described for many different micro-organisms and are known to those skilled in the art (see i.e. EP357127). Expression of cellulase, mannanase and pectinase, and optionally amylase in the mutant cell may thereby be reduced or eliminated. Dependent on the host strain that is modified using these techniques, the procedure may be repeated several times to remove all or most of the cellulase, mannanase and pectinase, and optionally amylase coding sequences.

Modification or inactivation of host genes such as cellulase, mannanase and pectinase, and optionally amylase may be performed by established antisense techniques using a nucleotide sequence complementary to the nucleotide sequence of the gene. More specifically, expression of the gene may be reduced or eliminated by introducing a nucleotide sequence complementary to the nucleotide sequence, which may be transcribed in the cell and is capable of hybridizing to the mRNA produced in the cell. Under conditions allowing the complementary antisense nucleotide sequence to hybridize to the mRNA, the amount of protein translated is thus reduced or eliminated. Examples of expressing an antisense RNA is provided by Ngiam et al. (*Appl. Environ. Microbiol.* 66:775-782, 2000) and Zrenner et al. (*Planta* 190:247-252, 1993).

Modification, downregulation, or inactivation of a host gene may be obtained via RNA interference (RNAi) techniques (*FEMS Microb. Lett.* 237:317-324, 2004). More specifically, expression of the gene by a filamentous fungal cell may be reduced or eliminated by cloning identical sense and antisense portions of the nucleotide sequence, which expression is to be affected, behind each other with a nucleotide spacer in between, inserting into an expression vector, and introducing the expression vector into the cell where double-stranded RNA (dsRNA) may be transcribed and then processed to shorter siRNA that is able to hybridize to target mRNA. After dsRNA is transcribed, formation of small (21-23) nucleotide siRNA fragments will lead to a targeted degradation of the mRNA, which is to be affected. The elimination of the specific mRNA can be to various extents. The RNA interference techniques described in WO 2005/05672 and WO 2005/026356 may be used for modification, downregulation, or inactivation of the host gene.

The cellulase, mannanase and pectinase, and optionally amylase, deficient host cell, which has been modified or inactivated by any of the methods described above and produces fewer cellulase, mannanase and pectinase, and optionally amylase, activity than the parent cell when cultured under identical conditions as measured using the same assays as defined before, may harbor another nucleotide sequence.

Such industrial production strains with decreased cellulase, mannanase and pectinase, and optionally amylase, activity isolated or constructed by classical genetic techniques or recombinant DNA technology may be used for relevant industrial processes that require the final product to contain dietary fibers. Preferably these strains are used for the production of the industrially relevant enzyme having transgalactosylating activity. More preferably these strains are used for the production of enzymes that are used in the food industry, even more preferably these enzymes are used in processing of dairy products. Most preferably such industrial production strains with decreased cellulase, mannanase and pectinase, and optionally amylase, activity are used for the production of GOS from lactose.

Preferably, the cellulase, mannanase and pectinase, and optionally amylase, deficient host cells of the invention are strains have less than 50% of the detectable intracellular or extracellular cellulase, mannanase and pectinase, and optionally amylase, activity as detected in a model reaction (see experimental information in the Examples 2, 3 or 4). More preferably, the cellulase, mannanase and pectinase, and optionally amylase, deficient strains of the invention are strains having less than 50% of the cellulase, mannanase and pectinase, and optionally amylase, activity. More preferably, the cellulase, mannanase and pectinase, and optionally amylase, deficient strains of the invention are strains having a cellulase, mannanase and pectinase, and optionally amylase, activity, which is less than 25% of the cellulase, mannanase and pectinase, and optionally amylase, activity of the host cell they originate from as detected in a model reaction, preferably less than 10%, more preferably less than 5%, more preferably less than 1% and most preferably the cellulase, mannanase and pectinase, and optionally amylase, activity is undetectable in the deficient host cells of the invention.

A large variety of systems for detection of polypeptide are known to the skilled person. Detection systems include any possible assay for detection of polypeptide or enzymatic activity. By way of example these assay systems include but are not limited to assays based on colorimetric, photometric, fluorometric, turbidimetric, viscosimetric, immunological, biological, chromatographic, and other available assays.

Preferably, if the polypeptide produced is an enzyme, the amount of active enzyme produced is determined by measurement of its activity in a model reaction (see Examples 2, 3 or 4).

According to a further preferred embodiment, the cellulase, mannanase and pectinase, and optionally amylase, deficient host cell of the invention is characterized by the fact that when this strain has been transformed with an expression construct comprising a gene coding for a polypeptide having transgalactosylating activity, said strain produces at least the amount of the polypeptide the wild type strain it originates from would produce under the same culture conditions, when the wild type strain has also been transformed with the same expression construct as the cellulase, mannanase and pectinase, and optionally amylase, deficient host cell.

Preferably, the cellulase, mannanase and pectinase, and optionally amylase, deficient strains of the invention are strains that produce the same amount or more of the polypeptide having transgalactosylating activity than the wild type strain they originate from under the same culture conditions. More preferably, the cellulase, mannanase and pectinase, and optionally amylase, deficient strain produces more of this given polypeptide than the wild type strain they originate from under the same culture conditions.

Production of Polypeptide Having Transgalactosylating Activity

According to yet another embodiment, the present invention relates to methods of transcribing a nucleotide sequence in a host cell deficient in cellulose, mannanase, pectinase and/or amylase activity, wherein the transcribed sequence encodes the polypeptide having transgalactosylating activity comprising:

(a) cultivating, in a culture medium, the host cell of the invention comprising (i) a promoter,
(iv) a downstream nucleotide sequence which encodes the polypeptide, (iii) a translational stop signal and (iv) a transcriptional stop signal,
(b) expressing the polypeptide in the host cell, and
(c) optionally, recovering the polypeptide from the culture medium or from the host cell.

The deficient strain is preferably produced according to the method of the present invention. The deficient strain may be grown or maintained in a nutrient medium suitable for production of the desired polypeptide using methods known in the art. For example, cells may be plated on a solid substrate, shaken in a flask, cultivated in small-scale or large-scale fermentation (including continuous, batch, fed-batch, or solid-state fermentation) in laboratory or industrial fermentors in a suitable medium and under conditions allowing the polypeptide to be expressed and/or isolated.

Cultivation takes place in a suitable nutrient medium comprising carbon and nitrogen sources and inorganic salts, using procedures known in the art (see, e.g., Bennett & LaSure, eds., *More Gene Manipulations in Fungi*, Academic Press, C A, 1991). Suitable media are available from commercial suppliers or may be prepared using published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be isolated by methods known in the art. For example, the polypeptide may be isolated from the nutrient medium by conventional procedures including, but not limited to, centrifugation, filtration, extraction, spray drying, evaporation, or precipitation. The isolated polypeptide may then be further purified by a variety of procedures known in the art including, but not limited to, chromatography (e.g., ion exchange, affinity, hydrophobic, chromatofocusing, or size exclusion), electrophoresis (e.g., preparative isoelectric focusing), differential solubility (e.g., acetone or ammonium sulfate precipitation), or extraction (e.g., chaotrope, salt, or pH). See, e.g., Janson & Ryden, eds., *Protein Purification*, VCH Publishers, New York, 1989.

The polypeptide may be detected using methods known in the art that are specific for the polypeptide having transgalactosylating activity. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

Methods for Producing Polypeptides

In a further aspect, a method of expressing a polypeptide as described herein comprises obtaining a host cell or a cell as described herein and expressing the polypeptide having transgalactosylating activity from the cell or host cell, and optionally purifying the polypeptide. Such a polypeptide may be used in the present invention.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989).

Methods known in the art may be used to select transformants.

Methods for Immobilising and Formulation of the Polypeptides and Polypeptide Compositions Polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Applications

Examples are given below of preferred uses of the polypeptides or polypeptide compositions of the invention.

In one aspect, disclosed herein is a method for producing a food product by treating a substrate comprising lactose with a polypeptide or a polypeptide composition as described herein.

In one aspect, disclosed herein is a method for producing a dairy product by treating a milk-based substrate comprising lactose with a polypeptide or a polypeptide composition as described herein.

In one aspect, the substrate comprising lactose is further treated with a hydrolysing beta-galactosidase.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

Examples of dry enzyme formulations include include spray dried products, mixer granulation products, layered products such as fluid bed granules, extruded or pelletized granules prilled products, lyophilyzed products.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

In one aspect, a composition preferably a food composition, more preferably a dairy product comprising a cell or a polypeptide or a polypeptide composition as described herein, is provided.

Furthermore, disclosed herein is a composition comprising at least 5%, such as e.g. 10%, 15%, 20%, 25%, 30%, 35%, 40%, 45%, 50% w/w of one or more polypeptide(s) as disclosed herein based on the total amount of polypeptides in the composition having at least 70%,e.g. such as 72%, 74%, 74%, 78%, 80%, 82%, 84%, 86%, 88%, 90% sequence identity with SEQ ID NO: 22. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometric scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity) *100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

In one aspect, the composition according to the present invention comprises one or more polypeptide(s) selected from the group consisting of a polypeptide consisting of SEQ ID NO: 1, 2, 3, 4 and 5. In a further aspect, the composition comprises one or more polypeptide(s) selected from the group consisting of a polypeptide consisting of SEQ ID NO: 1, 2 and 3. In yet a further aspect, the composition comprises one or more polypeptide(s) selected from the group consisting of a polypeptide consisting of SEQ ID NO: 1 and 2.

In one aspect the invention provides an enzyme complex preparation comprising the enzyme complex according to the invention, an enzyme carrier and optionally a stabilizer and/or a preservative.

In yet a further aspect of the invention, the enzyme carrier is selected from the group consisting of glycerol or water. In one embodiment, the enzyme carrier does not comprise a polyol (e.g., glycerol, propylene glycol, or sorbitol).

In a further aspect, the preparation/composition comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In another aspect, stabilizer is not a polyol such as glycerol, propylene glycol, or sorbitol. In yet another aspect, the sugar is a small-molecule carbohydrate, in particular any of several sweet-tasting ones such as glucose, galactose, fructose and saccharose.

In yet at further aspect, the preparation comprises a preservative. In one aspect, the preservative is methyl paraben, propyl paraben, benzoate, sorbate or other food approved preservatives or a mixture thereof.

The method of the invention can be practiced with immobilized enzymes, e.g. an immobilized lactase or other galactooligosaccharide producing enzymes. The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents. In various aspects of the invention, immobilization of the lactase can be optimized by physical adsorption on to the inorganic support. Enzymes used to practice the invention can be immobilized in different media, including water, Tris-HCl buffer and phosphate buffered solution. The enzyme can be immobilized to any type of substrate, e.g. filters, fibers, columns, beads, colloids, gels, hydrogels, meshes and the like.

In one aspect, a method for producing a dairy product by treating a milk-based substrate comprising lactose with a polypeptide or a polypeptide composition as described herein is provided. In a further aspect, a method for producing a dairy product by treating a milk-based substrate comprising lactose with a polypeptide having a relative transgalactosylation activity above 60%, such as above 70%, such as above 75% after 15 min. reaction, is provided. In one aspect, the relative transgalactosylation activity is above 3 after 30 min. reaction. In a further aspect, the relative transgalactosylation activity is above 6 after 30 min. reaction. In yet a further aspect, the relative transgalactosylation activity is above 12 after 30 min. reaction. In one aspect, a method is provided, wherein the treatment with a polypeptide or a polypeptide composition as described herein takes place at an optimal temperature for the activity of the enzyme. In a further aspect, the polypeptide or the polypeptide composition is added to the milk-based substrate at a concentration of 0.01-1000 ppm. In yet a further aspect, the polypeptide or the polypeptide composition is added to the milk-based substrate at a concentration of 0.1-100 ppm. In a further aspect, the polypeptide or the polypeptide composition is added to the milk-based substrate at a concentration of 1-10 ppm. In one aspect, a method further comprising fermenting a substrate such as a dairy product with a microorganism, is provided. In a further aspect, the dairy product is yogurt. In a further aspect, the treatment with the polypeptide or the polypeptide composition and the microorganism is performed essentially at the same time. In one aspect, the polypeptide or the polypeptide composition and the microorganism are added to the milk-based substrate essentially at the same time.

In one aspect, a dairy product comprising a cell or a polypeptide or a polypeptide composition as described herein, is provided. In one aspect, the polypeptide or the polypeptide composition as defined herein is added in a concentration of 0.01-1000 ppm.

In one aspect, a dairy product comprising GOS formed in situ by a polypeptide or a polypeptide composition as defined herein, is provided. In one aspect, a dairy product comprising a cell as defined herein, is provided.

A dairy product as described herein may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions account for at least 50% (weight/weight), such as at least 70%, e.g. at least 80%, preferably at least 90%, of the dairy product.

In one embodiment of the invention, one or more milk-based substrates having been treated with an enzyme as defined herein having transgalactosylating activity account for at least 50% (weight/weight), such as at least 70%, e.g. at least 80%, preferably at least 90%, of the dairy product.

In one embodiment of the invention, the dairy product is a dairy product which is not enriched by addition of pre-produced galacto-oligosaccharides.

In one embodiment of the invention, the polypeptide-treated milk-based substrate is not dried before being used as an ingredient in the dairy product.

In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In one embodiment of the invention, the dairy product is milk or condensed milk.

In one embodiment of the invention, the dairy product is UHT milk. UHT milk in the context of the present invention is milk which has been subjected to a sterilization procedure which is intended to kill all microorganisms, including the bacterial spores. UHT (ultra high temperature) treatment may be, e.g., heat treatment for 30 seconds at 130° C., or heat treatment for one second at 145° C.

In one preferred embodiment of the invention, the dairy product is ESL milk. ESL milk in the present context is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt.

The microorganisms used for most fermented milk products are selected from the group of bacteria generally referred to as lactic acid bacteria. As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria, i.e. *Bifidobacterium* spp., which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis* biovar. *diacetylactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*.

Also the anaerobic bacteria belonging to the genus *Bifidobacterium* including *Bifidobacterium bifidum, Bifidobacterium animalis* and *Bifidobacterium longum* are commonly used as dairy starter cultures and are generally included in the group of lactic acid bacteria. Additionally, species of Propionibacteria are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir, Saccharomyces kefir* and *Saccharomyces cerevisiae*.

In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus*.

Fermentation processes to be used in a method of the present invention are well known and the person of skill in the art will know how to select suitable process conditions, such as temperature, oxygen, amount and characteristics of microorganism/s, additives such as e.g. carbohydrates, flavours, minerals, enzymes, and process time. Obviously, fermentation conditions are selected so as to support the achievement of the present invention.

As a result of fermentation, pH of the milk-based substrate will be lowered. The pH of a fermented dairy product of the invention may be, e.g., in the range 3.5-6, such as in the range 3.5-5, preferably in the range 3.8-4.8.

In one aspect, a method of using the polypeptides or the polypeptide composition or using any one or more of the above mentioned cell types for producing oligosaccharides, is provided. The oligosaccharides comprise, but are not limited to fructooligo-saccharides, galacto-oligosaccharides, isomalto-oligosaccharides, malto-oligosaccharides, lactosucrose and xylo-oligosaccharides.

In one embodiment of the invention, the oligosaccharides are produced by incubating the cell expressing the polypeptide in a medium that comprises a disaccharide substrate such as for example lactulose, trehalose, rhamnose, maltose, sucrose, lactose, or cellobiose. The incubation is carried out under conditions where oligosaccharides are produced. The cells may be part of a product selected from the group consisting of yoghurt, cheese, fermented milk products, dietary supplements, and probiotic comestible products. Alternatively, the oligosaccharides can be recovered and subsequently be added to the product of interest before or after its preparation.

In one aspect, the use of a herein disclosed cell for producing a product selected from the group consisting of yoghurt, cheese, fermented milk product, dietary supplement and probiotic comestible product, is provided.

In one aspect, the polypeptides or the polypeptide composition described herein may be used to prepare cheese products and in methods for making the cheese products. Cheese products may e.g. be selected from the group consisting of cream cheese, cottage cheese, and process cheese. By adding polypeptides or the polypeptide composition the cheeses may contain significantly increased levels of galacto-oligosaccharides and reduced levels of lactose. In one aspect, the lactose levels in the final cheese product may be reduced by at least about 25 percent, preferably at least about 50 percent, and more preferably at least about 75 percent. The polypeptides or the polypeptide composition may be used to reduce lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavor. Further, the polypeptides described herein may reduce the glycemic index of the cheese products because GOS are more slowly absorbed than lactose or its hydrolysis products. Finally, the polypeptides or the polypeptide composition may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, a composition comprising a polypeptide or a polypeptide composition as described herein and a carbohydrate substrate, is provided. In a further aspect, the carbohydrate substrate is a disaccharide. In a further aspect, the disaccharide is for example lactulose, trehalose, rhamnose, maltose, sucrose, lactose or cellobiose. In yet a further aspect, the carbohydrate substrate is lactose. The composition is prepared such that oligosaccharides are produced. The polypeptide as described herein may be part of a product selected from the group consisting of yoghurt, cheese, fermented milk products, dietary supplements, and probiotic comestible products. In one aspect, a composition comprising a polypeptide as described herein and a stabilizer, is provided. Examples of stabilizers is e.g., a polyol such as, e.g., glycerol or propylene glycol, a sugar or a sugar alcohol, lactic acid, boric acid, or a boric acid derivative (e.g., an aromatic borate ester).

In one aspect, the use of a transgalactosylating polypeptide or a polypeptide composition as disclosed herein or a cell as disclosed herein, for producing galacto-oligosaccharides, is provided. In one aspect, the use of a transgalactosylating polypeptide or a polypeptide composition as disclosed herein or a cell as disclosed herein, for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a transgalactosylating polypeptide or a polypeptide composition as disclosed herein or a cell as disclosed herein, for producing galacto-oligosaccharides to enhance the growth of *Bifidobacterium*, is provided. In one aspect, the use of a transgalactosylating polypeptide or a polypeptide composition as disclosed herein or a cell as disclosed herein, for producing galacto-oligosaccharides to enhance the growth of *Bifidobacterium* in a mixed culture fermentation, is provided.

In one aspect, a process for producing a transgalactosylating polypeptide or a polypeptide composition as disclosed herein, comprising culturing a cell as disclosed herein in a suitable culture medium under conditions permitting expression of said polypeptide, and recovering the resulting polypeptide from the culture, is provided. A process for producing galacto-oligosaccharides, comprising contacting of a polypeptide or a polypeptide composition as disclosed herein or a cell as disclosed herein with a milk-based solution comprising lactose, is provided.

Addition of oligosaccharides may enhance growth of either *Bifidobacterium* alone or of *Bifidobacterium* in a mixed culture.

The treatment of milk products with enzymes that converts lactose into monosaccharides or GOS have several advantages. First the products can be consumed by people with lactose intolerance that would otherwise exhibit symptoms such as flatulence and diarrhea. Secondly, dairy products treated with lactase will have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. Thirdly, in ice-cream production a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by whey powder. The main effects of the enzymatic treatment were increased sweetness.

In one aspect, the transgalactosylating polypeptide or the polypeptide composition as disclosed herein may be used together with other enzymes such as proteases such as chymosin or rennin, lipases such as phospholipases, amylases, transferases, and lactases. In one aspect, the transgalactosylating polypeptide(s) as disclosed herein may be used together with lactase. This may especially be useful when there is a desire to reduce residual lactose after treatment with the transgalactosylating polypeptide(s) as disclosed herein especially at low lactose levels. In one embodiment, the enzyme is a lactase from a bacterium, e.g. from the family Bifidobacteriaceae, such as from the genus *Bifidobacterium* such as the lactase described in, inter alia, WO 2009/071539 and WO 2013/182686.

Example 1—Construction of a Host Cell According to the Invention

The host cell of this Example is derived from *B. subtilis*.

Removal of amyE alpha-amylase gene: An in-vitro created deletion of the wild-type gene (amyE) was introduced into *B. subtilis* strain by recombinant DNA techniques. The amyE deletion was monitored by activity as well as Southern blots. No heterologous DNA remained in the host strain.

Replacement of the bglC endoglucanase gene by a spectinomycin marker: To delete the bglC gene a strategy employing a cre-lox method was employed. The upstream and downstream bglC sequences were cloned, and the middle (to be deleted) part was replaced by a loxP-spectinomycin cassette allowing selection at the transformation. A *B. subtilis* strain was transformed with the construct selecting for spectinomycin, replacing the genomic bglC gene with the cloned variant. Genomic DNA from the strain containing the spectinomycin marker was integrated into a deletion of the endoglucanase bglC locus was used to transform the strain via natural competence. Positive clones were determined by spectinomycin resistance. The spectinomycin resistance gene is flanked by loxP sequences enabling removal of the gene.

Replacement of the gmuG mannanase gene by a tetracycline marker: The mannanase gmuG was deleted using the same technique as for the bglC gene, although this time a tetracycline marker was used instead of a spectinomycin marker. Transformants were selected on tetracycline containing media and positive clones were verified with PCR.

Replacement of the pel pectate lyase gene by a spectinomycin marker: The pectate lyase gene pel was deleted using the same technique as used for the bglC gene, by replacing the pel ORF with the spectinomycin marker. Transformants were selected on spectinomycin plates and were screened by cPCR.

Introduction of the BIF917 gene: The coding sequence for β-galactosidase disclosed in WO 2013/182626 as "BIF917" was transformed in a *B. subtilis* using methods set out in this publication. In general terms this describes the production of polypeptide using synthetic genes designed to encode the *Bifidobacterium bifidum* full length (1752 residues) gene with codons optimised for expression in *Bacillus subtilis* were purchased from GeneART (Regensburg, Germany) SEQ ID No. 8.

The *Bifidobacterium bifidum* truncation mutants were constructed using polymerase chain reaction with reverse primers that allowed specific amplification of the selected region of the synthetic gene.

Forward primer:

(SEQ ID NO: 15)
GGGGTA<u>ACTAGT</u>GGAAGATGCAACAAGAAG (SpeI underlined).

The SEQ IDs for the truncation mutants and corresponding reverse primers are indicated in Table 2 below.

TABLE 2

| Truncation mutant | Primer sequence |
|---|---|
| BIF917 (SEQ ID NO: 9) | GCGCTTAATTAATTATGTTTTTCTGTGCTT GTTC SEQ ID NO: 16 |
| BIF995 (SEQ ID NO: 10) | GCGCTTAATTAATTACAGTGCGCCAATTTCA TCAATCA SEQ ID NO: 17 |
| BIF1068 (SEQ ID NO: 11) | GCGCTTAATTAATTATTGAACTCTAATTGTC GCTG SEQ ID NO: 18 |
| BIF1172 (SEQ ID NO: 12) | |
| BIF1241 (SEQ ID NO: 13) | GCGCTTAATTAATTATGTCGCTGTTTTCAGT TCAAT SEQ ID NO: 19 |
| BIF1326 (SEQ ID NO: 14) | GCGCTTAATTAATTAAAATTCTTGTTCTGTG CCCA SEQ ID NO: 20 |
| BIF 1478 | GCGCTTAATTAATTATCTCAGTCTAATTTCG CTTGCGC SEQ ID NO: 21 |

The synthetic gene was cloned into the pBNspe *Bacillus subtilis* expression vector using the unique restriction sites SpeI and PacI and the isolated plasmids were transformed into a *Bacillus subtilis* strain. Transformants were restreaked onto LB plates containing 10 µg/mL Neomycin as selection.

Measuring β-Galactosidase Activity

Enzymatic activity was measured using the commercially available substrate 2-Nitrophenyl-β-D-Galactopyranoside (ONPG) (Sigma N1127).

| ONPG w/o acceptor |
|---|
| 100 mM KPO4 pH 6.0 |
| 12.3 mM ONPG |
| ONPG supplemented with acceptor |
| 100 mM KPO4 pH 6.0 |
| 20 mM Cellobiose |
| 12.3 mM ONPG |
| STOP Solution |

| 10% $Na_2CO_3$ |
|---|

10 µl dilution series of purified enzyme was added in wells of a microtiter plates containing 90 µl ONPG-buffer with or without acceptor. Samples were mixed and incubated for 10 min at 37° C., subsequently 100 µl STOP Solution were added to each well to terminate reaction. Absorbance measurements were recorded at 420 nm on a Molecular Device SpectraMax platereader controlled by the Softmax software package.

The ratio of transgalactosylation activity was calculated as follows:

Ratio of transgalctosylation activity=$(Abs420^{+Cellobiose}/Abs420^{-Cellobiose})*100$, for dilutions where the absorbance was between 0.5 and 1.0.

Determination of LAU Activity

Principle:

The principle of this assay method is that lactase hydrolyzes 2-o-nitrophenyl-β-D-galactopyranoside (ONPG) into 2-o-nitrophenol (ONP) and galactose at 37° C. The reaction is stopped with the sodium carbonate and the liberated ONP is measured in spectrophotometer or colorimeter at 420 nm.

Reagents:

MES buffer pH 6.4 (100 mM MES pH 6.4, 10 mM $CaCl_2$): Dissolve 19.52 g MES hydrate (Mw: 195.2 g/mol, Sigma-aldrich # M8250-250G) and 1.470 g $CaCl_2$ di-hydrate (Mw: 147.01 g/mol, Sigma-aldrich) in 1000 ml $ddH_2O$, adjust pH to 6.4 by 10M NaOH. Filter the solution through 0.2 µm filter and store at 4° C. up to 1 month.

ONPG substrate pH 6.4 (12.28 mM ONPG, 100 mM MES pH 6.4, 10 mM $CaCl_2$): Dissolve 0.370 g 2-o-nitrophenyl-β-D-galactopyranoside (ONPG, Mw: 301.55 g/mol, Sigma-aldrich # N1127) in 100 ml MES buffer pH 6.4 and store dark at 4° C. for up to 7 days.

Stop reagent (10% $Na_2CO_3$): Dissolve 20.0 g $Na_2CO_3$ in 200 ml $ddH_2O$, Filter the solution through 0.2 µm filter and store at RT up to 1 month.

Procedure:

Dilution series of the enzyme sample was made in the MES buffer pH 6.4 and 10 µL of each sample dilution were transferred to the wells of a microtiter plate (96 well format) containing 90 µl ONPG substrate pH 6.4. The samples were mixed and incubated for 5 min at 37° C. using a Thermomixer (Comfort Thermomixer, Eppendorf) and subsequently 100 µl Stop reagent was added to each well to terminate the reaction. A blank was constructed using MES buffer pH 6.4 instead of the enzyme sample. The increase in absorbance at 420 nm was measured at a ELISA reader (SpectraMax platereader, Molecular Device) against the blank.

Calculation of Enzyme Activity:

The molar extinction coefficient of 2-o-nitrophenol (Sigma-aldrich #33444-25G) in MES buffer pH 6.4 was determined $(0.5998\times10^{-6}M^{-1}\times cm^{-1})$. One unit (U) of lactase activity (LAU) was defined as that corresponding to the hydrolysis of 1 nmol of ONPG per minute. Using microtitre plates with a total reaction volume of 200 µL (light path of 0.52 cm) the lactase activity per mL of the enzyme sample may be calculated using the following equation:

$$LAU/ml\left(\frac{nmol}{min\cdot mL}\right) = \frac{Abs_{410} \times 200 \text{ µL} \times \text{dilution factor}}{0.5998\cdot 10^3 \cdot nM^{-1}\cdot cm^{-1} \times 0.52 \text{ cm} \times 5 \text{ min} \times 0.01 \text{ mL}}$$

Calculation of Specific Activity for BIF917 Shown Herein as SEQ ID NO: 1:

Determination of BIF917 Concentration:

Quantification of the target enzyme (BIF917) and truncation products were determined using the Criterion Stain free SDS-page system (BioRad). Any kD Stain free precast Gel 4-20% Tris-HCl, 18 well (Comb #345-0418) was used with a Serva Tris-Glycine/SDS buffer (BioRad cat. #42529). Gels were run with the following parameters: 200 V, 120 mA, 25 W, 50 min. BSA (1.43 mg/ml) (Sigma-Aldrich, cat. #500-0007) was used as protein standard and Criterion Stain Free Imager (BioRad) was used with Image Lab software (BioRad) for quantification using band intensity with correlation of the tryptophan content.

The specific LAU activity of BIF917 was determined from crude ferment (ultra filtration concentrate) of two independent fermentations (as described in method 1) and using 5 different dilutions (see table 1).

The specific activity of BIF917 was found to be 21.3 LAU/mg or 0.0213 LAU/ppm.

TABLE 1

Determination of BIF917 specific activity

| Sample ID | Enzyme | Fermentation | Dilution factor | Activity LAU/ml | Protein (BIF917) concentration mg/ml | Protein (BIF917) concentration ppm | Specific activity LAU/mg | Specific activity LAU/ppm |
|---|---|---|---|---|---|---|---|---|
| 1 | BIF 917 | a | 5 | 26.9 | 1.23 | 1232 | 21.9 | 0.0219 |
| 2 | BIF 917 | a | 10 | 53.9 | 2.44 | 2437 | 22.1 | 0.0221 |
| 3 | BIF 917 | a | 10 | 75.4 | 3.56 | 3556 | 21.2 | 0.0212 |
| 4 | BIF 917 | a | 20 | 163.9 | 7.78 | 7778 | 21.1 | 0.0211 |
| 5 | BIF 917 | a | 30 | 233.6 | 11.06 | 11065 | 21.1 | 0.0211 |
| 6 | BIF 917 | b | 5 | 30.26825 | 1.34 | 1342 | 22.6 | 0.0226 |
| 7 | BIF 917 | b | 10 | 55.91536 | 2.61 | 2607 | 21.4 | 0.0214 |
| 8 | BIF 917 | b | 10 | 76.96056 | 3.70 | 3697 | 20.8 | 0.0208 |
| 9 | BIF 917 | b | 20 | 156.986 | 7.75 | 7755 | 20.2 | 0.0202 |
| 10 | BIF 917 | b | 30 | 236.9734 | 11.45 | 11452 | 20.7 | 0.0207 |
|  |  |  |  |  |  | Arg | 21.3 | 0.0213 |
|  |  |  |  |  |  | Std | 0.700976 | 0.000701 |

Example 2

Test: 1
Assay: P-Mannanase Activity, Reducing Sugar (MU)
This test method is to be used to determine the mannanase activity in MU (MannanaseUnits) units.
Purpose
This assay is suitable for QA/QC monitoring of mannanase activity.
PRINCIPLE This assay measures the release of reducing sugars by the action of Endo-1,4-P-D-mannanase on a Locust Bean Gum (LBG) substrate. Dinitrosalicylic acid reaction is used to determine the increase in reducing sugar content, which is proportional to the enzyme activity added.
PROCEDURE
1. Materials and Equipment
1.1 Centrifuge, capable of 3500 rpm
1.2 Water bath set at 40° C.
1.3 Water bath set at 60° C.
1.4 Boiling water bath
1.5 Positive displacement pipets and tips (Ranin Inc.)
1.6 Vortex
1.7 16×100 mm glass test tubes (with caps)
1.8 Timer
1.9 Volumetric flasks, graduate cylinders, beakers
1.10 Magnetic stir bars and stirring/hot plate
1.11 Sintered glass filter funnel
1.12 pH meter
1.13 Analytical balance
1.14 Preparative balance
1.15 Thermometers
1.16 Ice water bath
1.17 Spectrophotometer, capable of reading 540 nm
1.18 Variable pipetting device (1 ml) with disposable tips
1.20 Oven or autoclave for glassware
2. Reagents: Use the following reagents or equivalent
2.1 Ammonium Hydroxide, concentrated (28-30%)
2.2 Tris-Hydroxymethylaminomethane (Tris) hydrochloride
2.3 Sodium Hydroxide Pellets
2.4 3,5-dinitrosalicylic Acid, 98%, (DNS), Sigma-Aldrich Cat. #128848
2.5 Locust Bean Gum, Sigma Chemical # G0753
2.6 Potassium Sodium Tartrate, tetrahydrate, Sigma-Aldrich Cat. #217255
2.7 Deionized Water
2.8 1-Propanol
3. Reagents Preparation
3.1 Ammonim Hydroxide 1.5%
  3.1.1 Using deionized water, dilute 5 ml of 30% Ammonium Hydroxide to 100 ml in a volumetric flask.
3.2 Tris-Hydrochloride Buffer
  3.2.1 Dissolve 15.67 gm of Tris-Hydrochloride in approximately 1900 ml of deionized water. Adjust to pH 7.5±0.05 with Ammonium Hydroxide (1.5%) and dilute to 2000 ml with deionized water. This solution can be held for at least two weeks at room temperature.
3.3 Sodium Hydroxide 10.67%
  3.3.1 Add 32.0 gm of Sodium Hydroxide pellets to 200 ml of deionized water. Stir until dissolved and cooled. Bring up to 300 ml with deionized water
3.4 DNS Reagent
(a) Suspend 20 gm of DNS in 1000 ml of deionized water in a 2 L beaker. Add 300 ml of 10.67% Sodium Hydroxide solution.
(b) Warm the suspension on a heated stir plate until the solution is clear. The temperature should not exceed 50° C.
(c) Gradually add 600 gm of Potassium Sodium Tartrate Tetrahydrate to the solution with continual mixing. Allow solution to reach room temperature.
(d) Dilute the solution to 2000 ml with deionized water and filter if required through a course sintered glass filter. Store in a dark amber bottle at room temperature. The solution is good for at least two months.
3.5 Locust Bean Gum (LBG) Substrate Solution
3.5.1 Make sure all glassware that comes in contact with substrate is extremely clean and free of possible mannanase contamination. 1-Propanol washes or baking at 120° C. are recommended.
5.1.1 Place 500 ml of Tris-Hydrochloride buffer in a 1000 ml beaker. Place the beaker in a boiling water bath or heated stir plate and allow the temperature in the beaker to reach 80° C. Rapidly stir the solution while very slowly adding 1.4 gm of Locust Bean Gum. Reduce mixing and hold the solution at 60° C. in a water bath for 60 minutes. Cool to room temperature. Adjust to 500 ml with deionized water. Centrifuge at 3,500 rpm for 10 minutes. Use the clear supernatant as the substrate.

3.6 Enzyme Standard Preparation
3.6.1 Choose a lot of mannanase final product as a standard. Set this equal to the MU value reported on the lot's Certificate of Analysis. Using this material, make a 3 point standard curve using a sample of known concentration in MU/liter. Dilute the standard accordingly, using Tris-Hydrochloride Buffer so that its net absorbance falls within the linear range of the assay after the subtraction of the reagent blank. The linear range of this assay is 0.17 and 0.52 AA. Standard curve and sample concentrations between 0.050-0.140 MU/liter typically fall within the linear range of this assay.

3.7 Liquid Sample Preparation
3.7.1 Dilute each sample (w/v) in Tris-Hydrochloride Buffer such that the assay reaction outlined in Section 4 falls between 0.17 and 0.52 AA at 540 nm.
3.7.2 Store diluted enzyme solutions on ice. For best results, diluted enzyme solutions should be assayed within 1 hour.

4. Assay Procedure
4.1 Enzyme Samples—Enzyme samples should be assayed in duplicate
4.1.1 Equilibrate 2 ml of LBG Substrate at 40° C. in 16×100 glass test tubes for 20 minutes.
4.1.2 Add 0.5 ml of enzyme sample dilution, mix and incubate for exactly 10 minutes.
4.1.3 Stop the reaction by the addition of 3.0 ml of the DNS-solution and mix.
4.1.4 Boil the sample for 15 minutes in the boiling water bath, covering the top of each test tube with a cap to prevent evaporation. Cool in an ice water bath for 50 minutes. Allow samples to equilibrate to room temperature for 10 minutes.
5.1.1 Read the absorbance at 540 nm against a deionized water blank. The absorbance should be between 0.17 and 0.52 AA, after the subtraction of the reagent blank.

4.2 Reagent Blank
4.2.1 Blank can be run singularly. This reaction control is for reducing sugar present in the LBG substrate or present in the enzyme sample.
5.1.1 Equilibrate 2 ml of LBG substrate at 40° C. in 16×100 glass test tubes for 20 minutes.
5.1.2 Incubate for an additional 10 minutes.
5.1.3 Add 3.0 ml of DNS-solution and mix. Add 0.5 ml of enzyme dilution and mix again.
5.1.4 Boil for 15 minutes in the boiling water bath, covering the top of the test tube with a cap to prevent evaporation. Cool in an ice water bath for 5 minutes. Allow samples to equilibrate to room temperature for 10 minutes.
5.1.5 Read the absorbance at 540 nm against deionized water blank.

5. Calculations
5.1 To determine the net AAbsorbance, subtract the average reagent/enzyme blank from the absorbance reading of all standards and samples.
5.2 Prepare a standard curve using linear regression where net absorbance is on the y-axis and concentration (MU/liter) on the x-axis.
5.3 The correlation coefficient must be >0.998.
5.4 Determine the concentration of each sample from linear regression.
5.5 For liquids: MU Manannase/kg sample=value from curve (MU/liter)*sample dilution factor (total volume (liter)/sample weight (kg))

Example 3

Test 2: Endoglucanase Activity, Carboxymethyl Cellulose (CMC) Activity
PURPOSE This test method is to be used to determine the endoglucanase activity of Cellulase in CMC units.
Note: Cellulase reported in IU/g or IU/ml (International Units) is equivalent to CMC/g or CMC/ml, respectively.
PRINCIPLE This assay measures the release of reducing sugars by the action of cellulase on a CMC substrate. The rate of reducing sugar release, as measured by the reaction with 3,5 dinitrosalicylic acid (DNS), is proportional to the enzyme activity. One CMC unit is defined as the amount of enzyme required to generate 1 $\hat{}$.mole of glucose reducing sugar equivalents per minute under the conditions of the assay. The activity in this procedure is measured relative to an enzyme standard with assigned CMC units.

PROCEDURE
1.0 Materials and Equipment
1.18 18×150 mm test tubes
1.19 Marbles
1.20 Cuvettes
1.21 Positive displacement pipettes and tips, Ranin Inc.
1.22 pH meter
1.23 Water bath set at 50° C.
1.24 Ice bath
1.25 Boiling water bath
1.26 Spectrophotometer
1.27 Magnetic stirrer
1.28 Stop watch
1.29 Coarse glass Filter©, VWR KT93700-47
1.30 Dark amber bottle
1.31 Positive displacement pipettes
1.32 Vortexer
1.33 Test tube rack
2.0 Reagents: Use the following reagents or equivalent.
2.9 Carboxymethyl Cellulose Sodium Salt
  Fluka 21900 Degree of substitution must be 0.70-0.85
2.10 3,5-dinitrosalicylic Acid, Sodium Salt (DNS), Merck 10846
2.11 Potassium Sodium Tartrate, Tetrahydrate, Merck 8087
2.12 Sodium Hydroxide, reagent grade
2.13 Glacial Acetic Acid, reagent grade
3.0 Reagents Preparation
3.1 0.05 M Sodium Acetate Buffer, pH 4.8
  3.1.1 To 900 mL of distilled water, add 2.85 mL of glacial acetic acid. While stirring with a magnetic stir bar, adjust the pH to 4.8 with 50% sodium hydroxide. Bring to a total volume of one liter with distilled water.
3.4 10.67% (w/v) Sodium Hydroxide Solution
  3.2.1 Add 32.0 g of sodium hydroxide pellets to 200 mL of distilled water. Stir until dissolved and cooled. Bring up to 300 mL with distilled water.
3.5 1% CMC Substrate Solution
  3.3.1 To 99 mL of sodium acetate buffer, add 1.00 g CMC. Stir to mix thoroughly and keep at 4° C. for at least 1 hour before using. The solution is stable for 3 days at 4° C.
3.6 1% 3-5 Dinitrosalicylic Acid (DNS)
  (e) Suspend 20.0 g of DNS in 1000 mL of distilled water and gradually add 300 mL of the 10.67% sodium hydroxide solution while mixing.

(f) Warm the suspension in a water bath set at 50° C. (122° F.) until the solution is clear. The water bath temperature should not exceed 50° C.
3.4.3 Gradually add 600 g of potassium sodium tartrate tetrahydrate to the solution with continual mixing.
3.4.4 Dilute the solution to 2000 mL with distilled water and filter through a coarse glass filter. Store in a dark amber bottle at room temperature. The solution is stable for 2 months. The solution must be clear for use.
4.1 Granule Sample Preparation
3.7.2 Dissolve granular samples in acetate buffer such that the net absorbance yielded from the assay reaction outlined in section 4.5 falls between 0.4 and 0.5. A preparation at about 0.2 CMC/mL will typically yield the desired absorbance.
3.7.3 When preparing samples, weigh out at least 100 mg of granule. Dissolve accordingly with acetate buffer per 4.1.1 by using magnetic stirring. Record the granule concentration in mg/mL for calculations in 5.1. Mix at a medium speed for at least 20 minutes. Store diluted samples on ice. Stable for at least 2 hours.
3.7.4 Note that some samples will form a fine slurry after the mixing time. Representative slurry samples should be taken to perform the assay in 4.5.
4.1.4 Perform each granular sample preparation in triplicate.
4.2 Liquid Sample Preparation
4.1.3 Dilute each sample in acetate buffer such that the net absorbance yielded from the assay reaction outlined in section 4.5 falls between 0.4 and 0.5. A preparation at about 0.2 CMC/mL will typically yield the desired absorbance.
4.1.4 When preparing samples, aliquot out at least 0.10 mL of liquid sample using a positive displacement pipet. Store dilulted sample on ice.
Stable for at least 2 hours.
4.1.5 Perform each liquid sample preparation in triplicate.
4.3 Working Standard Preparation
4.4
4.3.1 Choose a lot of cellulase final product (either liquid or granule) as a standard. Set this equal to the CMC value reported on the lot's Certificate of Analysis. Using this material, prepare a working standard of known CMC/mL per 4.1 or 4.2. Dilute the standard using acetate buffer such that the net absorbance yield from the assay reaction outlined in section 4.5 falls between 0.4 and 0.5. A preparation of a standard solution at about 0.2 CMC/mL will typically yield the desired absorbance
4.3.2 Record the activity of the working standard in CMC/mL. Use this in the calculation sections 5.1 and 5.2.
4.3.3 Prepare the standard in triplicate.
4.4 Blank Solution
4.4.1 Use acetate buffer as a blank enzyme solution in section 4.5. Run each blank enzyme solution in in duplicate.
4.5 Enzyme Assay Reaction
4.5.1 Incubate 1.00 mL of CMC substrate at 50° C. in 18×150 mm glass test tubes for 10-15 minutes, set up in a test tube rack.
4.5.2 At 20 second intervals, add 1.00 mL of the enzyme dilutions and blanks to the CMC substrate using a positive displacement pipette. Mix and incubate each reaction at 50° C. (122° F.) for 10 minutes.
4.5.3 At the same timed intervals as in 4.5.2, add 3.0 mL of DNS-solution and mix.
4.5.4 Boil all the reaction mixtures+DNS for exactly 5 minutes by placing the test tubes and rack in a boiling water bath. Cover the tops of the test tubes with marbles to prevent evaporation during boiling. All samples, stds., and blanks should be boiled together. After boiling, cool the tubes in an ice bath.
4.5.5 Measure the absorbance of the enzyme samples and blanks at 540 nm against distilled water as zero absorbance.
4.5.6 Subtract the average blank absorbance from the average sample and standards absorbance. This net absorbance should be between 0.4-0.5. If it is not, then the assay should be repeated.
4.5.7 Run each enzyme sample in triplicate in the assay
5.0 Calculations
5.1 Calculate the activity in granular samples as follows:

CMC/g(or IU/g)=(net abs. sample)(CMC/mL of working std.)(1000 mg/g)(net abs. working std.) (mg granule/mL acetate buffer)

5.2 Calculate the activity in liquid samples as follows:

CMC/mL(or IU/ml)=(net abs. sample)(CMC/mL of working std.)(smple dilution)(net abs. working std.)

Note: Cellulase reported in IU/g or IU/ml (International Units) is equivalent to CMC/g or CMC/ml, respectively.

Example 4

Test 3
A Viscoman-based viscosity method is used. This method may be presently used for detection of very low levels of mannanase, amylase, CMC'ase and pectinase activities. (Useful viscosity methods are also disclosed in US 2013/0045498 which is incorporated by reference). The hydrocolloid is cleaved by the enzyme, thereby creating a drop in viscosity of the hydrocolloid solution. The reduction in viscosity is presented as a relative viscosity value calculated from the viscosity of an enzyme added hydrocolloid sample relative to viscosity of a hydrocolloid sample which was added $H_2O$. Therefore, the value will always be between 1 and 0 where 1 means no reduction in viscosity of the sample.
Substrates are GUAR, starch, CMC or pectin.
Two buffers are used depending on the substrate;
McIlvaine's Citric Acid Phosphate:
A) 0.1M citric acid; 21.0 g C6H8O7, H2O/1 L dem. water
B) 0.2M disodium hydrogenphosphate; 35.6 g Na2HPO4, 2H2O/1 L dem. water. Shelf life: 3 months
Buffer pH 4.0=71.50 ml A+28.50 ml B (in graduated cylinder)
Buffer pH 6.7=25.00 ml A+75.00 ml B
Substrate Concentrations:

| Pectin | 2.0% | pH 4.0 |
| CMC | 0.5% | pH 6.7 |
| GUAR | 0.5% | pH 6.7 |
| Starch | 3.0% | pH 6.7 |

Preparation of Substrate Solution:
The buffer used for the specific substrate is diluted five times with water and heated in Blue Cap bottles on a hotplate with magnet. The hydrocolloid is weighed and when the buffer bubbles, the powder is sprinkle in under vigorous stirring until diluted (app. 30 min). For starch, it is recommended to turn off the heat at addition of substrate and take off the lid of the bottle and avoid the substrate from boiling over—all to prevent formation of lumps etc. The hydrocolloid solution is cooled to 40° C., except for starch solution. The starch must be stored at 50° C. until use in order to prevent retro gradation.

Sample Treatment 5 ml substrate for each sample including blank is transfer to a Wheaton glass. 100 µl enzyme sample or dilutions (made with water) of the sample is added to the 5 mL substrate solution and mixed. Up to 500 µL of sample can be added as long as the same volume is applied to the blank sample. Samples are incubated at 40° C. for 20 h and then the reaction is stopped by putting samples on ice. Samples are then tempered at 10° C. for viscosity measure using Brookfield.

Example 5

Enzyme Side Activity Screen

The screen was conducted on the Sample 1 and the commercial GODO YNL2 lactase for comparison. Sample 1 is a polypeptide composition comprising an enzyme having transgalactosylating activity produced by a B. subtilis host cell in which cellulose, mannanase and pectinase are not inactivated The assays and results are listed in Table 2. It was observed that Sample 1 had a significantly higher levels of mannanase and CMCase activity compared to GODO YNL2 lactase.

TABLE 2

| Sample ID | Sample 1 | GoDo-YNL2 |
| --- | --- | --- |
| Test 3 Pectinase, Rel. act. | Uf: 0.552 F10: 0.895 F100: 0.964 | Uf: 0.806 F10: 1.016 F100: 0.989 |
| Test 3 Mannanase, Rel. act. | Uf: 0.006, F10: 0.009 F100: 0.011 | Uf: 1.010 F10: 1.011 F100: 1.001 |
| Test 3 CMCase, Rel. act. | Uf: 0.010 F10: 0.008 F100: 0.010 | Uf: 0.989 F10: 0.995 F100: 1.021 |

Semi Quantification of Mannanase and Cellulase Levels

The level of the cellulase and mannanase present in the Sample 1 was evaluated by diluting the sample until almost no change in viscosity could be observed. A macerating enzyme was tested to determine whether it had an effect on the level of mannanase and cellulase present in the final product when used in the soy media during fermentation. The macerating enzyme is a known cellulase and it was therefore only tested for mannanase activity as cellulase activity would be expected. The degree of dilutions (see Table 3) indicates high level of mannanase activity in the macerating enzyme and high level of both mannanase and cellulase activity in the Sample. The level of mannanase activity present in the macerating enzyme could not solely explain the mannanase level present, as the relative viscosity was close to 1 in F10.000 dilution of the macerating enzyme whereas the sample 1 had to be diluted more than F100.000 in order to be close to 1 in relative viscosity.

Relative viscosity of a GUAR or CMC solution added 100 µL of indicated dilution of either macerating enzyme stock or Sample 1. The macerating enzyme stock is a 54× dilution of the macerating sample which corresponds to the dilution made when adding the enzyme to the soy media during fermentation.

TABLE 3

| Sample dilution | Maceration Enzyme stock 54x dilution GUAR | BIF 917 GUAR | BIF 917 CMC |
| --- | --- | --- | --- |
| 1x | 0.034 | | 0.009 |
| 10x | 0.235 | 0.044 | |
| 100x | 0.708 | 0.054 | |
| 1.000x | | 0.123 | |
| 10.000x | 0.957 | 0.429 | 0.302 |
| 100.000x | | 0.900 | 0.874 |

Side Activity Screen in New Host Strain Knocked Out for Pectinase, Mannanase and Cellulase.

It was decided to knock out pectinase, cellulase and mannanase from the B. subtilis host strain (Sample 2) and then retest for the presence of the side activities. A sample of the first 3K fermentation using the new strain was received for analysis. Comparing the results from the 3K sample with the ones using the Sample 1, it was clear that the side activity levels for pectinase, cellulase and mannanase were lower using Sample 2 (see Table 4).

TABLE 4

| | Pectinase Relative act. | Mannanase Relative act. | CMCase Relative act. |
| --- | --- | --- | --- |
| Sample 1 Lactase | Uf: 0.552 F10: 0.895 F100: 0.964 | Uf: 0.006, F10: 0.009 F100: 0.011 | Uf: 0.010 F10: 0.008 F100: 0.010 |
| Sample 2 Lactase | F1: 0.607 F10: 1.020 F100: 1.027 | Uf: 0.009 F10: 0.223 F100: 0.875 | Uf: 0.025 F10: 0.030 F100: 0.081 |

Specifications for Viscosity Assays Using Gilson Viscoman

In order to determine threshold levels for mannanase and cellulase activity in yoghurt application, an assay for quantification of Mannanase and cellulase activity based on viscosity reduction was used. For this assay, a Viscoman pipetman from Biolab A/S was used to determine the viscosity in each sample.

To determine the variation within a sample using Viscoman, the viscosity was measured on 0.5% GUAR substrate made according to Test 3. Three sample measurements were made on 6 different substrate preparations. The maximum variation seen in 6 runs was ~4%. To be safe, the limit for variation within a sample was set to 5%. In order for the variation of the blank sample not to overlap with variation of an enzyme added sample we would need to observe a change in viscosity at more than 10%. This means that the relative viscosity should be less than 0.9 in order to say that the sample contained mannanase activity. The upper limit in terms of relative viscosity for standard curve was therefore set to be 0.85.

TABLE 5

| Run nr. | Average viscosity (Cp) | STDEV | CV % |
| --- | --- | --- | --- |
| 1 | 51.67 | 0.23 | 0.45 |
| 2 | 64.57 | 0.81 | 1.25 |
| 3 | 68.00 | 0.82 | 1.20 |
| 4 | 68.30 | 2.62 | 3.84 |
| 5 | 77.10 | 1.51 | 1.96 |
| 6 | 78.80 | 1.40 | 1.78 |

The enzyme dilution range suitable for a mannanase viscosity assay was tested using standard 699 MU/Kg). A sample containing mannanase activity, Sample 1, was also tested. It was found by least square method that the data presented a straight line when relative viscosity was plotted against LN (MU/Kg) (see FIG. 2). From 6 runs with the standard enzyme dilutions in GUAR substrate it was concluded that a straight line in which $R^2 \geq 0.98$, was presented within the range 0.25-0.85 (data not shown). To limit the amount of tests, a specification for relative viscosity values was set to be $\geq 0.25$ and $\leq 1.85$ for all substrates used.

Figure 2:
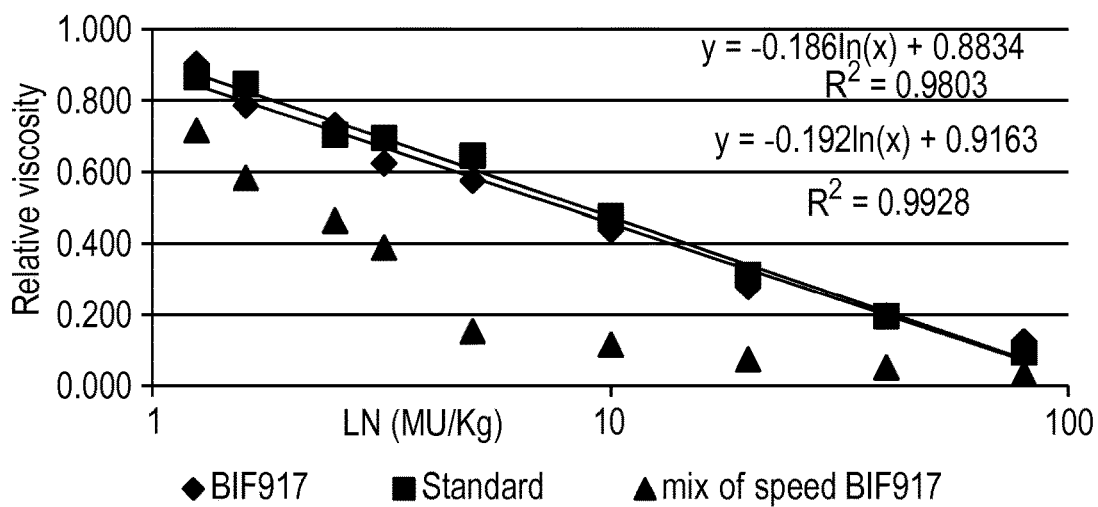
FIG. 2 shows relative viscosity plotted against LN (MU/Kg) for dilutions of Sample I.

The graph in FIG. 2 shows relative viscosity plotted against LN (MU/Kg) for dilutions of Sample 1, standard in which the viscosity was determined using speed 2 on Viscoman. It also show relative viscosity for 1-4 MU/Kg samples of Sample 1 determined with speed 1 and 5-80 MU/Kg samples of Sample 1 determined at speed 2, plotted against LN (MU/Kg).

Additionally, it was also clear that the linear function could only be obtained when having data using same speed on the Viscoman (see FIG. 1). The data has been obtained using the same speed on Viscoman. The low viscous samples are the most relevant for this assay and therefore all samples should be measured using speed 2 meaning that the viscosity is below 400 mPa·s. It was therefore defined that the substrate blank sample should have a viscosity within 60-130 mPa·s when measuring with Viscoman at speed 2.

Quantitative Mannanase Assay:

For setting up a quantitative mannanase assay based on relative viscosity, we used an established control and standard 450 MU/Kg from a colorimetric mannanase assay. The mannanase activity of Sample 1, Sample 2 and the macerating enzyme was determined. Extrapolating the line it is found that the detection limit is ~0.003 MU/Kg for powder (max. 1 g in 10 mL) and 0.0003 MU/Kg for liquid.

Figure 3:
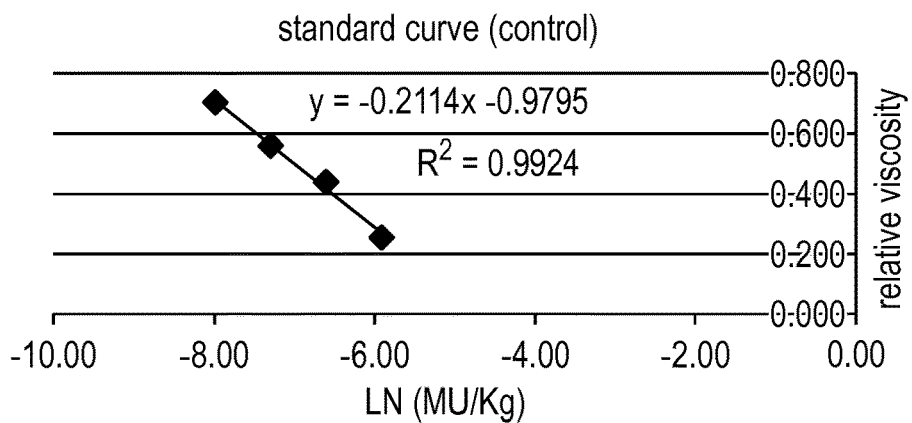
FIG. 3 shows relative viscosity plotted against LN (MU/Kg) for the indicated samples.

Each sample was treated as described in Test 3 but viscosity was determined using Viscoman. A four point standard curve was used to calculate the mannanase activity of each sample. The following Table relates to FIG. 3.

| Sample ID | Act. (MU/Kg) |
|---|---|
| Control | 671.51 |
| Standard | 742.62 |
| Sample 1 | 9.14 |
| Sample 2 | 0.062 |
| Macerating enzyme | 3.089 |

A calculation shows that the mannanase activity in Sample 2 originates mainly from the macerating enzyme (3 MU/Kg divided by 54 corresponding to the dilution when adding the macerating enzyme in the soy media). It can therefore be confirmed that the mannanase gene has been effectively knocked out of the host strain.

Quantitative Cellulase Assay

Figure 4:
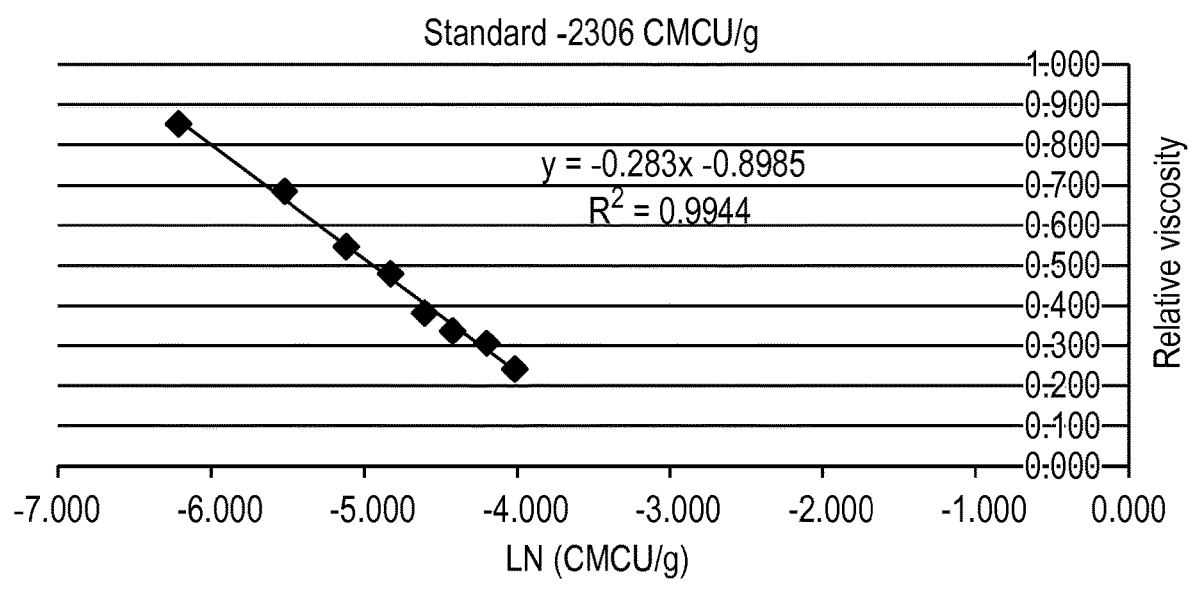
FIG. 4 shows relative viscosity plotted against LN (MU/Kg) for the indicated sample.

The control. 2222 CMCU/g and standard. 2306 CMCU/g was used to set up a quantitative cellulase assay based on relative viscosity. The relative viscosity values for the standard, was plotted against LN (CMCU/g) and confirmed to be linear within the relative viscosity of 0.242-0.885 (see FIG. 4). Extrapolating the line it is found that the detection limit for this assay is 0.002 CMCU/g for liquids and 0.02 CMCU/g for powders.

Two additional samples from fermentations with and one without macerating enzyme were tested for cellulase activity together with the existing Samples. Results show that the knockout of cellulases from the host strain had been effective (34 CMCU/g vs. ~4 CMCU/g) although some activity was still present due to the addition of macerating enzyme in the soy media during fermentation (see Table 6 and FIG. 4).

TABLE 6

| Sample ID | CMCU/g |
|---|---|
| Control | 2414 |
| Sample 1 | 34.38 |
| Sample 2 | 4.1 |
| Standard: fermentation with macerating enzyme, 806 LAU/g | 3.4 |
| Standard: fermentation without macerating enzyme, 971 LAU/g | <0.002 |

Cellulase Threshold Level in Yoghurt Application

In order to establish a cellulase threshold level for yoghurt application, drinking yoghurt was treated with the cellulase control used for the viscosity assay. A drinking yoghurt (MILRAM, Kefir Drink, Erdbeere; BB 14-02-14) was aliquoted 5 mL in Wheaton glasses in duplicated for each sample. A stock dilution of the (0.081 mL in 1000 mL) was further diluted to four new samples by a factor of 10. 100 µL of each sample as well as 100 µL ddH$_2$O for blank samples was added to each of the 5 mL yoghurt. Samples were then either stored at 4° C. or 40° C. At various time points, the viscosity was measured using Viscoman at speed 2.

Relative viscosity was plotted against time (a) hours b) days) incubation at a) 40° C. or b) 4° C. of the dilution sample. For each dilution the CMCU/mL yoghurt is noted.

Figure 5A:
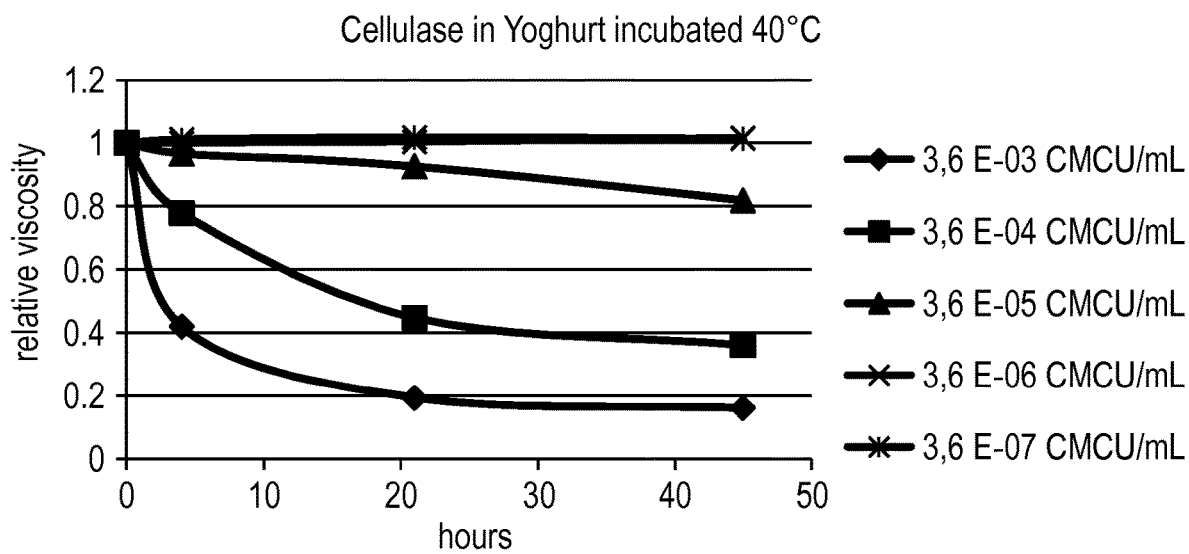
FIG. 5a shows relative viscosity plotted against time for cellulase in yoghurt incubated at 40° C. for the indicated sample.
Figure 5B:
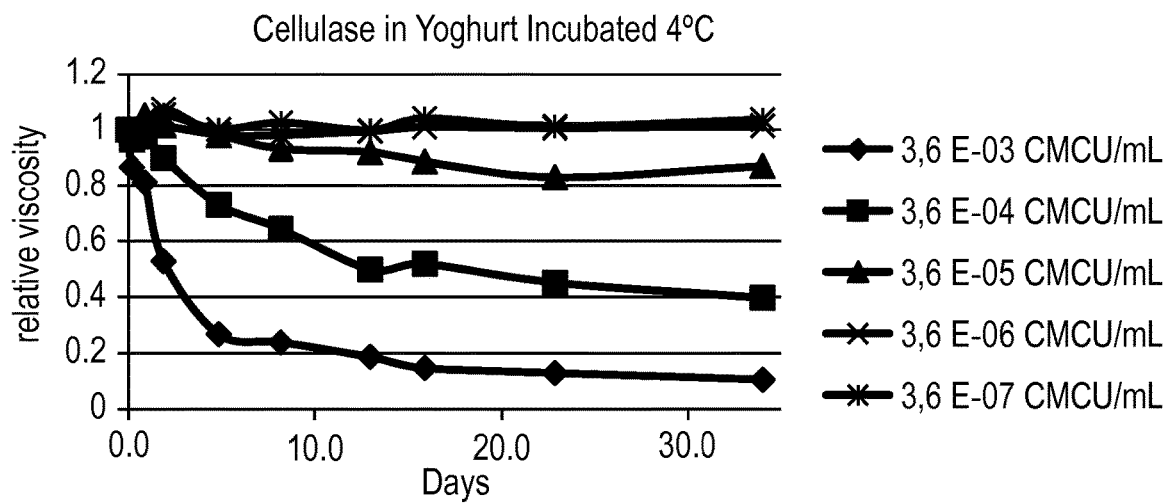
FIG. 5b shows relative viscosity plotted against time for cellulase in yoghurt incubated at 4° C. for the indicated sample.

The results are presented as relative viscosity plotted against time incubated at either 40° C. (FIG. 5*a*) or 4° C. (FIG. 5*b*). The curves show similar development over time, indicating that the 40° C. incubation could be used as an accelerated assay instead of the time consuming 4° C. incubation assay.

In order to calculate threshold levels it was defined that the acceptable level of cellulase activity would reduce the viscosity less than 10% within the time of storage. Based on the data shown in FIG. 5*b* the specific activity (relative viscosity reduction/CMCU/pr. mL yoghurt/h) was calculated for each data point assuming that the highest specific activity observed would represent initial rate.

The highest specific activity was found to be 9.6 relative viscosity reduction/CMCU/pr mL yoghurt/h meaning that the viscosity would be reduced 960% pr. CMCU in one mL yoghurt each hour. The CMCU/mL threshold level allowing for 10% viscosity reduction could then be calculated for various storage periods (see Table 7).

Threshold level=0.1/(specific activity*hours of storage)

For 1 month storage the threshold level is calculated as following; $0.1/(9.6 \times 720) = 1.45 \times 10^{-5}$

TABLE 7

| Cellulase Control. 960% viscosity reduction/h/CMCU/mL | | | |
|---|---|---|---|
| storage time at 4° C. (months) | Hours | Visc reduction × hour | Threshold (CMCU/ml yoghurt) (Max 10% visc. reduction) |
| 9 | 6480 | 62208 | 1.61E−06 |
| 8 | 5760 | 55296 | 1.81E−06 |
| 7 | 5040 | 48384 | 2.07E−06 |
| 6 | 4320 | 41472 | 2.41E−06 |
| 5 | 3600 | 34560 | 2.89E−06 |

TABLE 7-continued

Cellulase Control. 960% viscosity reduction/h/CMCU/mL

| storage time at 4° C. (months) | Hours | Visc reduction × hour | Threshold (CMCU/ml yoghurt) (Max 10% visc. reduction) |
|---|---|---|---|
| 4 | 2880 | 27648 | 3.62E−06 |
| 3 | 2160 | 20736 | 4.82E−06 |
| 2 | 1440 | 13824 | 7.23E−06 |
| 1 | 720 | 6912 | 1.45E−05 |
| 14 days | 336 | 3226 | 3.10E−05 |

Comparing the calculations with the data in FIG. 5b they are found to correlate with the obtained data for all dilutions incubated for a period of 1 month at 4° C. Levels of $3.6 \times 10^{-6}$ CMCU/mL or lower did not reduce the viscosity more than 10% within a month whereas more than $3.6 \times 10^{-6}$ CMCU/mL did reduce the viscosity more than 10%.

CONCLUSION

Pectinase, cellulase and mannanase genes have effectively been knocked out of the host strain.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in chemistry, biochemistry, biology, or related fields are intended to be within the scope of the following claims.

```
List of sequences

>SEQ ID NO: 1 (BIF_917)
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasvtttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt >SEQ ID NO: 2 (BIF_995)
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvaggkisvrvtmideigal >SEQ ID NO: 3 (BIF_1068)
Vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvaggkisvrvtmideigallnysastpvgtp
avlpgsrpavlpdgtvtsanfavhwtkpadtvyntagtvkvpgtatvfgkefkvtatirvq >SEQ ID NO: 4 (BIF_1172)
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvaggkisvrvtmideigallnysastpvgtp
avlpgsrpavlpdgtvtsanfavhwtkpadtvyntagtvkvpgtatvfgkefkvtatirvqrsqvtigssysgnalrltqnipadkqsdtlda
ikdgsttvdantggganpsawtnwayskaghntaeitfeyateqqlgqivmyffrdsnavrfpdagktkiqi
```

```
>SEQ ID NO: 5 (BIF_1241)
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvagqkisvrvtmideigallnysastpvgtp
avlpgsrpavlpdgtvtsanfavhwtkpadtvyntagtvkvpgtatvfgkefkvtatirvqrsqvtigssysgnalrltqnipadkqsdtlda
ikdgsttvdantggganpsawtnwayskaghntaeitfeyateqqlgqivmyffrdsnavrfpdagktkiqisadgknwtdlaatetia
aqessdrvkpytydfapvgatfvkvtvtnadtttpsgvvcagltieielktat >SEQ ID NO: 6 (BIF_1326)
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvagqkisvrvtmideigallnysastpvgtp
avlpgsrpavlpdgtvtsanfavhwtkpadtvyntagtvkvpgtatvfgkefkvtatirvqrsqvtigssysgnalrltqnipadkqsdtlda
ikdgsttvdantggganpsawtnwayskaghntaeitfeyateqqlgqivmyffrdsnavrfpdagktkiqisadgknwtdlaatetia
aqessdrvkpytydfapvgatfvkvtvtnadtttpsgvvcagltieielktatskfvtntsaalssltvngtkvsdsvlaagsyntpaiiadvk
aegegnasvtvlpandnvirvitesedhvtrktftinlgteqef >SEQ ID NO: 7 Bifidobacterium bifidum glycoside hydrolase catalytic core
qnrtsdfdanwkfmlsdsvqaqdpafddsawqqvdlphdysitqkysqsneaesaylpggtgwyrksftidrdlagkriainfdgvy
mnatvwfngvklgthpygyspfsfdltgnakfggentivvkvenrlpssrwysgsgiyrdvtltvtdgvhvgnngvaiktpslatqnggd
vtmnltttkvandteaaanitlkqtvfpkggktdaaigtvttasksiaagasadvtstitaaspklwsiknpnlytvrtevlnggkvldtydtey
gfrwtgfdatsgfslngekvklkgvsmhhdqgslgavanrraierqveilqkmgvnsirtthnpaakalidvcnekgvlvveevfdmw
nrskngntedygkwfgqaiagdnavlggdkdetwakfdltstinrdrnapsvimwslgnemmegisgsysgfpatsaklvawtkaa
dstrpmty >SEQ ID NO: 8 nucleotide sequence encoding full length
gcagttgaagatgcaacaagaagcgatagcacaacacaaatgtcatcaacaccggaagttgtttattcatcagcggtcgatagcaa
acaaaatcgcacaagcgattttgatgcgaactggaaatttatgctgtcagatagcgttcagatagcgtcatttgatgattcag
catggcaacaagttgatctgccgcatgattatagcatcacacagaaatatagccaaagcaatgaagcagaatcagcatatcttccgg
gaggcacaggctggtatagaaaaagctttacaattgatagagatctggcaggcaaacgcattgcgattaattttgatggcgtctatatg
aatgcaacagtctggtttaatggcgttaaactgggcacacatccgtatggctattcaccgttttcatttgatctgacaggcaatgcaaatt
tggcggagaaaacacaattgtcgtcaaagttgaaaatagactgccgtcatcaagatggtattcaggcagcggcatttatagagatgtt
acactgacagttacagatggcgttcatgttggcaataatggcgtcgcaattaaaacaccgtcactggtcaacacaaaatggcggagat
gtcacaatgaacctgacaacaaaagtcgcgaatgatacagaagcagcagcgaacattacactgaaacagacagttttccgaaag
gcggaaaaacggatgcagcaattggcacagttacaacagcatcaaatcaattgcagcaggcgcatcagcagatgttacaagcac
aattacagcagcaagcccgaaactgtggtcaattaaaaaaccgaaactgtatacagttagaacagaagttctgaacggaggcaaa
gttctggatacatatgatacagaatatggctttcgctggacaggctttgatgcaacatcaggcttttcactgaatggcgaaaaagtcaaa
ctgaaaggcgttagcatgcatcatgatcaaggctcactggcgcagttgcaaatagacgcgcaattgaaagacaagtcgaaatcctg
caaaaaatgggcgtcaatagcattcgcacaacacataatccggcagcaaaagcactgattgatgtctgcaatgaaaaaggcgttct
ggttgtcgaagaagtctttgatatgtggaaccgcagcaaaaatggcaacgcggaagattatggcaaatggtttggccaagcaattgc
aggcgataatgcagttctgggaggcgataaagatgaaacatgggcgaaatttgatcttacatcaacaattaaccgcgatagaaatgc
accgtcagttattatgtggtcactgggcaatgaaatgatggaagcatttcaggctcagtttcaggctttccggcaacatcagcaaaact
ggttgcatggacaaaagcagcagattcaacaagaccgatgacatatggcgataacaaaattaaagcgaactggaacgaatcaaat
acaatgggcgataatctgacagcaaatggcggagttgttggcacaaaattattcagatggcgcaaactatgataaaattcgtacaacac
atccgtcatgggcaatttatggctcagaaacagcatcagcgattaataatcgcggtatttataataaacaacggagccacaat
catcagataaacagctgacaagctatgataattcagcagttggctggggagcagttgcatcatcagcatgtatgatgttgttcagaga
gattttgtcgcaggcacatatgtttgacaggatttgattatctgggcgaaccgacaccgtggaatggcacaggctcaggcgcagttgg
ctcatggccgtcaccgaaaaatagctattttggcatcgttgatacagcaggctttccgaaagatacatattattttttatcagagccagtgg
aatgatgatgttcatacactgcatattcttccggcatggaatgaaaatgttgttgcaaaaggctcaggcaataatgttccggttgtcgtttat
acagatgcagcgaaagtgaaactgtattttacaccgaaaggctcaacagaaaaaagactgatcggcgaaagtcgcattcacaaaa
aaacaacagcggcaggctatacatatcaagtctatgaaggcagcgataaagattcaacagcgcataaaaacatgtatctgacatgg
aatgttccgtgggcagaaggcacaattcagcggaagcgtatgatgaaaataatcgcctgattccggaaggcagcacagaaggca
acgcatcagttacaacaacaggcaaagcagcaaaactgaaagcagatgcggatcgcaaaacaattacagcggatggcaaagat
ctgtcatatattgaagtcgatgtcacagatgcaaatggccatattgttccggatcagcaaatagagtcacatttgatgttaaaggcgca
ggcaaactggttggcgttgataatggcgtcatcaccggatcatgattcatatcaagcggataaccgcaaagcattttcaggcaaggtcct
ggcaattgttcagtcaacaaaagaagcaggcgaaattacagttacagcaaaagcagatggcctgcaatcaagcacagttaaaattg
caacaacagcagttccgggaacaagcacagaaaaaacagtccgcagcttttattacagccgcaactattatgtcaaaacaggcaa
caaaccgattctgccgtcagatgttgaagttcgctattcagatggaacaagcgatagacaaaacgttacatgggatgcagtttcagatg
atcaaattgcaaaagcaggctcattttcagttgcaggcacagttgcaggccaaaaaattagcgttcgcgtcacaatgattgatgaaatt
ggcgcactgctgaattattcagcaagcacaccggttggcacaccggcagttcttccgggatcaagaccggcagtcctgccggatggc
```

```
acagtcacatcagcaaattttgcagtccattggacaaaaccggcagatacagtctataatacagcaggcacagtcaaagtaccggg
aacagcaacagttttttggcaaagaatttaaagtcacagcgacaattagagttcaaagaagccaagttacaattggctcatcagtttcag
gaaatgcactgagactgacacaaaaatattccggcagataaacaatcagcactggatgcgattaaagatggctcaacaacagtt
gatgcaaatacaggcggaggcgcaaatccgtcagcatggacaaattgggcatattcaaaagcaggccataacacagcggaaatt
acatttgaatatgcgacagaacaacaactgggccagatcgtcatgtatttthttcgcgatagcaatgcagttagatttccggatgctggca
aaacaaaaattcagatcagcgcagatggcaaaaattggacagatctggcagcaacagaaacaattgcagcgcaagaatcaagc
gatagagtcaaaccgtatacatatgattttgcaccggttggcgcacattttgttaaagtgacagtcacaaacgcagatacaacaacac
cgtcaggcgttgthgcgcaggcctgacagaaattgaactgaaaacagcgacaagcaaattttgtcacaaatacatcagcagcactgt
catcacttacagtcaatggcacaaaagtttcagattcagttctggcagcaggctcatataacacaccggcaattatcgcagatgttaaa
gcggaaggcgaaggcaatgcaagcgttacagtccttccggcacatgataatgttattcgcgtcattacagaaagcgaagatcatgtc
acacgcaaaacatttacaatcaacctgggcacagaacaagaatttccggctgattcagatgaaagagattatccggcagcagatat
gacagtcacagttggctcagaacaaacatcaggcacagcaacagaaggaccgaaaaaattttgcagtcgatggcaacacatcaac
atattggcatagcaattggacaccgacaacagttaatgatctgtcggatcgcgtttgaactgcaaaaaccgacaaaactggatgcactg
agatatcttccgcgtccggcaggctcaaaaaatggcagcgtcacagaatataaagttcaggtgtcagatgatggaacaaactggac
agatgcaggctcaggcacatggacaacggattatggctggaaactggcggaatttaatcaaccggtcacaacaaaacatgttagac
tgaaagcggttcatacatatgcagatagcggcaacgataaaatttatgagcgcaagcgaaattagactgagaaaagcggtcgataca
acggatatttcaggcgcaacagttacagttccggcaaaactgacagttgatagagttgatgcagatcatccggcaacatttgcaacaa
aagatgtcacagttacactgggagatgcaacactgagatatggcgttgattatctgctggattatgcaggcaatacagcagttggcaaa
gcaacagtgacagttagaggcattgataaatattcaggcacagtcgcgaaaacatttacaattgaactgaaaaatgcaccggcacc
ggaaccgacactgacatcagttagcgtcaaaacaaaaccggcaaactgacatatgttgtcggagatgcatttgatccggcaggcct
ggttctgcaacatgatagacaagcagatagacctccgcaaccgctggttggcgaacaagcggatgaacgcggactgacatgcggc
acaagatgcgatagagttgaacaactgcgcaaacatgaaaatagagaagcgcatagaacaggcctggatcatctggaatttgttgg
cgcagcagatggcgcagttggagaacaagcaacatttaaagtccatgtccatgcagatcagggagatggcagacatgatgatgca
gatgaacgcgatattgatccgcatgttccggtcgatcatgcagttggcgaactggcaagagcagcatgccatcatgttattggcctgag
agtcgatacacatagacttaaagcaagcggctttcaaattccggctgatgatatggcagaaatcgatcgcattacaggctttcatcgtttt
gaacgccatgtc >SEQ ID NO: 9 nucleotide sequence encoding BIF_917
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagcatg
gcaacaagttgatctgccgcatgattatagcatcacacagaaatatagccaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatggctattcaccgttttcatttgatctgacaggcaatgcaaaatttggc
ggagaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcagcaattggcacagttacaacagcatcaaaatcaattgcagcaggcgcatcagcagatgttacaagcacaatt
acagcagcaagcccgaaactgtggtcaattaaaaaacccgaacctgtatacagttagaacagaagttctgaacggaggcaaagttct
ggatacatatgatacagaatatggctttcgctggacaggctttgatgcaacatcaggcttttcactgaatggcgaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtctttgatatgtggaaccgcagcaaaaatggcaacacggaagattatggcaaatggtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaaggcatttcaggctcagtttcaggctttccggcaacatcagcaaaactggttg
catggacaaaagcagcagattcaacaagaccgatgacatatggcgataacaaaatttaaagcgaactggaacagataacataacaa
tgggcgataatctgacagcaaatggcggagttgttggcacaaatttattcagtggcgcaaactatgataaaattcgtacaacacatcc
gtcatgggcaatttatggctcagaaacagcatcagcgattaatagccgtggcatttataatagaacaacaggcggagcacaatcatc
agataaacagctgacaagctatgataattcagcagttggctggggagcagttgcatcatcagcatggtatgatgttgttcagagagattt
tgtcgcaggcacatatgtttggacaggattttgattatctgggcgaacagaccgtcaggcgcagttggctcat
ggccgtcaccgaaaaatagctatttttggcatcgttgatacagcaggctttccgaaagatacatattatttttatcagagccagtggaatga
tgatgttcatacactgcatattcttccggcatggaatgaaaatgttgttgcaaaaggctcaggcaataatgttccggttgtcgtttatacaga
tgcagcgaaagtgaaactgtattttacaccgaaaggctcaacagaaaaagactgatcggcgaaaaatcatttacaaaaaaaaca
acagcggcaggctatacatatcaagtctatgaaggcagcgataaagattcaacagcgcataaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcacatttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaaca >SEQ ID NO: 10 nucleotide sequence encoding BIF_995
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagcatg
gcaacaagttgatctgccgcatgattatagcatcacacagaaatatagccaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatggctattcaccgttttcatttgatctgacaggcaatgcaaaatttggc
ggagaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcagcaattggcacagttacaacagcatcaaaatcaattgcagcaggcgcatcagcagatgttacaagcacaatt
acagcagcaagcccgaaactgtggtcaattaaaaaacccgaacctgtatacagttagaacagaagttctgaacggaggcaaagttct
ggatacatatgatacagaatatggctttcgctggacaggctttgatgcaacatcaggcttttcactgaatggcgaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtctttgatatgtggaaccgcagcaaaaatggcaacacggaagattatggcaaatggtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaaggcatttcaggctcagtttcaggctttccggcaacatcagcaaaactggttg
```

```
catggacaaaagcagcagattcaacaagaccgatgacatatggcgataacaaaattaaagcgaactggaacgaatcaaatacaa
tgggcgataatctgacagcaaatggcggagttgttggcacaaattattcagatggcgcaaactatgataaaattcgtacaacacatcc
gtcatgggcaatttatggctcagaaacagcatcagcgattaatagccgtggcatttataatagaacaacaggcggagcacaatcatc
agataaacagctgacaagctatgataattcagcagttggctggggagcagttgcatcatcagcatggtatgatgttgttcagagagattt
tgtcgcaggcacatatgtttggacaggatttgattatctgggcgaaccgacaccgtggaatggcacaggctcaggcgcagttggctcat
ggccgtcaccgaaaaatagctatttggcatcgttgatacagcaggctttccgaaagatacatattatttttatcagagccagtggaatga
tgatgttcatacactgcatattcttccggcatggaatgaaaatgttgttgcaaaaggctcaggcaataatgttccggttgtcgtttatacaga
tgcagcgaaagtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcacatttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaacagtccgcagcttttattacagccgcaactattatgtcaaaacaggcaacaaac
cgattctgccgtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatgaaattggcgc
actg >SEQ ID NO: 11 nucleotide sequence encoding BIF_1068
gttgaagatgcaacaagaagcgatagcacaacacaaatgtcatcaacaccggaagttgtttattcatcagcggtcgatagcaaaca
aaatcgcacaagcgatttgatgcgaactggaaatttatgctgtcagatagcgttcaagcacaagatccggcatttgatgattcagcatg
gcaacaagttgatctgccgcatgattatagcatcacacagaaatatagccaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatgctattcaccgttttcatttgatctgacaggcaatgcaaaatttggc
ggagaaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcagcaattggcacagttacaacagcatcaaaatcaattgcacgaggcgcatcagcagatgttacaagcacaatt
acagcagcaagcccgaaactgtggtcaattaaaaaacccgaacctgtatacagttagaacagaagttctgaacggaggcaaagttct
ggatacatatgatacagaatatggctttcgctggacaggctttgatgcaacatcaggcttttcactgaatggcgaaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtctttgatatgtggaaccgcagcaaaaatggcaacacggaagattatggcaaatggtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaaggcatttcaggctcagtttcaggctttccggcaacatcagcaaaactggttg
catggacaaaagcagcagattcaacaagaccgatgacatatggcgataacaaaattaaagcgaactggaacgaatcaaatacaa
tgggcgataatctgacagcaaatggcggagttgttggcacaaattattcagatggcgcaaactatgataaaattcgtacaacacatcc
gtcatgggcaatttatggctcagaaacagcatcagcgattaatagccgtggcatttataatagaacaacaggcggagcacaatcatc
agataaacagctgacaagctatgataattcagcagttggctggggagcagttgcatcatcagcatggtatgatgttgttcagagagattt
tgtcgcaggcacatatgtttggacaggatttgattatctgggcgaaccgacaccgtggaatggcacaggctcaggcgcagttggctcat
ggccgtcaccgaaaaatagctatttggcatcgttgatacagcaggctttccgaaagatacatattatttttatcagagccagtggaatga
tgatgttcatacactgcatattcttccggcatggaatgaaaatgttgttgcaaaaggctcaggcaataatgttccggttgtcgtttatacaga
tgcagcgaaagtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcacatttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaacagtccgcagcttttattacagccgcaactattatgtcaaaacaggcaacaaac
cgattctgccgtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatgaaattggcgc
actgctgaattattcagcaagcacaccggttggcacaccggcagttcttccgggatcaagaccggcagtcctgccggatggcacagt
cacatcagcaaattttgcagtccattggacaaaaccggcagatacagtctataatacagcaggcagtcaaagtaccgggaacag
caacagthttggcaaagaatttaaagtcacagcgacaattagagttcaa >SEQ ID NO: 12 nucleotide sequence encoding BIF_1172
gttgaagatgcaacaagaagcgatagcacaacacaaatgtcatcaacaccggaagttgtttattcatcagcggtcgatagcaaaca
aaatcgcacaagcgatttgatgcgaactggaaatttatgctgtcagatagcgttcaagcacaagatccggcatttgatgattcagcatg
gcaacaagttgatctgccgcatgattatagcatcacacagaaatatagccaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatgctattcaccgttttcatttgatctgacaggcaatgcaaaatttggc
ggagaaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcagcaattggcacagttacaacagcatcaaaatcaattgcacgaggcgcatcagcagatgttacaagcacaatt
acagcagcaagcccgaaactgtggtcaattaaaaaacccgaacctgtatacagttagaacagaagttctgaacggaggcaaagttct
ggatacatatgatacagaatatggctttcgctggacaggctttgatgcaacatcaggcttttcactgaatggcgaaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtctttgatatgtggaaccgcagcaaaaatggcaacacggaagattatggcaaatggtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaaggcatttcaggctcagtttcaggctttccggcaacatcagcaaaactggttg
catggacaaaagcagcagattcaacaagaccgatgacatatggcgataacaaaattaaagcgaactggaacgaatcaaatacaa
tgggcgataatctgacagcaaatggcggagttgttggcacaaattattcagatggcgcaaactatgataaaattcgtacaacacatcc
gtcatgggcaatttatggctcagaaacagcatcagcgattaatagccgtggcatttataatagaacaacaggcggagcacaatcatc
```

```
agataaacagctgacaagctatgataattcagcagttggctggggagcagttgcatcatcagcatggtatgatgttgttcagagagattt
tgtcgcaggcacatatgtttggacaggatttgattatctgggcgaaccgacaccgtggaatggcacaggctcaggcgcagttggctcat
ggccgtcaccgaaaaatagctattttggcatcgttgatacagcagcttttccgaaagatacatattattttttatcagagccagtggaatga
tgatgttcatacactgcatattcttccggcatggaatgaaaatgttgttgcaaaaggctcaggcaataatgttccggttgtcgtttatacaga
tgcagcgaaagtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcacatttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaacagtccgcagcttttattacagccgcaactattatgtcaaaacaggcaacaaac
cgattctgccgtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatgaaattggcgc
actgctgaattattcagcaagcacaccggttggcacaccggcagttcttccgggatcaagaccggcagtcctgccggatggcacagt
cacatcagcaaattttgcagtccattggacaaaaccggcagatacagtctataatacagcaggcacagtcaaagtaccgggaacag
caacagthttggcaaagaatttaaagtcacagcgacaattagagttcaaagaagccaagttacaattggctcatcagtttcaggaaat
gcactgagactgacacaaaatattccggcagataaacaatcagatacactggatgcgattaaagatggctcaacaacagttgatgc
aaatacaggcggaggcgcaaatccgtcagcatggacaaattgggcatattcaaaagcaggccataacacagcggaaattacatttt
gaatatgcgacagaacaacaactgggccagatcgtcatgtatttthttcgcgatagcaatgcagttagatttccggatgctggcaaaac
aaaaattcagatc >SEQ ID NO: 13 nucleotide sequence encoding BIF_1241
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagcatg
gcaacaagttgatctgccgcatgattatagcatcacacagaaatatagcaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatgctattcaccgttttcatttgatctgacaggcaatgcaaaatttggc
ggagaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcaacaattggcacagttacaacagcatcaaaatcaattgcagcaggcgcatcagcagatgttacaagcacaatt
acagcagcaagcccgaaactgtggtcaattaaaaaacccgaacctgtatacagttagaacagaagttctgaacggaggcaaagttct
ggatacatatgatacagaatatggctttcgctggacaggctttgatgcaacatcaggcttttcactgaatggcaaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtcttttgatatgtggaaccgcagcaaaaatggcaacacggaagattatggcaaagttgtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaagcattcaggctcagtttcaggctttccggcaacatcagcaaaactggttg
catggacaaaagcagcagattcaacaagaccgatgacatatggcgataacaaaattaaagcgaactggaacgaatcaaatacaa
tgggcgataatctgacagcaaatggcggagttgttggcacaaattattcagtggcgcaaacatgataaaattcgtacaacacatcc
gtcatgggcaatttatggctcagaaacagcatcagcgattaatagccgtggcatttataatagaacaacaggcggagcacaatcatc
agataaacagctgacaagctatgataattcagcagttggctggggagcagttgcatcatcagcatggtatgatgttgttcagagagattt
tgtcgcaggcacatatgtttggacaggatttgattatctgggcgaaccgacaccgtggaatggcacaggctcaggcgcagttggctcat
ggccgtcaccgaaaaatagctattttggcatcgttgatacagcagcttttccgaaagatacatattattttttatcagagccagtggaatga
tgatgttcatacactgcatattcttccggcatggaatgaaaatgttgttgcaaaaggctcaggcaataatgttccggttgtcgtttatacaga
tgcagcgaaagtgaaactgtattttacaccgaaaggctcaacagaaaaaagactgatcggcgaaaaatcatttacaaaaaaaaca
acagcggcaggctatacatatcaagtctatgaaggcagcgataaagattcaacagcgcataaaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcacatttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaacagtccgcagcttttattacagccgcaactattatgtcaaaacaggcaacaaac
cgattctgccgtcagatgttgaagttcgctattcagatggaacaagcgatagacaaaacgttacatgggatgcagtttcagatgatcaa
attgcaaaagcaggctcattttcagttgcaggcacagttgcaggccaaaaaattagcgttcgcgtcacaatgattgatgaaattggcgc
actgctgaattattcagcaagcacaccggttggcacaccggcagttcttccgggatcaagaccggcagtcctgccggatggcacagt
cacatcagcaaattttgcagtccattggacaaaaccggcagatacagtctataatacagcaggcacagtcaaagtaccgggaacag
caacagthttggcaaagaatttaaagtcacagcgacaattagagttcaaagaagccaagttacaattggctcatcagtttcaggaaat
gcactgagactgacacaaaatattccggcagataaacaatcagatacactggatgcgattaaagatggctcaacaacagttgatgc
aaatacaggcggaggcgcaaatccgtcagcatggacaaattgggcatattcaaaagcaggccataacacagcggaaattacatttt
gaatatgcgacagaacaacaactgggccagatcgtcatgtatttthttcgcgatagcaatgcagttagatttccggatgctggcaaaac
aaaaattcagatcagcgcagatggcaaaaattggacagatctggcagcaacagaaacaattgcagcgcaagaatcaagcgatag
agtcaaaccgtatacatatgattttgcaccggttggcgcaacatttgttaaagtgacagtcacaaacgcagatacaacaacaccgtca
ggcgttgtttgcgcaggcctgacagaaaattgaactgaaaacagcgaca >SEQ ID NO: 14 nucleotide sequence encoding BIF_1326
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagcatg
gcaacaagttgatctgccgcatgattatagcatcacacagaaatatagcaaagcaatgaagcagaatcagcatatcttccgggag
gcacaggctggtatagaaaaagctttacaattgatagagatctggcaggcaaacgcattgcgattaattttgatggcgtctatatgaatg
caacagtctggtttaatggcgttaaactgggcacacatccgtatgctattcaccgttttcatttgatctgacaggcaatgcaaaatttggc
ggagaaaacacaattgtcgtcaaagttgaaaatagactgccgtcatcaagatggtattcaggcagcggcatttatagagatgttacact
gacagttacagatggcgttcatgttggcaataatggcgtcgcaattaaaacaccgtcactggcaacacaaaatggcggagatgtcac
aatgaacctgacaacaaaagtcgcgaatgatacagaagcagcagcgaacattacactgaaacagacagttttttccgaaaggcgg
aaaaacggatgcagcaattggcacagttacaacagcatcaaaatcaattgcagcaggcgcatcagcagatgttacaagcacaatt
acagcagcaagcccgaaactgtggtcaattaaaaaacccgaacctgtatacagttagaacagaagttctgaacggaggcaaagttct
```

-continued

List of sequences

```
ggatacatatgatacagaatatggctttcgctggacaggctttgatgcaacatcaggcttttcactgaatggcgaaaaagtcaaactga
aaggcgttagcatgcatcatgatcaaggctcacttggcgcagttgcaaatagacgcgcaattgaaagacaagtcgaaatcctgcaa
aaaatgggcgtcaatagcattcgcacaacacataatccggcagcaaaagcactgattgatgtctgcaatgaaaaaggcgttctggtt
gtcgaagaagtcttttgatatgtggaaccgcagcaaaaatggcaacacggaagattatggcaaatggtttggccaagcaattgcaggc
gataatgcagttctgggaggcgataaagatgaaacatgggcgaaatttgatcttacatcaacaattaaccgcgatagaaatgcaccgt
cagttattatgtggtcactgggcaatgaaatgatggaaggcatttcaggctcagtttcaggctttccggcaacatcagcaaaactggttg
catggacaaaagcagcagattcaacaagaccgatgacatatggcgataacaaaattaaagcgaactggaacgaatcaaatacaa
tgggcgataatctgacagcaaatggcggagttgttggcacaaattattcagatggcgcaaactatgataaaattcgtacaacacatcc
gtcatgggcaatttatggctcagaaacagcatcagcgattaatagccgtggcatttataatagaacaacaggcggagcacaatcatc
agataaacagctgacaagctatgataattcagcagttggctggggagcagttgcatcatcagcatggtatgatgttgttcagagagattt
tgtcgcaggcacatatgtttggacaggatttgattatctgggcgaaccgacaccgtggaatggcacaggctcaggcgcagttggctcat
ggccgtcaccgaaaaatagctattttggcatcgttgatacagcaggctttccgaaagatacatattattttatcagagccagtggaatga
tgatgttcatacactgcatattcttccggcatgaatgaaaatgttgttgcaaaaggctcaggcaataatgttccggttgtcgtttatacaga
tgcagcgaaagtgaaactgtattttacaccgaaaggctcaacagaaaaagactgatcggcgaaaatcatttacaaaaaaaaca
acagcggcaggctatacatatcaagtctatgaaggcagcgataaagattcaacagcgcataaaaacatgtatctgacatggaatgtt
ccgtgggcagaaggcacaatttcagcggaagcgtatgatgaaaataatcgcctgattccggaaggcagcacagaaggcaacgca
tcagttacaacaacaggcaaagcagcaaaactgaaagcagatgcggatcgcaaaacaattacagcggatggcaaagatctgtca
tatattgaagtcgatgtcacagatgcaaatggccatattgttccggatgcagcaaatagagtcactttgatgttaaaggcgcaggcaa
actggttggcgttgataatggctcatcaccggatcatgattcatatcaagcggataaccgcaaagcattttcaggcaaagtcctggcaat
tgttcagtcaacaaaagaagcaggcgaaattacagttacagcaaaagcagatggcctgcaatcaagcacagttaaaattgcaaca
acagcagttccgggaacaagcacagaaaaaacagtccgcagcttttattacagccgcaactattatgtcaaaacaggcaacaaac
cgattctgccgtcagatgttgaagttcgctattcagatgaacaagcgatagacaaaacgttacatgggatgcagtttcagatgatcaa
attgcaaaagcaggctcattttcagttgcaggcacagttgcaggccaaaaaattagcgttcgcgtcacaatgattgatgaaattggcgc
actgctgaattattcagcaagcacaccggttggcacaccggcagttcttccggatgcaggcagtccttgccggatggcacagt
cacatcagcaaattttgcagtccattggacaaaaccggcagatacagtctataatacagcaggcacagtcaaagtaccggtagacag
caacagthttggcaaagaatttaaagtcacagcgacaattagagttcaaagaagccaagttacaattggctcatcagtttcaggaaat
gcactgagactgacacaaaatattccggcagataaacaatcagatacactggatgcgattaaagatggctcaacaacagttgatgc
aaatacaggcggaggcgcaaatccgtcagcatggacaaattggccatattcaaaagcaggccataacagcggaaattacattt
gaatatgcgacagaacaacaactgggccagatcgtcatgtattthttcgcgatagcaatgcagttagatttccggatgctggcaaaac
aaaaattcagatcagcgcagatggcaaaaattggacagatctggcagcaacagaaacaattgcagcgcaagaatcaagcgatag
agtcaaaccgtatacatatgattttgcaccggttggcgcaacatttgttaaagtgacagtcacaaacgcagatacaacaacaccgtca
ggcgttgtttgcgcaggcctgacagaaattgaactgaaaacagcgacaagcaaatttgtcacaaatacatcagcagcactgtcatca
cttacagtcaatggcacaaaagtttcagattcagttctggcagcaggctcatataacacaccggcaattatcgcagatgttaaagcgga
aggcgaaggcaatgcaagcgttacagtcctccggcacatgataatgttattcgcgtcattacagaaagcgaagatcatgtcacacgc
aaacatttacaatcaacctgggcacagaacaagaattt
```

>SEQ ID NO: 15 forward primer for generation of BIF variants
GGGGTA<u>ACTAGT</u>GGAAGATGCAACAAGAAG >SEQ ID NO: 16 reverse primer for BIF917
GCGCTTAATTAATTATGTTTTTTCTGTGCTTGTTC >SEQ ID NO: 17 reverse primer for BIF995
GCGCTTAATTAATTACAGTGCGCCAATTTCATCAATCA >SEQ ID NO: 18 reverse primer for BIF1068
GCGCTTAATTAATTATTGAACTCTAATTGTCGCTG >SEQ ID NO: 19 reverse primer for BIF1241
GCGCTTAATTAATTATGTCGCTGTTTTCAGTTCAAT >SEQ ID NO: 20 reverse primer for BIF1326
GCGCTTAATTAATTAAAATTCTTGTTCTGTGCCCA >SEQ ID NO: 21 reverse primer for BIF1478
GCGCTTAATTAATTATCTCAGTCTAATTTCGCTTGCGC >SEQ ID NO: 22 *Bifidobacterium bifidum* BIF1750
vedatrsdsttqmsstpevvyssavdskqnrtsdfdanwkfmlsdsvqaqdpafddsawqqvdlphdysitqkysqsneaesayl
pggtgwyrksftidrdlagkriainfdgvymnatvwfngvklgthpygyspfsfdltgnakfggentivvkvenrlpssrwysgsgiyrdv
tltvtdgvhvgnngvaiktpslatqnggdytmnltttkvandteaaanitlkqtvfpkggktdaaigtvttasksiaagasadvtstitaaspk
lwsiknpnlytvrtevlnggkvldtydteygfrwtgfdatsgfslngekvklkgvsmhhdqgslgavanrraierqveilqkmgvnsirtth
npaakalidvcnekgvlvveevfdmwnrskngntedygkwfgqaiagdnavlggdkdetwakfdltstinrdrnapsvimwslgne
mmegisgsysgfpatsaklvawtkaadstrpmtygdnkikanwnesntmgdnltanggvvgtnysdganydkirtthpswaiygs
etasainsrgiynrttggaqssdkqltsydnsavgwgavassawydvvqrdfvagtyvwtgfdylgeptpwngtgsgavgswpspk
nsyfgivdtagfpkdtyyfyqsqwnddvhtlhilpawnenvvakgsgnnvpvvvytdaakvklyftpkgstekrligeksftkkttaagyt
yqvyegsdkdstahknmyltwnvpwaegtisaeaydennrlipegstegnasytttgkaaklkadadrktitadgkdlsyievdvtda
nghivpdaanrvtfdvkgagklvgvdngsspdhdsyqadnrkafsgkvlaivqstkeageitvtakadglqsstvkiattavpgtstekt
vrsfyysrnyyvktgnkpilpsdvevrysdgtsdrqnvtwdaysddqiakagsfsvagtvagqkisvrvtmideigallnysastpvgtp
avlpgsrpavlpdgtvtsanfavhwtkpadtvyntagtvkvpgtatvfgkefkvtatirvqrsqvtigssysgnalrltqnipadkqsdtlda
ikdgsttvdantgggangpsawtnwayskaghntaeitfeyateqqlgqivmyffrdsnavrfpdagktkiqisadgknwtdlaatetia
aqessdrvkpytydfapvgatfvkvtvtnadttttpsgvvcagltelelktatskfvtntsaalssltvngtkvsdsvlaagsyntpaiiadvk
aegegnasvtvlpandnvirvitesedhvtrktftinlgteqefpadsderdypaadmtvtgseqtsgtategpkkfavdgntstywh
snwtpttyndlwiafelqkptkldalrylprpagsknngsvteykvqvsddgtnwtdagsgtwttdygwklaefnqpvtkhvrlkavhty
adsgndkfmsaseirlrkavdttdisgatvtvpakltvdrvdadhpatfatkdvtvtlgdatlrygvdylldyagntavgkatvtvrgidkys
```

List of sequences gtvaktftielknapapeptltsysyktkpskltyvvgdafdpaglvlqhdrqadrppqplvgeqadergltcgtrcdrveqlrkhenreah
rtgldhlefvgaadgavgeqatfkvhvhadqgdgrhddaderdidphypvdhavgelaraachhviglrvdthrlkasgfqipaddm
aeidritgfhrferhvg >SEQ ID NO: 23 The signal sequence of extracellular lactase from *Bifidobacterium bifidum* DSM20215
Vrskklwisllfalaliftmafgstssaqa

SEQUENCE LISTING

<160> NUMBER OF SEQ ID NOS: 23

<210> SEQ ID NO 1
<211> LENGTH: 887
<212> TYPE: PRT
<213> ORGANISM: Artificial Sequence
<220> FEATURE:
<223> OTHER INFORMATION: Truncated lactase fragment

<400> SEQUENCE: 1

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
```

-continued

```
                275                 280                 285
Gly Lys Val Leu Asp Thr Tyr Asp Thr Glu Tyr Gly Phe Arg Trp Thr
290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
                340                 345                 350
Gly Val Asn Ser Ile Arg Thr Thr His Asn Pro Ala Ala Lys Ala Leu
                355                 360                 365
Ile Asp Val Cys Asn Glu Lys Gly Val Leu Val Glu Glu Val Phe
370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
                420                 425                 430
Asp Arg Asn Ala Pro Ser Val Ile Met Trp Ser Leu Gly Asn Glu Met
                435                 440                 445
Met Glu Gly Ile Ser Gly Ser Val Ser Gly Phe Pro Ala Thr Ser Ala
450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
                500                 505                 510
Asp Gly Ala Asn Tyr Asp Lys Ile Arg Thr Thr His Pro Ser Trp Ala
                515                 520                 525
Ile Tyr Gly Ser Glu Thr Ala Ser Ala Ile Asn Ser Arg Gly Ile Tyr
                530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
                595                 600                 605
Gly Ala Val Gly Ser Trp Pro Ser Pro Lys Asn Ser Tyr Phe Gly Ile
                610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val Val
                660                 665                 670
Tyr Thr Asp Ala Ala Lys Val Lys Leu Tyr Phe Thr Pro Lys Gly Ser
                675                 680                 685
Thr Glu Lys Arg Leu Ile Gly Glu Lys Ser Phe Thr Lys Lys Thr Thr
690                 695                 700
```

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735

Gly Thr Ile Ser Ala Glu Ala Tyr Asp Glu Asn Asn Arg Leu Ile Pro
        740                 745                 750

Glu Gly Ser Thr Glu Gly Asn Ala Ser Val Thr Thr Thr Gly Lys Ala
    755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr
                885

<210> SEQ ID NO 2
<211> LENGTH: 965
<212> TYPE: PRT
<213> ORGANISM: Artificial Sequence
<220> FEATURE:
<223> OTHER INFORMATION: Truncated lactase fragment

<400> SEQUENCE: 2

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

```
Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
        210                 215                 220

Thr Leu Lys Gln Thr Val Phe Pro Lys Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
        290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
        530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590
```

Gly Phe Asp Tyr Leu Gly Glu Pro Thr Pro Trp Asn Gly Thr Gly Ser
                595                 600                 605

Gly Ala Val Gly Ser Trp Pro Ser Pro Lys Asn Ser Tyr Phe Gly Ile
610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala
        755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
    835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu
                965

<210> SEQ ID NO 3
<211> LENGTH: 1038
<212> TYPE: PRT
<213> ORGANISM: Artificial Sequence
<220> FEATURE:
<223> OTHER INFORMATION: Truncated lactase fragment

<400> SEQUENCE: 3

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
```

-continued

```
                405                 410                 415
Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
            450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
            690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala
            755                 760                 765

Ala Lys Leu Lys Ala Asp Ala Asp Arg Lys Thr Ile Thr Ala Asp Gly
            770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830
```

-continued

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
        1010                1015                1020

Val Phe Gly Lys Glu Phe Lys Val Thr Ala Thr Ile Arg Val Gln
        1025                1030                1035

<210> SEQ ID NO 4
<211> LENGTH: 1142
<212> TYPE: PRT
<213> ORGANISM: Artificial Sequence
<220> FEATURE:
<223> OTHER INFORMATION: Truncated lactase fragment

<400> SEQUENCE: 4

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

```
Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ala Trp
                565                 570                 575
```

-continued

```
Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val  His Trp Thr Lys Pro  Ala Asp Thr
```

```
            995                 1000                1005
Val Tyr Asn Thr Ala Gly Thr Val Lys Val Pro Gly Thr Ala Thr
            1010                1015                1020

Val Phe Gly Lys Glu Phe Lys Val Thr Ala Thr Ile Arg Val Gln
            1025                1030                1035

Arg Ser Gln Val Thr Ile Gly Ser Ser Val Ser Gly Asn Ala Leu
            1040                1045                1050

Arg Leu Thr Gln Asn Ile Pro Ala Asp Lys Gln Ser Asp Thr Leu
            1055                1060                1065

Asp Ala Ile Lys Asp Gly Ser Thr Thr Val Asp Ala Asn Thr Gly
            1070                1075                1080

Gly Gly Ala Asn Pro Ser Ala Trp Thr Asn Trp Ala Tyr Ser Lys
            1085                1090                1095

Ala Gly His Asn Thr Ala Glu Ile Thr Phe Glu Tyr Ala Thr Glu
            1100                1105                1110

Gln Gln Leu Gly Gln Ile Val Met Tyr Phe Phe Arg Asp Ser Asn
            1115                1120                1125

Ala Val Arg Phe Pro Asp Ala Gly Lys Thr Lys Ile Gln Ile
            1130                1135                1140

<210> SEQ ID NO 5
<211> LENGTH: 1211
<212> TYPE: PRT
<213> ORGANISM: Artificial Sequence
<220> FEATURE:
<223> OTHER INFORMATION: Truncated lactase fragment

<400> SEQUENCE: 5

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65              70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Val Lys Val Glu Asn Arg
145             150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
```

```
            210                 215                 220
Thr Leu Lys Gln Thr Val Phe Pro Lys Gly Lys Thr Asp Ala Ala
225                 230                 235                 240

Ile Gly Thr Val Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
                275                 280                 285

Gly Lys Val Leu Asp Thr Tyr Asp Thr Glu Tyr Gly Phe Arg Trp Thr
                290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
                355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
                450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
                515                 520                 525

Ile Tyr Gly Ser Glu Thr Ala Ser Ala Ile Asn Ser Arg Gly Ile Tyr
                530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
                595                 600                 605

Gly Ala Val Gly Ser Trp Pro Ser Pro Lys Asn Ser Tyr Phe Gly Ile
                610                 615                 620

Val Asp Thr Ala Gly Phe Pro Lys Asp Thr Tyr Tyr Phe Tyr Gln Ser
625                 630                 635                 640
```

-continued

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
                690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
                755                 760                 765

Ala Lys Leu Lys Ala Asp Ala Asp Arg Lys Thr Ile Thr Ala Asp Gly
                770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
                835                 840                 845

Val Gln Ser Thr Lys Glu Ala Gly Glu Ile Thr Val Thr Ala Lys Ala
                850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
                915                 920                 925

Ala Val Ser Asp Asp Gln Ile Ala Lys Ala Gly Ser Phe Ser Val Ala
                930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val His Trp Thr Lys Pro Ala Asp Thr
                995                 1000                1005

Val Tyr Asn Thr Ala Gly Thr Val Lys Val Pro Gly Thr Ala Thr
                1010                1015                1020

Val Phe Gly Lys Glu Phe Lys Val Thr Ala Thr Ile Arg Val Gln
                1025                1030                1035

Arg Ser Gln Val Thr Ile Gly Ser Ser Val Ser Gly Asn Ala Leu
                1040                1045                1050

```
Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr
    1205                1210

<210> SEQ ID NO 6
<211> LENGTH: 1296
<212> TYPE: PRT
<213> ORGANISM: Artificial Sequence
<220> FEATURE:
<223> OTHER INFORMATION: Truncated lactase fragment

<400> SEQUENCE: 6

Val Glu Asp Ala Thr Arg Ser Asp Ser Thr Thr Gln Met Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Ser Val Gln
            35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190
```

-continued

```
Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Asn Ile
210                 215                 220

Thr Leu Lys Gln Thr Val Phe Pro Lys Gly Lys Thr Asp Ala Ala
225                 230                 235                 240

Ile Gly Thr Val Thr Thr Ala Ser Lys Ser Ile Ala Ala Gly Ala Ser
                    245                 250                 255

Ala Asp Val Thr Ser Thr Ile Thr Ala Ser Pro Lys Leu Trp Ser
                260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                    325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
```

-continued

```
              610                 615                 620
Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                    645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                    725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val His Trp Thr Lys Pro Ala Asp Thr
                995                 1000                1005

Val Tyr Asn Thr Ala Gly Thr Val Lys Val Pro Gly Thr Ala Thr
        1010                1015                1020

Val Phe Gly Lys Glu Phe Lys Val Thr Ala Thr Ile Arg Val Gln
        1025                1030                1035
```

```
Arg Ser Gln Val Thr Ile Gly Ser Ser Val Ser Gly Asn Ala Leu
    1040            1045                1050

Arg Leu Thr Gln Asn Ile Pro Ala Asp Lys Gln Ser Asp Thr Leu
    1055            1060                1065

Asp Ala Ile Lys Asp Gly Ser Thr Thr Val Asp Ala Asn Thr Gly
    1070            1075                1080

Gly Gly Ala Asn Pro Ser Ala Trp Thr Asn Trp Ala Tyr Ser Lys
    1085            1090                1095

Ala Gly His Asn Thr Ala Glu Ile Thr Phe Glu Tyr Ala Thr Glu
    1100            1105                1110

Gln Gln Leu Gly Gln Ile Val Met Tyr Phe Phe Arg Asp Ser Asn
    1115            1120                1125

Ala Val Arg Phe Pro Asp Ala Gly Lys Thr Lys Ile Gln Ile Ser
    1130            1135                1140

Ala Asp Gly Lys Asn Trp Thr Asp Leu Ala Ala Thr Glu Thr Ile
    1145            1150                1155

Ala Ala Gln Glu Ser Ser Asp Arg Val Lys Pro Tyr Thr Tyr Asp
    1160            1165                1170

Phe Ala Pro Val Gly Ala Thr Phe Val Lys Val Thr Val Thr Asn
    1175            1180                1185

Ala Asp Thr Thr Thr Pro Ser Gly Val Val Cys Ala Gly Leu Thr
    1190            1195                1200

Glu Ile Glu Leu Lys Thr Ala Thr Ser Lys Phe Val Thr Asn Thr
    1205            1210                1215

Ser Ala Ala Leu Ser Ser Leu Thr Val Asn Gly Thr Lys Val Ser
    1220            1225                1230

Asp Ser Val Leu Ala Ala Gly Ser Tyr Asn Thr Pro Ala Ile Ile
    1235            1240                1245

Ala Asp Val Lys Ala Glu Gly Glu Gly Asn Ala Ser Val Thr Val
    1250            1255                1260

Leu Pro Ala His Asp Asn Val Ile Arg Val Ile Thr Glu Ser Glu
    1265            1270                1275

Asp His Val Thr Arg Lys Thr Phe Thr Ile Asn Leu Gly Thr Glu
    1280            1285                1290

Gln Glu Phe
    1295

<210> SEQ ID NO 7
<211> LENGTH: 453
<212> TYPE: PRT
<213> ORGANISM: Bifidobacterium bifidum

<400> SEQUENCE: 7

Gln Asn Arg Thr Ser Asp Phe Asp Ala Asn Trp Lys Phe Met Leu Ser
1               5                   10                  15

Asp Ser Val Gln Ala Gln Asp Pro Ala Phe Asp Ser Ala Trp Gln
                20                  25                  30

Gln Val Asp Leu Pro His Asp Tyr Ser Ile Thr Gln Lys Tyr Ser Gln
            35                  40                  45

Ser Asn Glu Ala Glu Ser Ala Tyr Leu Pro Gly Gly Thr Gly Trp Tyr
        50                  55                  60

Arg Lys Ser Phe Thr Ile Asp Arg Asp Leu Ala Gly Lys Arg Ile Ala
65                  70                  75                  80

Ile Asn Phe Asp Gly Val Tyr Met Asn Ala Thr Val Trp Phe Asn Gly
```

```
                85                  90                  95
Val Lys Leu Gly Thr His Pro Tyr Gly Tyr Ser Pro Phe Ser Phe Asp
            100                 105                 110

Leu Thr Gly Asn Ala Lys Phe Gly Glu Asn Thr Ile Val Val Lys
        115                 120                 125

Val Glu Asn Arg Leu Pro Ser Ser Arg Trp Tyr Ser Gly Ser Gly Ile
    130                 135                 140

Tyr Arg Asp Val Thr Leu Thr Val Thr Asp Gly Val His Val Gly Asn
145                 150                 155                 160

Asn Gly Val Ala Ile Lys Thr Pro Ser Leu Ala Thr Gln Asn Gly Gly
                165                 170                 175

Asp Val Thr Met Asn Leu Thr Thr Lys Val Ala Asn Asp Thr Glu Ala
            180                 185                 190

Ala Ala Asn Ile Thr Leu Lys Gln Thr Val Phe Pro Lys Gly Gly Lys
        195                 200                 205

Thr Asp Ala Ala Ile Gly Thr Val Thr Ala Ser Lys Ser Ile Ala
    210                 215                 220

Ala Gly Ala Ser Ala Asp Val Thr Ser Thr Ile Thr Ala Ala Ser Pro
225                 230                 235                 240

Lys Leu Trp Ser Ile Lys Asn Pro Asn Leu Tyr Thr Val Arg Thr Glu
                245                 250                 255

Val Leu Asn Gly Gly Lys Val Leu Asp Thr Tyr Asp Thr Glu Tyr Gly
            260                 265                 270

Phe Arg Trp Thr Gly Phe Asp Ala Thr Ser Gly Phe Ser Leu Asn Gly
        275                 280                 285

Glu Lys Val Lys Leu Lys Gly Val Ser Met His His Asp Gln Gly Ser
    290                 295                 300

Leu Gly Ala Val Ala Asn Arg Arg Ala Ile Glu Arg Gln Val Glu Ile
305                 310                 315                 320

Leu Gln Lys Met Gly Val Asn Ser Ile Arg Thr Thr His Asn Pro Ala
                325                 330                 335

Ala Lys Ala Leu Ile Asp Val Cys Asn Glu Lys Gly Val Leu Val Val
            340                 345                 350

Glu Glu Val Phe Asp Met Trp Asn Arg Ser Lys Asn Gly Asn Thr Glu
        355                 360                 365

Asp Tyr Gly Lys Trp Phe Gly Gln Ala Ile Ala Gly Asp Asn Ala Val
    370                 375                 380

Leu Gly Gly Asp Lys Asp Glu Thr Trp Ala Lys Phe Asp Leu Thr Ser
385                 390                 395                 400

Thr Ile Asn Arg Asp Arg Asn Ala Pro Ser Val Ile Met Trp Ser Leu
                405                 410                 415

Gly Asn Glu Met Met Glu Gly Ile Ser Gly Ser Val Ser Gly Phe Pro
            420                 425                 430

Ala Thr Ser Ala Lys Leu Val Ala Trp Thr Lys Ala Ala Asp Ser Thr
        435                 440                 445

Arg Pro Met Thr Tyr
    450

<210> SEQ ID NO 8
<211> LENGTH: 5160
<212> TYPE: DNA
<213> ORGANISM: Artificial Sequence
<220> FEATURE:
<223> OTHER INFORMATION: Nucleotide sequence encoding an extracellular
      lactase
```

<400> SEQUENCE: 8

```
gcagttgaag atgcaacaag aagcgatagc acaacacaaa tgtcatcaac accggaagtt      60
gtttattcat cagcggtcga tagcaaacaa aatcgcacaa gcgattttga tgcgaactgg     120
aaatttatgc tgtcagatag cgttcaagca caagatccgg catttgatga ttcagcatgg     180
caacaagttg atctgccgca tgattatagc atcacacaga aatatagcca aagcaatgaa     240
gcagaatcag catatcttcc gggaggcaca ggctggtata gaaaaagctt acaattgat     300
agagatctgg caggcaaacg cattgcgatt aattttgatg cgtctatat gaatgcaaca     360
gtctggttta tggcgttaa actgggcaca catccgtatg ctattcacc gttttcattt     420
gatctgacag gcaatgcaaa atttggcgga gaaaacacaa ttgtcgtcaa agttgaaaat     480
agactgccgt catcaagatg gtattcaggc agcggcattt atagagatgt tacactgaca     540
gttacagatg cgttcatgt tggcaataat ggcgtcgcaa ttaaaacacc gtcactggca     600
acacaaaatg gcggagatgt cacaatgaac ctgacaacaa agtcgcgaa tgatacagaa     660
gcagcagcga acattacact gaaacagaca gttttccga aggcggaaa aacggatgca     720
gcaattggca cagttacaac agcatcaaaa tcaattgcag caggcgcatc agcagatgtt     780
acaagcacaa ttacagcagc aagcccgaaa ctgtggtcaa ttaaaaaccc gaacctgtat     840
acagttagaa cagaagttct gaacggaggc aaagttctgg atacatatga tacagaatat     900
ggctttcgct ggacaggctt tgatgcaaca tcaggctttt cactgaatgg cgaaaaagtc     960
aaactgaaag gcgttagcat gcatcatgat caaggctcac ttggcgcagt tgcaaataga    1020
cgcgcaattg aaagacaagt cgaaatcctg caaaaaatgg gcgtcaatag cattcgcaca    1080
acacataatc cggcagcaaa agcactgatt gatgtctgca atgaaaaagg cgttctggtt    1140
gtcgaagaag tctttgatat gtggaaccgc agcaaaaatg gcaacacgga agattatggc    1200
aaatggtttg gccaagcaat tgcaggcgat aatgcagttc tgggaggcga taaagatgaa    1260
acatgggcga aatttgatct tacatcaaca attaaccgcg atagaaatgc accgtcagtt    1320
attatgtggt cactgggcaa tgaaatgatg gaaggcattt caggctcagt ttcaggcttt    1380
ccggcaacat cagcaaaact ggttgcatgg acaaaagcag cagattcaac aagaccgatg    1440
acatatggcg ataacaaaat taaagcgaac tggaacgaat caaatacaat gggcgataat    1500
ctgacagcaa atgcggagt tgttggcaca aattattcag atggcgcaaa ctatgataaa    1560
attcgtacaa cacatccgtc atgggcaatt tatggctcag aaacagcatc agcgattaat    1620
agccgtggca tttataatag aacaacaggc ggagcacaat catcagataa acagctgaca    1680
agctatgata attcagcagt tggctgggga gcagttgcat catcagcatg gtatgatgtt    1740
gttcagagag attttgtcgc aggcacatat gtttggacag gatttgatta tctgggcgaa    1800
ccgacaccgt ggaatggcac aggctcaggc gcagttggct catggccgtc accgaaaaat    1860
agctattttg gcatcgttga tacagcaggc tttccgaaag atacatatta ttttatcag    1920
agccagtgga atgatgatgt tcatacactg catattcttc cggcatggaa tgaaaatgtt    1980
gttgcaaaag gctcaggcaa taatgttccg gttgtcgttt atacagatgc agcgaaagtg    2040
aaactgtatt ttacaccgaa aggctcaaca gaaaaaagac tgatcggcga aaaatcattt    2100
acaaaaaaaa caacagcggc aggctataca tatcaagtct atgaaggcag cgataaagat    2160
tcaacagcgc ataaaaacat gtatctgaca tggaatgttc cgtgggcaga aggcacaatt    2220
tcagcggaag cgtatgatga aaataatcgc ctgattccgg aaggcagcac agaaggcaac    2280
```

```
gcatcagtta caacaacagg caaagcagca aaactgaaag cagatgcgga tcgcaaaaca    2340
attacagcgg atggcaaaga tctgtcatat attgaagtcg atgtcacaga tgcaaatggc    2400
catattgttc cggatgcagc aaatagagtc acatttgatg ttaaaggcgc aggcaaactg    2460
gttggcgttg ataatggctc atcaccggat catgattcat atcaagcgga taaccgcaaa    2520
gcattttcag gcaaagtcct ggcaattgtt cagtcaacaa agaagcagg cgaaattaca    2580 gttacagcaa aagcagatgg cctgcaatca agcacagtta aaattgcaac aacagcagtt    2640
ccgggaacaa gcacagaaaa aacagtccgc agctttatt acagccgcaa ctattatgtc     2700
aaaacaggca acaaaccgat tctgccgtca gatgttgaag ttcgctattc agatggaaca    2760
agcgatagac aaaacgttac atgggatgca gtttcagatg atcaaattgc aaaagcaggc    2820
tcattttcag ttgcaggcac agttgcaggc caaaaaatta gcgttcgcgt cacaatgatt    2880
gatgaaattg gcgcactgct gaattattca gcaagcacac cggttggcac accggcagtt    2940
cttccgggat caagaccggc agtcctgccg gatggcacag tcatcagc aaattttgca      3000 gtccattgga caaaaccggc agatacagtc tataatacag caggcacagt caaagtaccg    3060
ggaacagcaa cagttttttgg caaagaattt aaagtcacag cgacaattag agttcaaaga    3120
agccaagtta caattggctc atcagtttca ggaaatgcac tgagactgac acaaaatatt    3180
ccggcagata acaatcaga tacactggat gcgattaaag atggctcaac aacagttgat     3240
gcaaatacag gcgaggcgc aaatccgtca gcatggacaa attgggcata ttcaaaagca    3300
ggccataaca cagcggaaat tacatttgaa tatgcgacag acaacaact gggccagatc     3360 gtcatgtatt tttttcgcga tagcaatgca gttagatttc cggatgctgg caaaacaaaa    3420
attcagatca gcgcagatgg caaaaattgg acagatctgg cagcaacaga aacaattgca    3480
gcgcaagaat caagcgatag agtcaaaccg tatacatatg attttgcacc ggttggcgca    3540
acatttgtta aagtgacagt cacaaacgca gatacaacaa caccgtcagg cgttgtttgc    3600
gcaggcctga cagaaattga actgaaaaca gcgacaagca aatttgtcac aaatacatca    3660
gcagcactgt catcacttac agtcaatggc acaaaagttt cagattcagt tctggcagca    3720
ggctcatata acacaccggc aattatcgca gatgttaaag cggaaggcga aggcaatgca    3780
agcgttacag tccttccggc acatgataat gttattcgcg tcattacaga aagcgaagat    3840
catgtcacac gcaaaacatt tacaatcaac ctgggcacag aacaagaatt ccggctgat    3900 tcagatgaaa gagattatcc ggcagcagat atgacagtca cagttggctc agaacaaaca    3960
tcaggcacag caacagaagg accgaaaaaa tttgcagtcg atggcaacac atcaacatat    4020
tggcatagca attggacacc gacaacagtt aatgatctgt ggatcgcgtt tgaactgcaa    4080
aaaccgacaa aactggatgc actgagatat cttccgcgtc cggcaggctc aaaaaatggc    4140
agcgtcacag aatataaagt tcaggtgtca gatgatgaa caaactggac agatgcaggc    4200
tcaggcacat ggacaacgga ttatggctgg aaactggcgg aatttaatca accggtcaca    4260
acaaaacatg ttagactgaa agcggttcat acatatgcag atagcggcaa cgataaattt    4320
atgagcgcaa gcgaaattag actgagaaaa gcggtcgata caacggatat ttcaggcgca    4380
acagttacag ttccggcaaa actgacagtt gatagagttg atgcagatca tccggcaaca    4440
tttgcaacaa aagatgtcac agttacactg ggagatgcaa cactgagata tggcgttgat    4500
tatctgctgg attatgcagg caatacagca gttggcaaag caacagtgac agttagaggc    4560
attgataaat attcaggcac agtcgcgaaa acatttacaa ttgaactgaa aaatgcaccg    4620
gcaccggaac cgacactgac atcagttagc gtcaaaacaa aaccgagcaa actgacatat    4680
```

```
gttgtcggag atgcatttga tccggcaggc ctggttctgc aacatgatag acaagcagat    4740
agacctccgc aaccgctggt tggcgaacaa gcggatgaac gcggactgac atgcggcaca    4800
agatgcgata gagttgaaca actgcgcaaa catgaaaata gagaagcgca tagaacaggc    4860
ctggatcatc tggaatttgt tggcgcagca gatggcgcag ttggagaaca agcaacattt    4920
aaagtccatg tccatgcaga tcagggagat ggcagacatg atgatgcaga tgaacgcgat    4980
attgatccgc atgttccggt cgatcatgca gttggcgaac tggcaagagc agcatgccat    5040
catgttattg gcctgagagt cgatacacat agacttaaag caagcggctt tcaaattccg    5100
gctgatgata tggcagaaat cgatcgcatt acaggctttc atcgttttga acgccatgtc    5160
```

<210> SEQ ID NO 9
<211> LENGTH: 2661
<212> TYPE: DNA
<213> ORGANISM: Artificial Sequence
<220> FEATURE:
<223> OTHER INFORMATION: Nucleotide sequence encoding BIF_917

<400> SEQUENCE: 9

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat tgatgattc agcatggcaa     180 caagttgatc tgccgcatga ttatagcatc acacagaaat atagccaaag caatgaagca     240
gaatcagcat atcttccggg aggcacaggc tggtatagaa aaagctttac aattgatgga     300
gatctggcag gcaaacgcat tgcgattaat tttgatggcg tctatatgaa tgcaacagtc     360
tggtttaatg gcgttaaact gggcacacat ccgtatggct attaccgtt ttcatttgat     420 ctgacaggca atgcaaaatt tggcggagaa aacacaattg tcgtcaaagt gaaaatagaa    480
ctgccgtcat caagatggta ttcaggcagc ggcattttata gagatgttac actgacagtt     540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa gacaagtcga atcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca cacgcaagaa ttatggcaaa    1200
tggtttggcc aagcaattgc aggcgataat gcagttctgg gaggcgataa agatgaaaca    1260
tgggcgaaat tgatcttac atcaacaatt aaccgcgata gaaatgcacc gtcagttatt    1320
atgtggtcac tggcaatgaa atgatgaaa ggcatttcag gctcagtttc aggctttccg    1380
gcaacatcag caaaactggt tgcatggaca aaagcagcag attcaacaag accgatgaca    1440
tatggcgata caaaaattaa agcgaactgg aacgaatcaa atacaatggg cgataatctg    1500
acagcaaatg gcggagttgt tggcacaaat tattcagatg gcgcaaacta tgataaaatt    1560
```

```
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg caaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac a                                              2661

<210> SEQ ID NO 10
<211> LENGTH: 2895
<212> TYPE: DNA
<213> ORGANISM: Artificial Sequence
<220> FEATURE:
<223> OTHER INFORMATION: Nucleotide sequence encoding BIF_995

<400> SEQUENCE: 10
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat tgatgattca gcatggcaa     180 caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt tcatttgat     420 ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag cggaaaaac ggatgcagca     720 attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
```

```
ctgaaaggcg ttagcatgca tcatgatcaa ggctcacttg gcgcagttgc aaatagacgc    1020
gcaattgaaa gacaagtcga atcctgcaa aaaatgggcg tcaatagcat tcgcacaaca     1080
cataatccgg cagcaaaagc actgattgat gtctgcaatg aaaaggcgt tctggttgtc     1140 gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc     1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aatgttgtt    1980 gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata tggctcatc accgatcat gattcatatc aagcggataa ccgcaaagca      2520
ttttcaggca aagtcctggc aattgttcag tcaacaaaag aagcaggcga attacagtt     2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactg                                                    2895
```

<210> SEQ ID NO 11
<211> LENGTH: 3114
<212> TYPE: DNA
<213> ORGANISM: Artificial Sequence
<220> FEATURE:
<223> OTHER INFORMATION: Nucleotide sequence encoding BIF_1068

<400> SEQUENCE: 11

```
gttgaagatg caacaagaag cgatagcaca acacaaatgt catcaacacc ggaagttgtt       60
```

```
tattcatcag cggtcgatag caaacaaaat cgcacaagcg attttgatgc gaactggaaa    120
tttatgctgt cagatagcgt tcaagcacaa gatccggcat ttgatgattc agcatggcaa    180
caagttgatc tgccgcatga ttatagcatc acacagaaat atagccaaag caatgaagca    240
gaatcagcat atcttccggg aggcacaggc tggtatagaa aaagctttac aattgataga    300
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaagtcaaa    960 ctgaaaggcg ttagcatgca tcatgatcaa ggctcacttg gcgcagttgc aaatagacgc    1020
gcaattgaaa gacaagtcga atcctgcaa aaaatgggcg tcaatagcat cgcacaaca    1080 cataatccgg cagcaaaagc actgattgat gtctgcaatg aaaaaggcgt tctggttgtc    1140
gaagaagtct ttgatatgtg gaaccgcagc aaaaatggca cacgaaga ttatggcaaa    1200 tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg cgcaaactga tgataaaatt    1560
cgtacaacac atccgtcatg ggcaattat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aatgttgtt    1980 gcaaaaggct caggcaataa tgttccggtt gtcgtttata cagatgcagc gaaagtgaaa    2040 ctgtattta caccgaaagg ctcaacagaa aaaagactga tcggcgaaaa atcatttaca    2100
aaaaaaacaa cagcggcagg ctatacatat caagtctatg aaggcagcga taagattca    2160 acagcgcata aaaacatgta tctgacatgg aatgttccgt gggcagaagg cacaatttca    2220
gcggaagcgt atgatgaaaa taatcgcctg attccggaag cagcacaga aggcaacgca    2280 tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
```

```
ggcgttgata atggctcatc accggatcat gattcatatc aagcggataa ccgcaaagca    2520
ttttcaggca aagtcctggc aattgttcag tcaacaaaag aagcaggcga aattacagtt    2580
acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaaattgcaaa agcaggctca    2820 ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaa         3114
```

<210> SEQ ID NO 12
<211> LENGTH: 3426
<212> TYPE: DNA
<213> ORGANISM: Artificial Sequence
<220> FEATURE:
<223> OTHER INFORMATION: Nucleotide sequence encoding BIF_1172

<400> SEQUENCE: 12

```
gttgaagatg caacaagaag cgatagcaca acacaaatgt catcaacacc ggaagttgtt      60
tattcatcag cggtcgatag caaacaaaat cgcacaagcg atttttgatgc gaactggaaa    120 tttatgctgt cagatagcgt tcaagcacaa gatccggcat ttgatgattc agcatggcaa    180
caagttgatc tgccgcatga ttatagcatc acacagaaat atagccaaag caatgaagca    240
gaatcagcat atcttccggg aggcacaggc tggtatagaa aaagctttac aattgataga    300
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa acacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggcttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa gacaagtcga aatcctgcaa aaaatgggcg tcaatagcat cgcacaaca   1080 cataatccgg cagcaaaagc actgattgat gtctgcaatg aaaaaggcgt tctggttgtc   1140
gaagaagtct ttgatatgtg gaaccgcagc aaaaatggca cacgaaaga ttatggcaaa   1200 tggtttggcc aagcaattgc aggcgataat gcagttctgg gaggcgataa agatgaaaca   1260 tgggcgaaaat ttgatcttac atcaacaatt aaccgcgata gaaatgcacc gtcagttatt   1320
atgtggtcac tgggcaatga aatgatggaa ggcatttcag gctcagttc aggcttttccg   1380
```

```
gcaacatcag caaaactggt tgcatggaca aaagcagcag attcaacaag accgatgaca      1440
tatggcgata acaaaattaa agcgaactgg aacgaatcaa atacaatggg cgataatctg      1500
acagcaaatg gcggagttgt tggcacaaat tattcagatg gcgcaaacta tgataaaatt      1560
cgtacaacac atccgtcatg ggcaatttat ggctcagaaa cagcatcagc gattaatagc      1620
cgtggcattt ataatagaac aacaggcgga gcacaatcat cagataaaca gctgacaagc      1680
tatgataatt cagcagttgg ctggggagca gttgcatcat cagcatggta tgatgttgtt      1740
cagagagatt ttgtcgcagg cacatatgtt tggacaggat ttgattatct gggcgaaccg      1800
acaccgtgga atggcacagg ctcaggcgca gttggctcat ggccgtcacc gaaaaatagc      1860
tattttggca tcgttgatac agcaggcttt ccgaaagata catattattt ttatcagagc      1920
cagtggaatg atgatgttca tacactgcat attcttccgg catggaatga aatgttgtt       1980 gcaaaaggct caggcaataa tgttccggtt gtcgtttata cagatgcagc gaaagtgaaa      2040
ctgtatttta caccgaaagg ctcaacagaa aaaagactga tcggcgaaaa atcatttaca      2100
aaaaaaacaa cagcggcagg ctatacatat caagtctatg aaggcagcga taagattca       2160 acagcgcata aaaacatgta tctgacatgg aatgttccgt gggcagaagg cacaatttca      2220
gcggaagcgt atgatgaaaa taatcgcctg attccggaag cagcacaga aggcaacgca       2280 tcagttacaa caacaggcaa agcagcaaaa ctgaaagcag atgcggatcg caaaacaatt      2340
acagcggatg gcaaagatct gtcatatatt gaagtcgatg tcacagatgc aaatggccat      2400
attgttccgg atgcagcaaa tagagtcaca tttgatgtta aaggcgcagg caaactggtt      2460
ggcgttgata atggctcatc accgatcat gattcatatc aagcggataa ccgcaaagca       2520
ttttcaggca agtcctggc aattgttcag tcaacaaaag aagcaggcga attacagtt        2580 acagcaaaag cagatggcct gcaatcaagc acagttaaaa ttgcaacaac agcagttccg      2640
ggaacaagca cagaaaaaac agtccgcagc tttattaca gccgcaacta ttatgtcaaa       2700
acaggcaaca aaccgattct gccgtcagat gttgaagttc gctattcaga tggaacaagc      2760
gatagacaaa acgttacatg ggatgcagtt tcagatgatc aaattgcaaa agcaggctca      2820
ttttcagttg caggcacagt tgcaggccaa aaaattagcg ttcgcgtcac aatgattgat      2880
gaaattggcg cactgctgaa ttattcagca agcacaccgg ttggcacacc ggcagttctt      2940
ccgggatcaa gaccggcagt cctgccggat ggcacagtca catcagcaaa ttttgcagtc      3000
cattggacaa aaccggcaga tacagtctat aatacagcag gcacagtcaa agtaccggga      3060
acagcaacag ttttttggcaa agaatttaaa gtcacagcga caattagagt tcaaagaagc      3120
caagttacaa ttggctcatc agtttcagga aatgcactga gactgacaca aaatattccg      3180
gcagataaac aatcagatac actggatgcg attaaagatg gctcaacaac agttgatgca      3240
aatacaggcg gaggcgcaaa tccgtcagca tggacaaatt gggcatattc aaaagcaggc      3300
cataacacag cggaaattac atttgaatat gcgacagaac aacaactggg ccagatcgtc      3360
atgtattttt ttcgcgatag caatgcagtt agatttccgg atgctggcaa aacaaaaatt      3420
cagatc                                                                 3426
```

<210> SEQ ID NO 13
<211> LENGTH: 3633
<212> TYPE: DNA
<213> ORGANISM: Artificial Sequence
<220> FEATURE:
<223> OTHER INFORMATION: Nucleotide sequence encoding BIF_1241

<400> SEQUENCE: 13

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat tgatgattc agcatggcaa      180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag cggaaaaaac ggatgcagca     720
attggcacag ttacaacagc atcaaaatca attgcagcag cgcatcagc agatgttaca      780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
ctgaaaggcg ttagcatgca tcatgatcaa ggctcacttg gcgcagttgc aaatagacgc    1020
gcaattgaaa gacaagtcga aatcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat tgattatct gggcgaaccg     1800
acaccgtgga tggcacagg ctcaggcgca gttggctcat ggccgtcacc gaaaaatagc      1860
tattttggca tcgttgatac agcaggcttt ccgaaagata catattattt ttatcagagc    1920
cagtggaatg atgatgttca tacactgcat attcttccgg catggaatga aatgttgtt     1980
gcaaaaggct caggcaataa tgttccggtt gtcgtttata cagatgcagc gaaagtgaaa    2040
ctgtattta caccgaaagg ctcaacagaa aaaagactga tcggcgaaaa atcatttaca     2100
aaaaaacaa cagcggcagg ctatacatat caagtctatg aaggcagcga taagattca      2160
acagcgcata aaaacatgta tctgacatgg aatgttccgt gggcagaagg cacaattta      2220
gcggaagcgt atgatgaaaa taatcgcctg attccggaag cagcacagaa aggcaacgca    2280
tcagttacaa caacaggcaa agcagcaaaa ctgaaagcag atgcggatcg caaaacaatt    2340
```

```
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt     2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg aca                                  3633
```

<210> SEQ ID NO 14
<211> LENGTH: 3888
<212> TYPE: DNA
<213> ORGANISM: Artificial Sequence
<220> FEATURE:
<223> OTHER INFORMATION: Nucleotide sequence encoding BIF_1326

<400> SEQUENCE: 14

```
gttgaagatg caacaagaag cgatagcaca acacaaatgt catcaacacc ggaagttgtt      60
tattcatcag cggtcgatag caaacaaaat cgcacaagcg atttttgatgc gaactggaaa    120 tttatgctgt cagatagcgt tcaagcacaa gatccggcat ttgatgattc agcatggcaa    180
caagttgatc tgccgcatga ttatagcatc acacagaaat atagccaaag caatgaagca    240
gaatcagcat atcttccggg aggcacaggc tggtatagaa aaagctttac aattgataga    300
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa acacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aacaccgtc actggcaaca    600 caaaatggcg gagatgtcac aatgaacctg acaacaaaag tcgcgaatga tacagaagca    660
gcagcgaaca ttacactgaa acagacagtt tttccgaaag cggaaaaaac ggatgcagca    720
attggcacag ttacaacagc atcaaaatca attgcagcag gcgcatcagc agatgttaca    780
```

```
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg cgcagttgc aaatagacgc    1020
gcaattgaaa gacaagtcga atcctgcaa aaaatgggcg tcaatagcat tcgcacaaca    1080
cataatccgg cagcaaaagc actgattgat gtctgcaatg aaaaggcgt tctggttgtc    1140
gaagaagtct ttgatatgtg gaaccgcagc aaaaatggca cacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tggcaatga aatgatgaa ggcatttcag gctcagtttc aggctttccg    1380
gcaacatcag caaaactggt tgcatggaca aaagcagcag attcaacaag accgatgaca    1440
tatggcgata caaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccgaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca agtcctggc aattgttcag tcaacaaaag aagcaggcga aattacagtt    2580
acagcaaaag cagatggcct gcaatcaagc acagttaaaa ttgcaacaac agcagttccg    2640
ggaacaagca cagaaaaaac agtccgcagc tttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
```

```
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg acaagcaaat ttgtcacaaa tacatcagca    3660
gcactgtcat cacttacagt caatggcaca aaagtttcag attcagttct ggcagcaggc    3720
tcatataaca caccggcaat tatcgcagat gttaaagcgg aaggcgaagg caatgcaagc    3780
gttacagtcc ttccggcaca tgataatgtt attcgcgtca ttacagaaag cgaagatcat    3840
gtcacacgca aaacatttac aatcaacctg ggcacagaac aagaattt                 3888
```

<210> SEQ ID NO 15
<211> LENGTH: 30
<212> TYPE: DNA
<213> ORGANISM: Artificial Sequence
<220> FEATURE:
<223> OTHER INFORMATION: Forward primer for generation of BIF variants

<400> SEQUENCE: 15

```
ggggtaacta gtggaagatg caacaagaag                                       30
```

<210> SEQ ID NO 16
<211> LENGTH: 35
<212> TYPE: DNA
<213> ORGANISM: Artificial Sequence
<220> FEATURE:
<223> OTHER INFORMATION: Reverse primer for BIF917

<400> SEQUENCE: 16

```
gcgcttaatt aattatgttt tttctgtgct tgttc                                 35
```

<210> SEQ ID NO 17
<211> LENGTH: 38
<212> TYPE: DNA
<213> ORGANISM: Artificial Sequence
<220> FEATURE:
<223> OTHER INFORMATION: Reverse primer for BIF995

<400> SEQUENCE: 17

```
gcgcttaatt aattacagtg cgccaatttc atcaatca                              38
```

<210> SEQ ID NO 18
<211> LENGTH: 35
<212> TYPE: DNA
<213> ORGANISM: Artificial Sequence
<220> FEATURE:
<223> OTHER INFORMATION: Reverse primer for BIF1068

<400> SEQUENCE: 18

```
gcgcttaatt aattattgaa ctctaattgt cgctg                                 35
```

<210> SEQ ID NO 19
<211> LENGTH: 36
<212> TYPE: DNA
<213> ORGANISM: Artificial Sequence

```
<220> FEATURE:
<223> OTHER INFORMATION: Reverse primer for BIF1241

<400> SEQUENCE: 19
gcgcttaatt aattatgtcg ctgttttcag ttcaat                                    36

<210> SEQ ID NO 20
<211> LENGTH: 35
<212> TYPE: DNA
<213> ORGANISM: Artificial Sequence
<220> FEATURE:
<223> OTHER INFORMATION: Reverse primer for BIF1326

<400> SEQUENCE: 20
gcgcttaatt aattaaaatt cttgttctgt gccca                                     35

<210> SEQ ID NO 21
<211> LENGTH: 38
<212> TYPE: DNA
<213> ORGANISM: Artificial Sequence
<220> FEATURE:
<223> OTHER INFORMATION: Reverse primer for BIF1478

<400> SEQUENCE: 21
gcgcttaatt aattatctca gtctaatttc gcttgcgc                                  38

<210> SEQ ID NO 22
<211> LENGTH: 1720
<212> TYPE: PRT
<213> ORGANISM: Bifidobacterium bifidum

<400> SEQUENCE: 22
```

Val Glu Asp Ala Thr Arg Ser Asp Ser Thr Gln Met Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile

```
               210                 215                 220
Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
                275                 280                 285

Gly Lys Val Leu Asp Thr Tyr Asp Thr Glu Tyr Gly Phe Arg Trp Thr
                290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
                355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
                450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
                515                 520                 525

Ile Tyr Gly Ser Glu Thr Ala Ser Ala Ile Asn Ser Arg Gly Ile Tyr
                530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
                595                 600                 605

Gly Ala Val Gly Ser Trp Pro Ser Pro Lys Asn Ser Tyr Phe Gly Ile
                610                 615                 620

Val Asp Thr Ala Gly Phe Pro Lys Asp Thr Tyr Tyr Phe Tyr Gln Ser
625                 630                 635                 640
```

```
Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050
```

-continued

| | | | | | | | | | | | |
|---|---|---|---|---|---|---|---|---|---|---|---|
| Arg | Leu 1055 | Thr | Gln | Asn | Ile | Pro 1060 | Ala | Asp | Lys | Gln | Ser 1065 | Asp | Thr | Leu |

Arg Leu Thr Gln Asn Ile Pro Ala Asp Lys Gln Ser Asp Thr Leu
    1055                1060               1065

Asp Ala Ile Lys Asp Gly Ser Thr Thr Val Asp Ala Asn Thr Gly
1070            1075                1080

Gly Gly Ala Asn Pro Ser Ala Trp Thr Asn Trp Ala Tyr Ser Lys
    1085            1090                1095

Ala Gly His Asn Thr Ala Glu Ile Thr Phe Glu Tyr Ala Thr Glu
1100            1105                1110

Gln Gln Leu Gly Gln Ile Val Met Tyr Phe Phe Arg Asp Ser Asn
    1115            1120                1125

Ala Val Arg Phe Pro Asp Ala Gly Lys Thr Lys Ile Gln Ile Ser
1130            1135                1140

Ala Asp Gly Lys Asn Trp Thr Asp Leu Ala Ala Thr Glu Thr Ile
    1145            1150                1155

Ala Ala Gln Glu Ser Ser Asp Arg Val Lys Pro Tyr Thr Tyr Asp
1160            1165                1170

Phe Ala Pro Val Gly Ala Thr Phe Val Lys Val Thr Val Thr Asn
    1175            1180                1185

Ala Asp Thr Thr Thr Pro Ser Gly Val Val Cys Ala Gly Leu Thr
1190            1195                1200

Glu Ile Glu Leu Lys Thr Ala Thr Ser Lys Phe Val Thr Asn Thr
    1205            1210                1215

Ser Ala Ala Leu Ser Ser Leu Thr Val Asn Gly Thr Lys Val Ser
1220            1225                1230

Asp Ser Val Leu Ala Ala Gly Ser Tyr Asn Thr Pro Ala Ile Ile
    1235            1240                1245

Ala Asp Val Lys Ala Glu Gly Glu Gly Asn Ala Ser Val Thr Val
1250            1255                1260

Leu Pro Ala His Asp Asn Val Ile Arg Val Ile Thr Glu Ser Glu
    1265            1270                1275

Asp His Val Thr Arg Lys Thr Phe Thr Ile Asn Leu Gly Thr Glu
1280            1285                1290

Gln Glu Phe Pro Ala Asp Ser Asp Glu Arg Asp Tyr Pro Ala Ala
    1295            1300                1305

Asp Met Thr Val Thr Val Gly Ser Glu Gln Thr Ser Gly Thr Ala
1310            1315                1320

Thr Glu Gly Pro Lys Lys Phe Ala Val Asp Gly Asn Thr Ser Thr
    1325            1330                1335

Tyr Trp His Ser Asn Trp Thr Pro Thr Thr Val Asn Asp Leu Trp
1340            1345                1350

Ile Ala Phe Glu Leu Gln Lys Pro Thr Lys Leu Asp Ala Leu Arg
    1355            1360                1365

Tyr Leu Pro Arg Pro Ala Gly Ser Lys Asn Gly Ser Val Thr Glu
1370            1375                1380

Tyr Lys Val Gln Val Ser Asp Asp Gly Thr Asn Trp Thr Asp Ala
    1385            1390                1395

Gly Ser Gly Thr Trp Thr Thr Asp Tyr Gly Trp Lys Leu Ala Glu
1400            1405                1410

Phe Asn Gln Pro Val Thr Thr Lys His Val Arg Leu Lys Ala Val
    1415            1420                1425

His Thr Tyr Ala Asp Ser Gly Asn Asp Lys Phe Met Ser Ala Ser
1430            1435                1440

Glu Ile Arg Leu Arg Lys Ala Val Asp Thr Thr Asp Ile Ser Gly

```
              1445              1450              1455
Ala Thr Val Thr Val Pro Ala Lys Leu Thr Val Asp Arg Val Asp
        1460              1465              1470

Ala Asp His Pro Ala Thr Phe Ala Thr Lys Asp Val Thr Val Thr
        1475              1480              1485

Leu Gly Asp Ala Thr Leu Arg Tyr Gly Val Asp Tyr Leu Leu Asp
        1490              1495              1500

Tyr Ala Gly Asn Thr Ala Val Gly Lys Ala Thr Val Thr Val Arg
        1505              1510              1515

Gly Ile Asp Lys Tyr Ser Gly Thr Val Ala Lys Thr Phe Thr Ile
        1520              1525              1530

Glu Leu Lys Asn Ala Pro Ala Pro Glu Pro Thr Leu Thr Ser Val
        1535              1540              1545

Ser Val Lys Thr Lys Pro Ser Lys Leu Thr Tyr Val Val Gly Asp
        1550              1555              1560

Ala Phe Asp Pro Ala Gly Leu Val Leu Gln His Asp Arg Gln Ala
        1565              1570              1575

Asp Arg Pro Pro Gln Pro Leu Val Gly Glu Gln Ala Asp Glu Arg
        1580              1585              1590

Gly Leu Thr Cys Gly Thr Arg Cys Asp Arg Val Glu Gln Leu Arg
        1595              1600              1605

Lys His Glu Asn Arg Glu Ala His Arg Thr Gly Leu Asp His Leu
        1610              1615              1620

Glu Phe Val Gly Ala Ala Asp Gly Ala Val Gly Glu Gln Ala Thr
        1625              1630              1635

Phe Lys Val His Val His Ala Asp Gln Gly Asp Gly Arg His Asp
        1640              1645              1650

Asp Ala Asp Glu Arg Asp Ile Asp Pro His Val Pro Val Asp His
        1655              1660              1665

Ala Val Gly Glu Leu Ala Arg Ala Ala Cys His His Val Ile Gly
        1670              1675              1680

Leu Arg Val Asp Thr His Arg Leu Lys Ala Ser Gly Phe Gln Ile
        1685              1690              1695

Pro Ala Asp Asp Met Ala Glu Ile Asp Arg Ile Thr Gly Phe His
        1700              1705              1710

Arg Phe Glu Arg His Val Gly
        1715              1720

<210> SEQ ID NO 23
<211> LENGTH: 30
<212> TYPE: PRT
<213> ORGANISM: Bifidobacterium bifidum

<400> SEQUENCE: 23

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala
            20                  25                  30
```

The invention claimed is:

1. A host cell comprising an expression vector comprising a nucleic acid encoding a polypeptide having β-galactosidase and/or transgalactosylating activity wherein said host cell is modified to be cellulase, mannanase and pectinase deficient and wherein said polypeptide comprises an amino acid sequence having at least 90% sequence identity with SEQ ID NO: 1, and wherein said polypeptide consists of at most 980 amino acid residues, wherein said host cell is *Bacillus subtilis* or *Bacillus licheniformis* and wherein said cellulase is an endoglucanase.

2. The host cell of claim 1 in which the host cell is modified to be amylase deficient.

3. The host cell of claim 2 in which the host cell is modified by mutagenesis.

4. The host cell of claim 2 in which the host cell is modified by genetic manipulation.

5. The host cell of claim 4 in which the genetic manipulation is one-step gene disruption, marker insertion, site directed mutagenesis, deletion, RNA interference or antisense RNA.

6. The host cell of claim 5 in which the host cell is a bacterium.

7. The host cell of claim 6 in which the host cell is a lactic acid bacterium.

* * * * *